US010811128B2

(12) United States Patent
Fateh

(10) Patent No.: US 10,811,128 B2
(45) Date of Patent: *Oct. 20, 2020

(54) DETERMINING USE OF MEDICATION THROUGH CONSEQUENTIAL CHARACTERISTIC ACOUSTIC EMISSIONS

(71) Applicant: Kali Care, Inc., Mountain View, CA (US)

(72) Inventor: Sina Fateh, Sunnyvale, CA (US)

(73) Assignee: KALI CARE, INC., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/393,714

(22) Filed: Apr. 24, 2019

(65) Prior Publication Data
US 2019/0311793 A1 Oct. 10, 2019

Related U.S. Application Data

(63) Continuation of application No. 15/885,681, filed on Jan. 31, 2018.

(51) Int. Cl.
A61J 7/04 (2006.01)
G16H 20/13 (2018.01)
(Continued)

(52) U.S. Cl.
CPC ............ *G16H 20/13* (2018.01); *A61J 7/0015* (2013.01); *A61J 7/0436* (2015.05); *A61J 7/0418* (2015.05); *A61J 2200/30* (2013.01); *B65D 47/18* (2013.01)

(58) Field of Classification Search
CPC .................................................. G07F 17/0092
See application file for complete search history.

(56) References Cited

U.S. PATENT DOCUMENTS 3,230,661 A 1/1966 Gleason
4,418,842 A 12/1983 Di
(Continued)

FOREIGN PATENT DOCUMENTS

WO 2013120149 A1 8/2013
WO 2017162559 A1 9/2017

OTHER PUBLICATIONS

Harrison, Chris, et al., "Acoustic Barcodes: Passive, Durable and Inexpensive Notched Identification Tags", Oct. 7-10, 2012, 4 pgs., Human-Computer Interaction Institute and Heinz College Center for the Future of Work Carnegie Mellon University, Pittsburgh PA, Cambridge, MA, Copyright 2012 ACM 978-1-4503-1580.
(Continued)

Primary Examiner — Timothy R Waggoner
(74) Attorney, Agent, or Firm — Perkins Coie LLP

(57) ABSTRACT

Arrangements are provided for "smart" functionality with "dumb" containers, such as for tracking medication use to determine adherence. An acoustic emitter such as a whistle is engaged with a container such as an eye drop bottle. An event such as dispensing medication or opening the container causes a characteristic acoustic emission, such as an ultrasonic pitch of specific frequency. The emitter may be purposefully configured to produce the emission, may operate so that the emission is a natural consequence of dispensing medication (or other event), and may operate transparently to the user. The emitter may be part of a larger remote, such as a squeezable air-filled shell with an aperture to accept the container. A cell phone or other station receives the acoustic emission, and if a processor thereof determines that the emission is characteristic of the emitter the event is recorded, transmitted, displayed, or otherwise registered.

19 Claims, 27 Drawing Sheets

(51) Int. Cl.
*A61J 7/00* (2006.01)
*B65D 47/18* (2006.01)

(56) References Cited

U.S. PATENT DOCUMENTS

| | | | |
|---|---|---|---|
| 5,130,696 A | 7/1992 | Liebman | |
| 5,803,287 A | 9/1998 | Kusz | |
| 6,259,794 B1 | 7/2001 | Dobbins | |
| 6,299,006 B1 | 10/2001 | Samonek | |
| 8,328,775 B2 | 12/2012 | Gokhale et al. | |
| 9,283,150 B2 | 3/2016 | Bujalski et al. | |
| 9,918,905 B1 | 3/2018 | Howard et al. | |
| 10,138,036 B1 | 11/2018 | Schwimer | |
| 2002/0000908 A1 | 1/2002 | Burg et al. | |
| 2004/0155780 A1 | 8/2004 | Rapchak | |
| 2004/0173642 A1 | 9/2004 | Clifford et al. | |
| 2006/0186075 A1 | 8/2006 | Rainey et al. | |
| 2008/0110850 A1 | 5/2008 | Tilton | |
| 2009/0200258 A1 | 8/2009 | Maeda et al. | |
| 2013/0099900 A1* | 4/2013 | Pulvermacher | A47K 5/1217 340/10.42 |
| 2013/0099929 A1* | 4/2013 | Ophardt | A47K 5/1217 340/573.1 |
| 2014/0088524 A1 | 3/2014 | Marx | |
| 2014/0182584 A1* | 7/2014 | Sutherland | A61M 15/009 128/200.23 |
| 2014/0228783 A1 | 8/2014 | Kraft | |
| 2014/0257206 A1 | 9/2014 | Fateh | |
| 2015/0359667 A1 | 12/2015 | Brue | |
| 2016/0106375 A1* | 4/2016 | Leydon | A61B 5/087 600/538 |
| 2016/0283967 A1 | 9/2016 | Mitchell | |
| 2018/0310780 A1* | 11/2018 | Mahaffey | G01H 17/00 |
| 2018/0327148 A1 | 11/2018 | Trahan et al. | |

OTHER PUBLICATIONS

Savage, Valkyrie, et al., "Lamello: Passive Acoustic Sensing for Tangible Input Components", Apr. 18-23, 2015, 4 pgs., Adobe Research, UC Berkeley EECS, ACM 978-1-4503-4315, May 15, 2004; http://dx.doi.org/10.1145/2702123.2702207.

International Search Report and Written Opinion dated Apr. 12, 2019 for International Patent Application No. PCT/US2019/013291, 13 pages.

International Search Report and Written Opinion dated Feb. 3, 2020 for International Application No. PCT/US19/58826, Feb. 3, 2020, 13 pages.

* cited by examiner

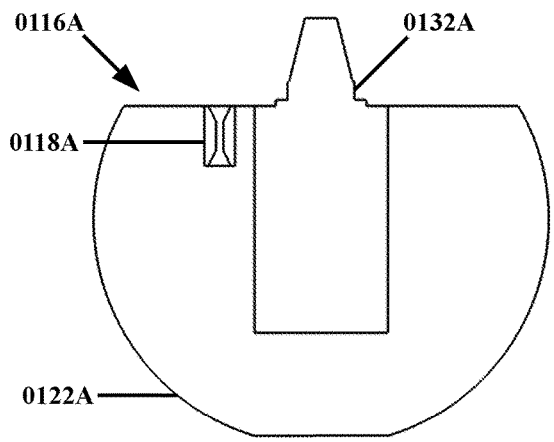
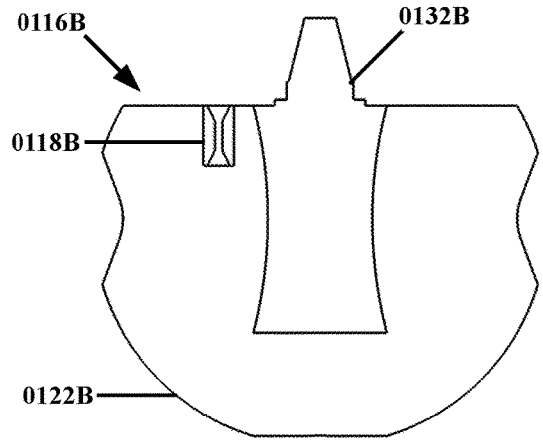
FIG. 1A
FIG. 1B
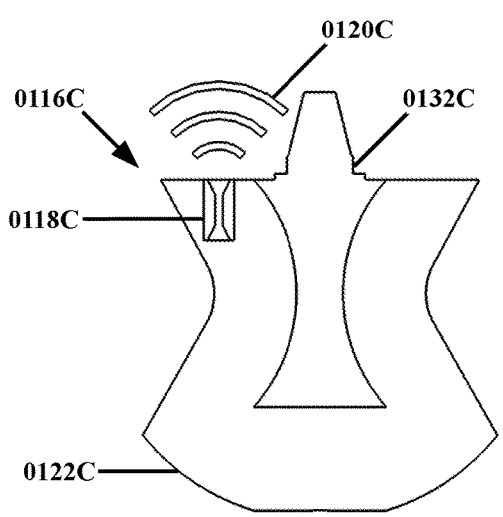
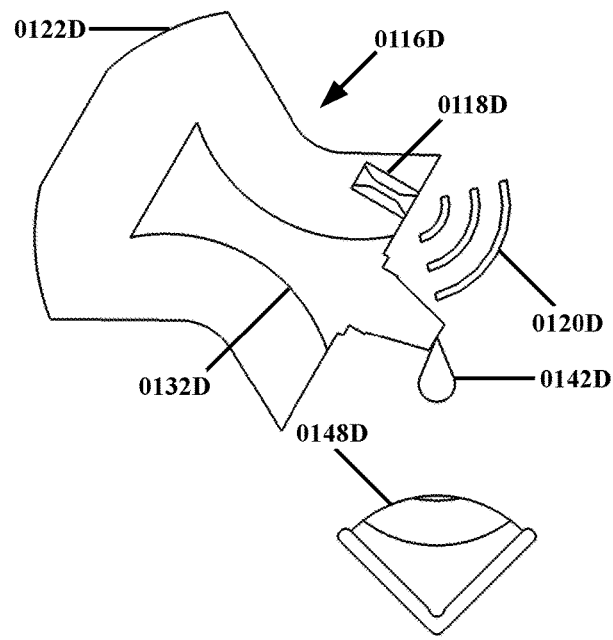
FIG. 1C
FIG. 1D

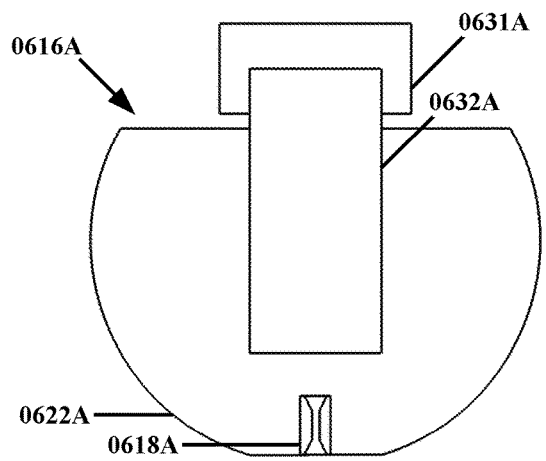
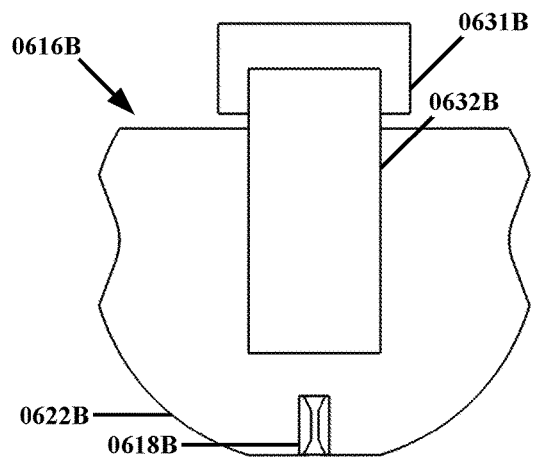
FIG. 6A
FIG. 6B
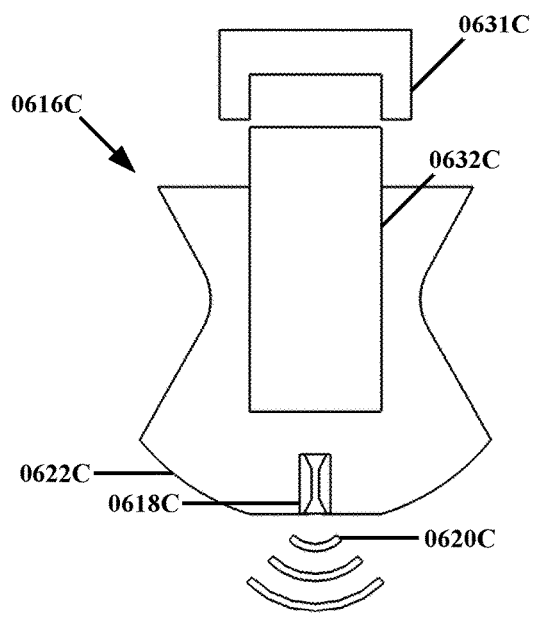
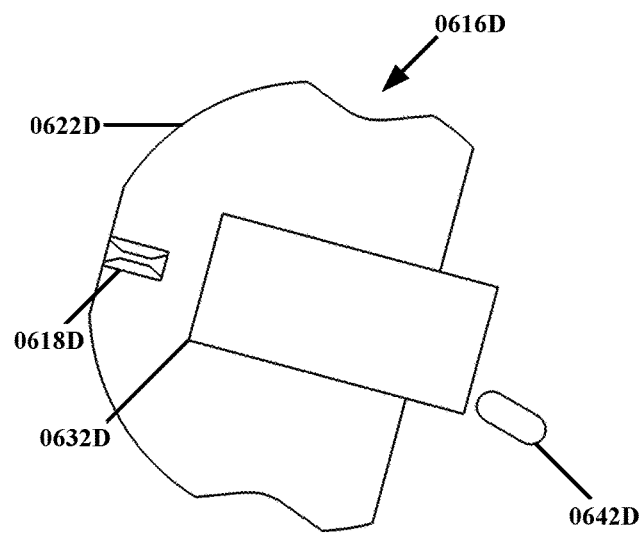
FIG. 6C
FIG. 6D

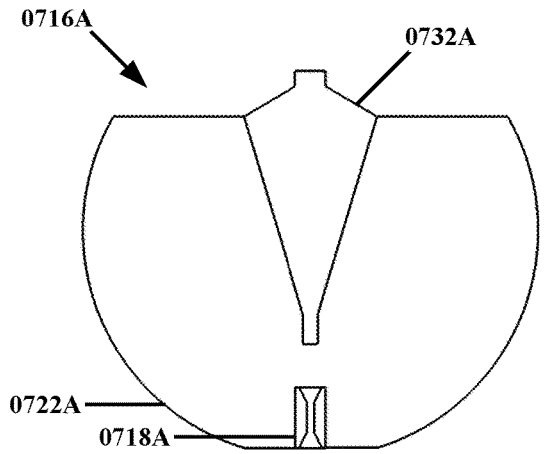
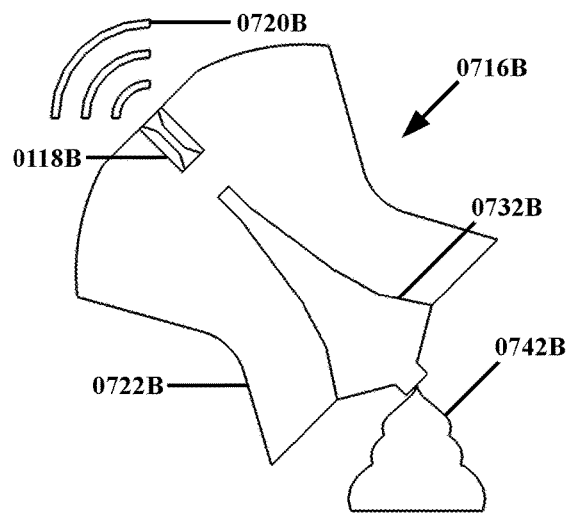
FIG. 7A
FIG. 7B
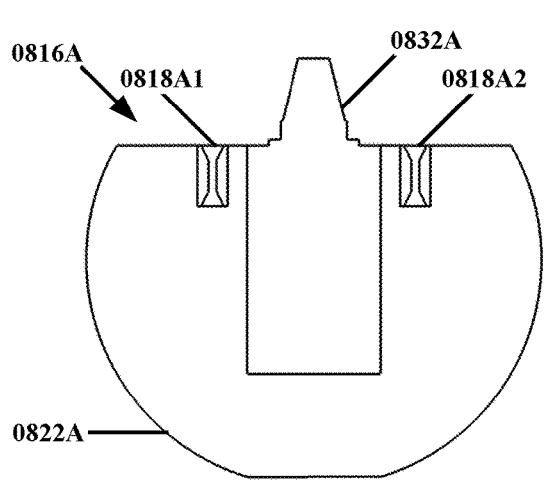
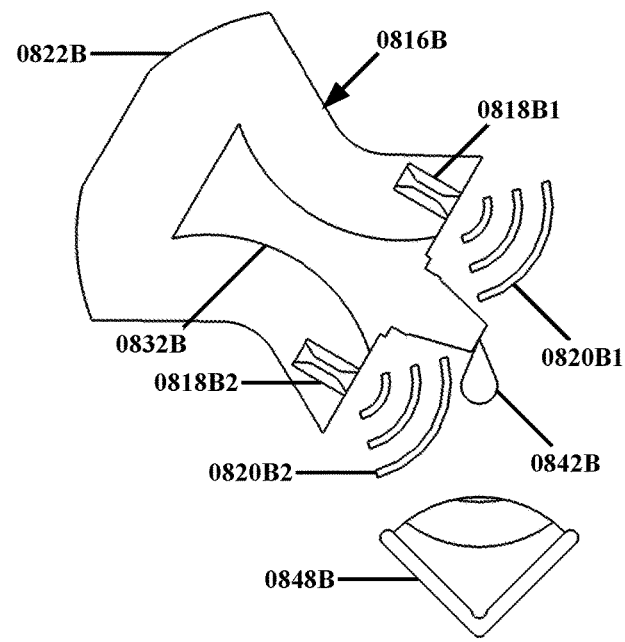
FIG. 8A
FIG. 8B

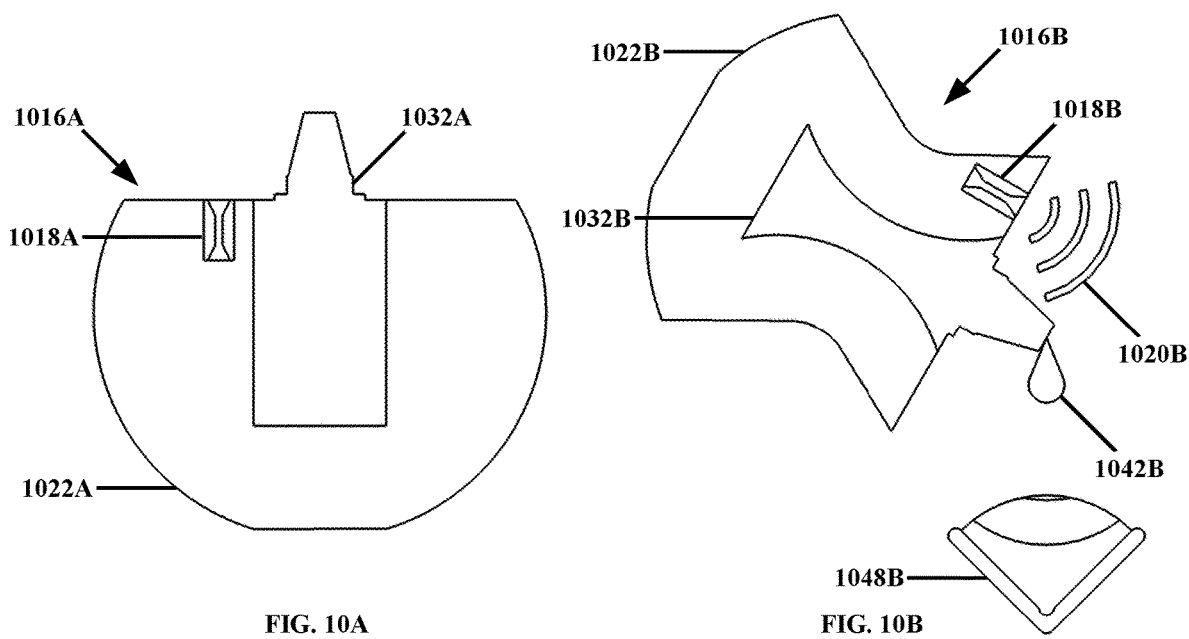
FIG. 10A
FIG. 10B
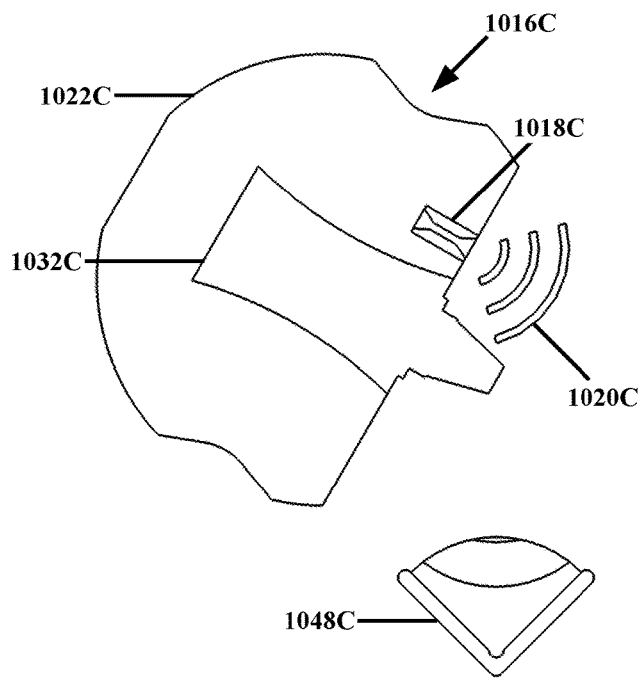
FIG. 10C

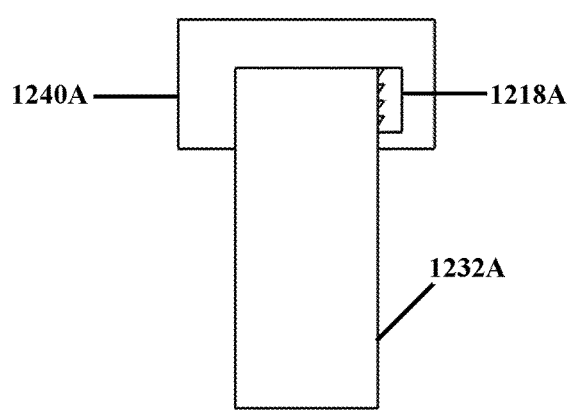
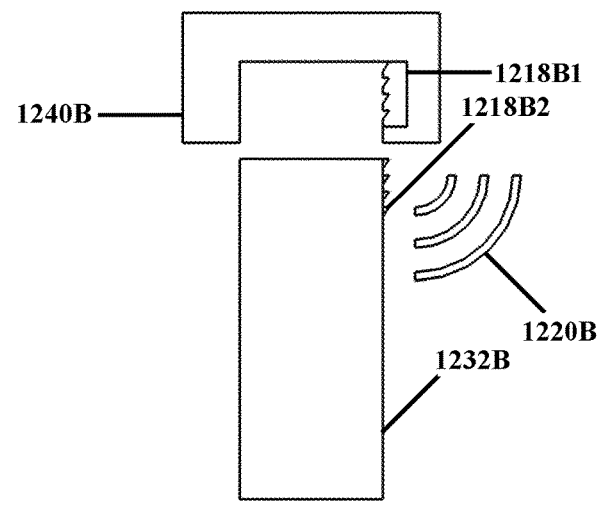
FIG. 12A  FIG. 12B
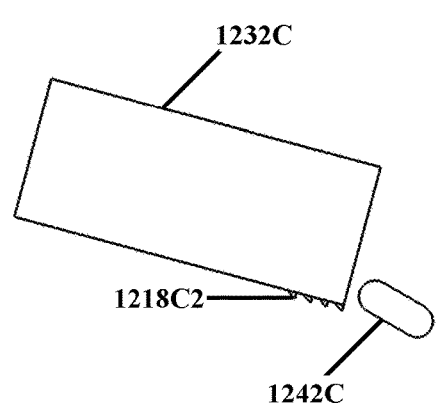
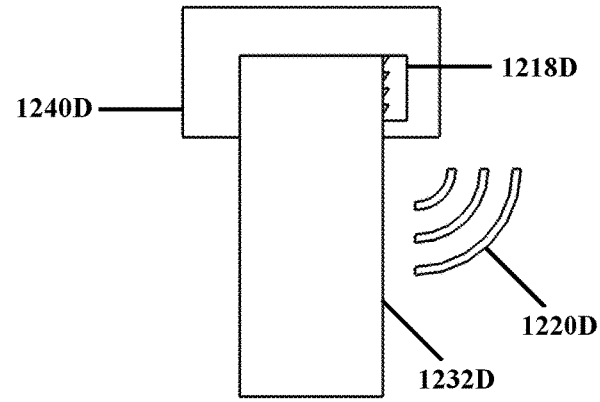
FIG. 12C  FIG. 12D

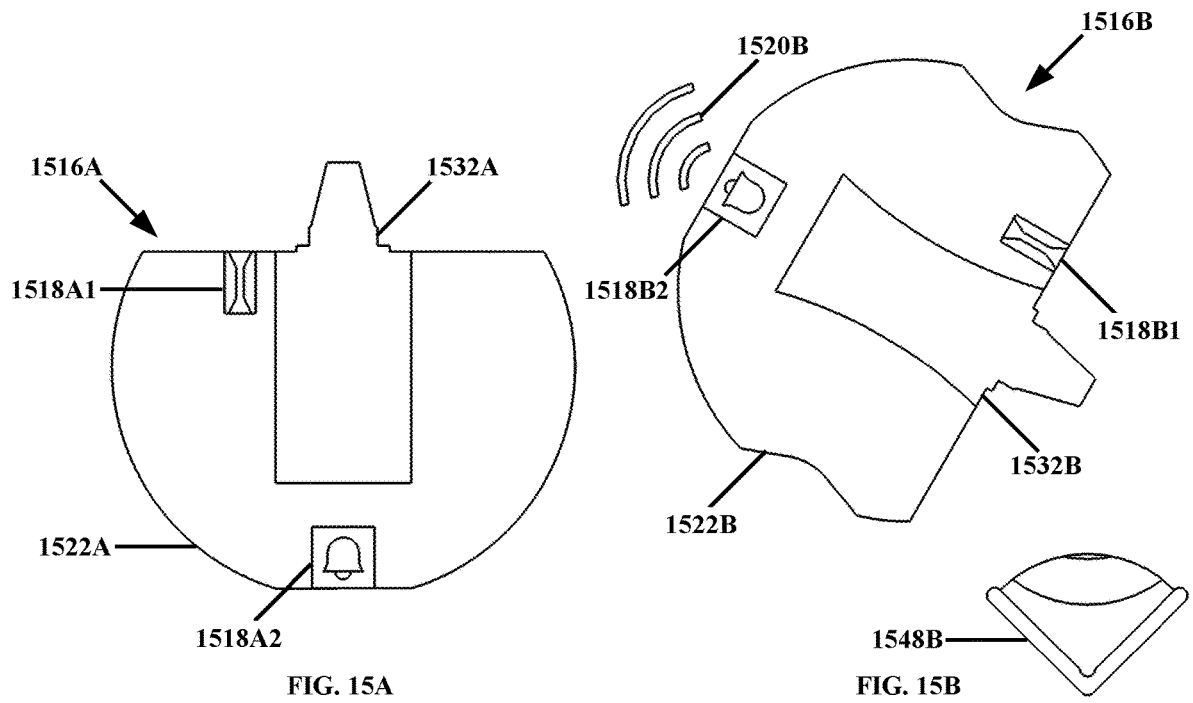
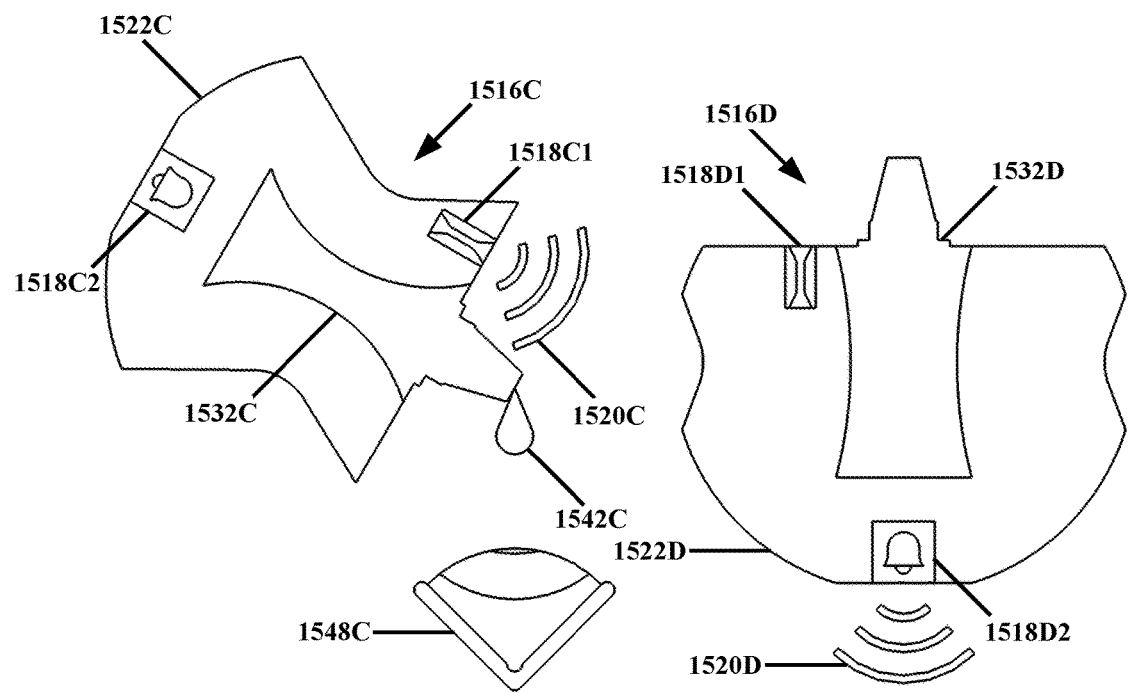
FIG. 15A  FIG. 15B  FIG. 15C  FIG. 15D

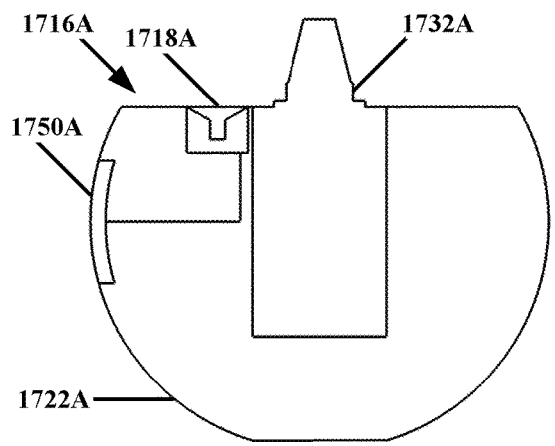
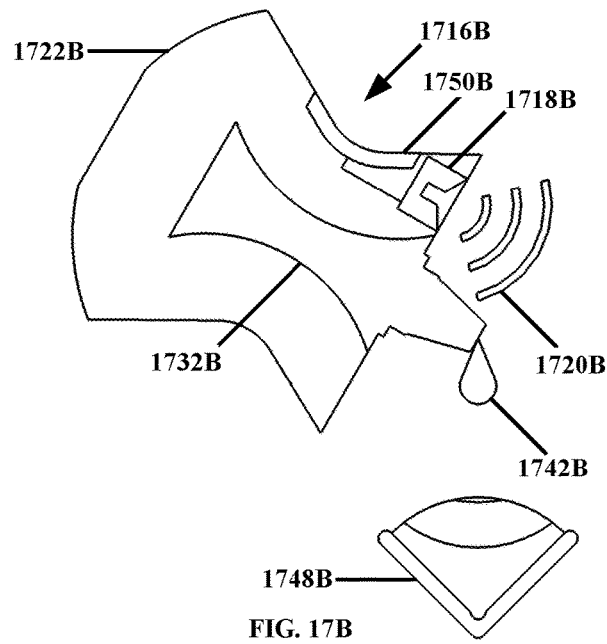
FIG. 17A  FIG. 17B
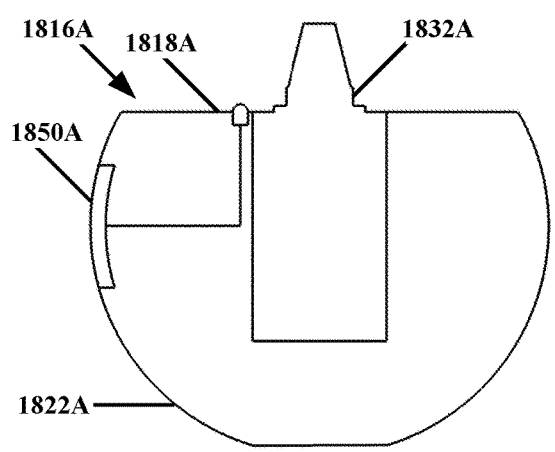
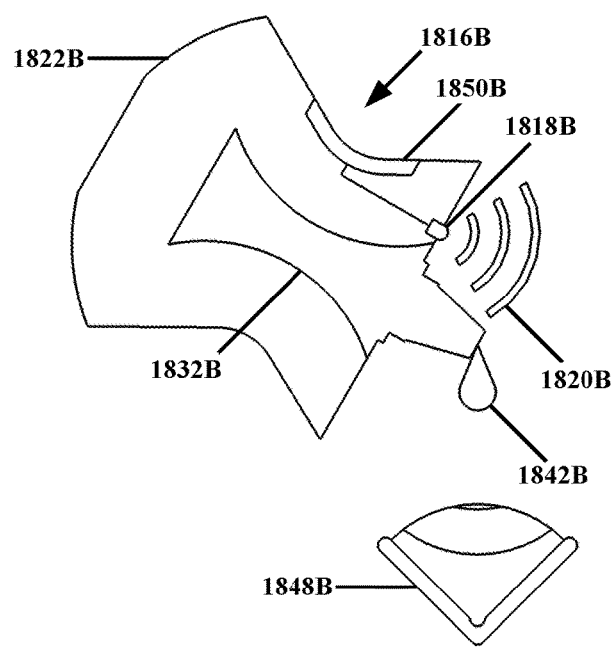
FIG. 18A  FIG. 18B

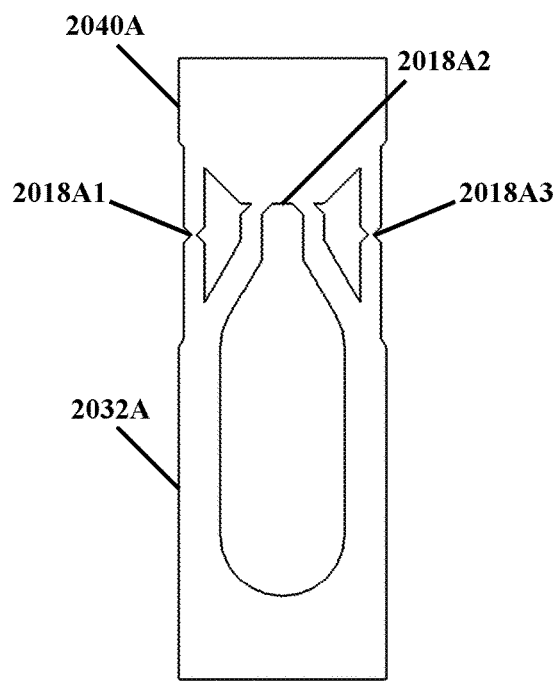
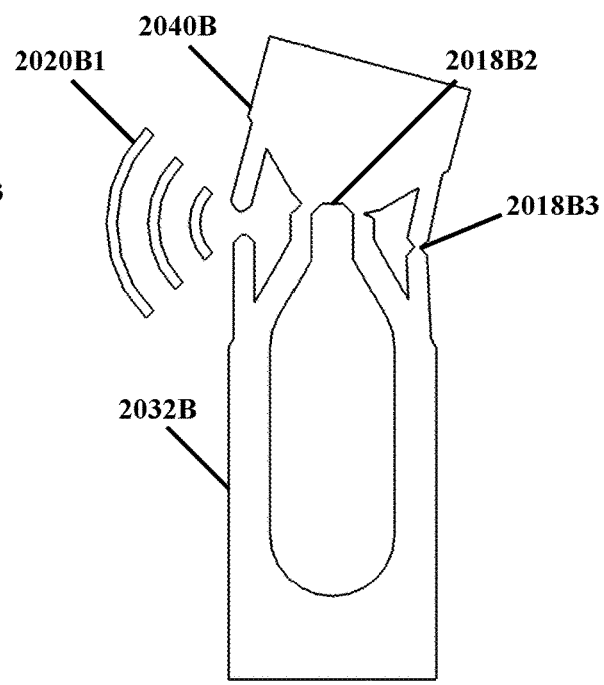
FIG. 20A
FIG. 20B
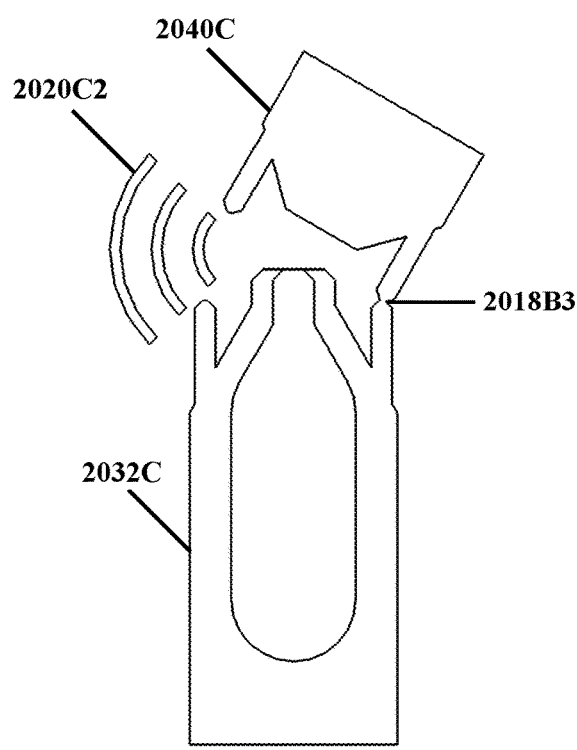
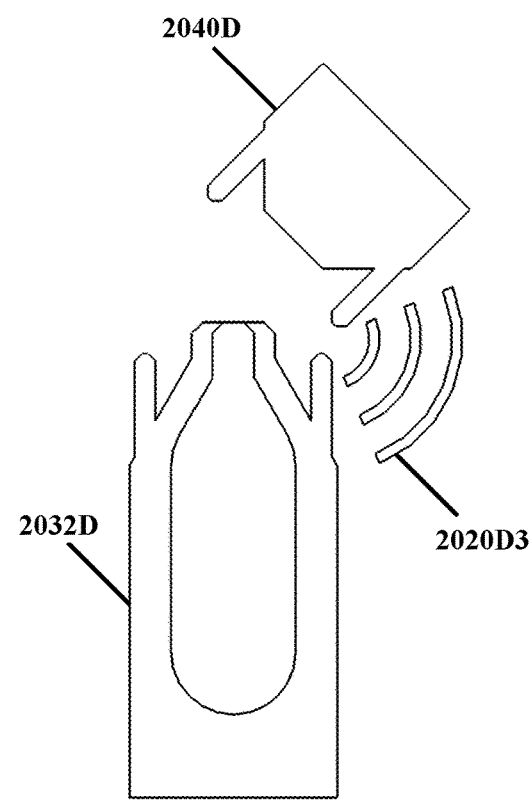
FIG. 20C
FIG. 20D

DETERMINING USE OF MEDICATION THROUGH CONSEQUENTIAL CHARACTERISTIC ACOUSTIC EMISSIONS

CROSS-REFERENCE TO RELATED APPLICATIONS

This application is a continuation application of U.S. patent application Ser. No. 15/885,681, entitled "DETERMINING USE OF MEDICATION THROUGH CONSEQUENTIAL CHARACTERISTIC ACOUSTIC EMISSIONS," and filed Jan. 31, 2018, which is incorporated by reference herein in its entirety.

FIELD OF THE INVENTION

Various embodiments concern acquisition of information indicating the use of medication. More particularly, various embodiments relate to providing a positive indication that medication is being taken, dispensed, prepared for use, etc., in a manner that does not require directed signaling action on the part of the user or an active (e.g., electrically powered) system for signaling, and that does not require "smart" functionality in/on the medication container itself.

BACKGROUND

A substantial portion of medications are not taken as prescribed. By some estimates, in clinical practice up to 50% or more of medications either may not be taken at all or may be taken with significant deviations from what is prescribed for the patient. For example, doses of a medication may be skipped, the medication may not be taken at the right intervals, at the right times, in the right dose, applied in the correct manner, etc. Such deviation from a prescribed medication regimen may be referred to broadly as "nonadherence". Nonadherence to prescribed medication regimens may have dramatic negative effects on health and/or healthcare costs, whether considering individuals or societies collectively.

Nonadherence may be even more common in clinical research, wherein some estimates indicate nonadherence of up to 70% or more. Nonadherence in a research context also presents other potential concerns. For example, testing of new medications typically may include efforts to determine the effectiveness of the medication, what side effects occur, how severe those side effects may be, in what fraction of the population those side effects occur, etc. Thus, nonadherence in a research setting may distort the basic understanding of a medication, e.g., if a medication is in fact highly effective if taken as prescribed but ineffective or dangerous if not taken properly, poor adherence within a clinical trial may result in data showing that the medication is not effective (when the actual problem is that it was not taken correctly).

One matter complicating issues related to nonadherence is that reliable data on the existence, degree, and form(s) of nonadherence present may be difficult to acquire. Whether for an individual, a larger population, or even a carefully selected and/or monitored group such as the subjects in a clinical trial, authentic data on how much nonadherence is taking place, among whom, and in what forms (e.g., missing doses, taking the medication incorrectly, etc.) may not be available through conventional sources. Typically, key information on adherence may be obtained by requiring deliberate action by the user, e.g., patients and/or test subjects may record and then report when a medication is taken, in what does, etc. However, patients and/or test subjects may not reliably perform such deliberate actions as recording or reporting medication use. Put bluntly, if individuals do not reliably take a medication, record and reports regarding the taking of that medication also may be unreliable. Thus, in practice it may not even be known how much nonadherence is taking place (beyond estimates), much less what the specific impacts of nonadherence may be in a given case, without authenticated data.

In addition, while at least in principle certain aspects of recording and/or reporting may be actively reported by an autonomous system, e.g., by incorporating electronic sensors into a medication container and storing or transmitting the data acquired, this too may present challenges in at least certain circumstances. For example, sensors typically require electrical power, and thus failing to charge or replace a battery may render such a system inoperable. Likewise, sensors and other electronics may be susceptible to damage from conditions as may be common to a medication container that is handled and/or carried regularly, e.g., the container may get wet, be dropped, be sat upon (for example if kept in a pocket), be exposed to extreme temperatures (for example if left in a car on a hot day or kept in an outer coat pocket in very cold weather), be bumped or compressed by other objects in a pocket or bag, etc. Damage from such conditions also may render an electronic system inoperable.

BRIEF SUMMARY OF THE INVENTION

This disclosure contemplates a variety of systems, apparatus, methods, and paradigms for targeted and/or interactive approaches for determining the use of medication through consequential characteristic acoustic emissions.

In one embodiment an apparatus is provided, including a remote with a flexible wall enclosing a volume of air, and a pneumatic whistle engaged with the wall and providing pneumatic communication between the interior of the wall and an exterior of the wall. The whistle is adapted to produce a characteristic acoustic emission having at least one ultrasonic pitch. The wall defines an aperture therein to accommodate an eye drop medication container, such that compressing the flexible wall compresses the aperture, compressing the aperture compresses the container, and compressing the container dispenses a medication. The apparatus includes a station that includes a smart phone, the smart phone including a digital processor, an electronic microphone adapted to receive the acoustic emission in communication with the processor, and a digital data store in communication with the processor. The processor is adapted to determine whether the acoustic emission is characteristic of the whistle, and to record in the data store that a drop of the medication has been dispensed from the container if the acoustic emission is determined to be characteristic of the whistle.

In another embodiment an apparatus is provided, including a remote adapted to engage a medication container, the remote including a purposed acoustic emitter adapted to emit a characteristic acoustic emission in user-transparent consequential response to a remote event. The apparatus includes a station, the station including a processor and a receiver in communication with the processor. The processor is adapted to determine whether the acoustic emission is characteristic of the acoustic emitter, and to register the remote event if the acoustic emission is determined to be characteristic of the acoustic emitter.

The remote may be adapted to removably engage the medication container.

The remote may define an aperture therein adapted to accept the container therein, such that compressing the body compresses the container so as to dispense a medication therefrom.

The acoustic emitter may include a whistle adapted to produce the characteristic acoustic emission when air is passed therethrough. The acoustic emitter may be adapted to produce an ultrasonic pitch as at least a portion of the characteristic acoustic emission. The acoustic emitter may be adapted to produce at least two pitches in combination as at least a portion of the characteristic acoustic emission. The acoustic emitter may be adapted to produce a characteristic acoustic wave form as at least a portion of the characteristic acoustic emission. The acoustic emitter may be adapted to produce a characteristic acoustic sequence as at least a portion of the characteristic acoustic emission.

The station may include a smart phone. The station may include a dedicated unit. The station may include a data store, a display, a communicator, and/or a user interface.

The processor may be adapted to determine and register supplemental remote event data, including the time of the remote event, an environmental condition associated with the remote event, a user condition associated with the remote event, and/or a property of the remote event. The remote event may include dispensing the medication from the container, and the supplemental remote event data may include the quantity of the medication dispensed.

In another embodiment a method is provided, including establishing a remote with a flexible wall enclosing a volume of air and a pneumatic whistle engaged with the wall and providing pneumatic communication between an interior of the wall and an exterior of the wall, with the whistle being adapted to produce a characteristic acoustic emission including at least one ultrasonic pitch, and the remote defining an aperture therein such that compressing the flexible wall compresses the aperture. The method includes disposing an eye drop medication container within the aperture of the remote, the eye drop medication container being adapted to contain and dispense an eye drop medication. The method also includes establishing a station including a smart phone, the smart phone including a processor, a microphone in communication with the processor, and a data store in communication with the processor, and compressing the flexible wall so as to compress the medication container disposed therein and cause a drop of the medication to be dispensed from the medication container, and to cause air to be expelled through the whistle from the interior of the wall to the exterior of the wall so as to produce the characteristic acoustic emission. The method further includes receiving the acoustic emission in the microphone, communicating the acoustic emission to the processor, and determining in the processor whether the acoustic emission is characteristic of the whistle, and recording the drop of medication being dispensed from the container in the data store if the acoustic emission is determined to be characteristic of the whistle.

In another embodiment a method is provided, including establishing a remote, the remote being adapted to engage with a medication container adapted to contain and dispense a medication, the remote including a purposed characteristic acoustic emitter engaged with the medication container. The method includes establishing a station including a processor and an acoustic receiver in communication with the processor. The method also includes, in transparent and direct response to a remote event, emitting from the acoustic emitter an acoustic emission, and includes receiving the acoustic emission in the acoustic receiver, communicating the acoustic emission to the processor, determining in the processor whether the acoustic emission is characteristic of the acoustic emitter, and registering the remote event in the processor if the acoustic emission is determined to be characteristic of the acoustic emitter.

The method may include determining supplemental remote event data in the processor, the supplemental remote event data including the time of the remote event, an environmental condition associated with the remote event, a user condition associated with the remote event, and a property of the remote event. The method may also include registering the supplemental remote event data if the acoustic emission is determined to be characteristic of the acoustic emitter.

The remote event may include dispensing the medication from the container, and the supplemental remote event data may include the quantity of the medication dispensed.

The station may include a smart phone, and establishing the station may include instantiating executable instructions on the smart phone. The station may include a dedicated unit, and establishing the station may include disposing the unit in a proximity of the remote.

The station may include a data store, a display, a communicator, and/or a user interface. Registering the remote event may include recording the remote event in the data store, outputting the remote event to the display, communicating the remote event to a recipient via the communicator, and/or accepting input regarding the remote event via the user interface.

BRIEF DESCRIPTION OF THE SEVERAL VIEWS OF THE DRAWINGS

Various objects, features, and characteristics will become more apparent to those skilled in the art from a study of the following Detailed Description in conjunction with the appended claims and drawings, all of which form a part of this specification. While the accompanying drawings include illustrations of various embodiments, the drawings are not intended to limit the claimed subject matter.

FIG. 1A through FIG. 1D depict an example remote and an example container adapted to dispense eye drops, in cross-section view.

FIG. 6A through FIG. 6D depict an example remote and an example container adapted to dispense pills, in cross-section view.

FIG. 7A and FIG. 7B depict an example remote and an example container adapted to ointment, in cross-section view.

FIG. 8A and FIG. 8B depict an example remote with two parallel emitters and an example container, in cross-section view.

FIG. 10A through FIG. 10C depict an example remote with an emitter operating in two functions and an example container, in cross-section view.

FIG. 12A through FIG. 12D depict an example emitter integrated with an example container, in cross-section view.

FIG. 15A through FIG. 15D depict an example remote adapted to indicate motion thereof and dispensing of medication from an example container, in cross-section view.

FIG. 17A and FIG. 17B depict an example remote with an electrical acoustic emitter and an example container, in cross-section view.

FIG. 18A and FIG. 18B depict an example remote with an electrical optical emitter and an example container, in cross-section view.

FIG. 20A through FIG. 20D depict another example of destructive acoustic emitters integrated with single-use container and executing in series, in cross-section view.

Figure 2A:
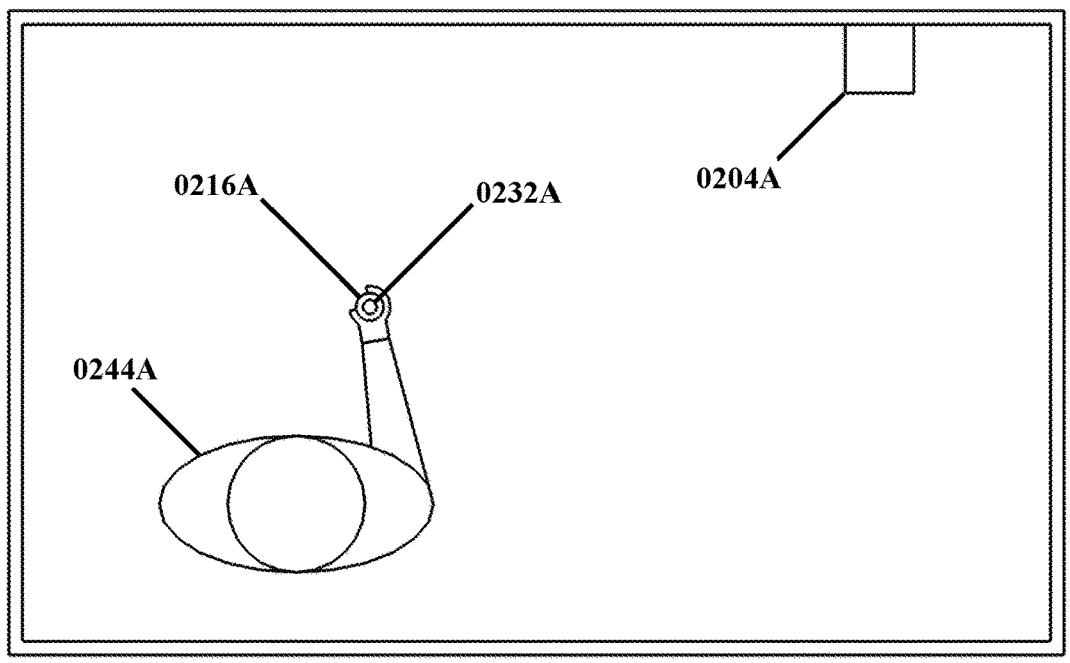
FIG. 2A and FIG. 2B depict an example station and an example remote as may be utilized by an individual, in top-down view.

The figures depict various embodiments described throughout the Detailed Description for the purposes of illustration only. While specific embodiments have been shown by way of example in the drawings and are described in detail below, the technology is amenable to various modifications and alternative forms. The intention is not to limit the technology to the particular embodiments described. Accordingly, the claimed subject matter is intended to cover all modifications, equivalents, and alternatives falling within the scope of the technology as defined by the appended claims.

DETAILED DESCRIPTION OF THE INVENTION

Various embodiments are described herein that relate to determining the use of a medication through transparent consequential characteristic emissions. Typically though not necessarily, embodiments may include a station adapted to detect and identify a characteristic acoustic emission (such as a musical pitch at a particular frequency), that acoustic emission being produced by a remote that is engaged or proximate to a medication container. The acoustic emission may be transparent, in that the user may not be required to take any particular action not already being performed in order to dispense or take the medication. The acoustic emission also may be consequential, in that actions performed to dispense or take the medication may produce the acoustic emission as a consequence thereof without (for example) requiring a user to make a choice, "arm" or activate an emitter, a processor to execute instructions, a secondary system to be activated, etc., in order to produce that acoustic emission. For example, the acoustic emission may be a purely mechanical consequence of dispensing medication (though other arrangements may be suitable). The acoustic emission also may be characteristic, in that the emission may be reliably recognizable as coming from the remote, distinct from background noise. In addition, the acoustic emission may be purposed, in that the remote may be configured specifically to produce the acoustic emission as a function that is not necessary to dispense the medication itself, rather than the emission being purely incidental from the operation of a type of container (for example, an unmodified "hiss" noise that an inhaler may produce expelling vapor with a puff of air).

It is noted that not all embodiments necessarily must exhibit all such features of emissions: transparent, consequential, characteristic, and purposed. Certain embodiments may not be fully user-transparent, for example, and/or other such features may not be present in all embodiments. In addition, even when present such features are not required to be absolute. For example, a characteristic acoustic emission may not be (and may not be required to be) absolutely unique, or perfectly identifiable. The presence of features and the degree to which each feature is present may vary from one embodiment to another, so long as the functionality described herein is enabled.

With reference now collectively to FIG. 1A through FIG. 3, aspects of structure and function of example arrangements for determining the dispensing and/or use of a medication are shown. As illustrated, a remote and a station cooperate in such determinations. The remote is adapted to purposefully produce a characteristic acoustic emission in user-transparent and consequential response to some action associated with taking a medication; for example, a characteristic whistle pitch may be emitted by the remote as an eyedrop is dispensed. The station then receives that acoustic emission, and registers a medication-associated event as having taken place based on that acoustic emission.

More particularly, with reference now to FIG. 1A through FIG. 1D, therein is shown an example remote and arrangements for producing an acoustic emission, illustrated in cross-section view.

In FIG. 1A, a remote 0116A is shown. The remote 0116A is shown as approximately spherical in shape, truncated at top and bottom. The example remote 0116A shown includes a wall 0122A enclosing an interior containing a volume of air. In addition, the remote 0116A includes an acoustic emitter 0118A. In the example shown the acoustic emitter 0118A is in the form of a whistle, enabling airflow through the acoustic emitter 0118A between the interior of the remote 0116A and the environment surrounding the remote 0116A. In addition, the remote 0116A has a container 0132A engaged therewith, shown disposed within an aperture of the remote 0116A. It is noted that the container 0132A may not necessarily be considered part of the remote 0116A; while a remote 0116A that includes a container 0132A as a component thereof (e.g., rather than accommodating a container therein, otherwise engaging with a container, etc.) is not prohibited, neither is such required.

Turning to FIG. 1B, an arrangement at least somewhat similar to that in FIG. 1A is shown. A remote 0116B with a wall 0122B and an acoustic emitter 0118B is shown, with a container 0132B engaged therewith. However, in FIG. 1B the wall 0122B of the remote 0116B is slightly indented to either side. Typically, though not necessarily, such indentation may be a result of compression applied to the remote 0116B. The wall 0122B of the remote 0116B may be flexible so as to readily deform and return to an original shape.

In addition, attention is drawn to the shape of the container 0132B. Given a remote 0116B having a flexible wall 0122B with air enclosed therein, when pressure is applied to the remote 0116B at least some of that pressure may be transmitted to the container 0132B disposed within the remote 0116B. Thus, if the container 0132B is flexible the container 0132B also may deform to some degree. (The degree of deformation as shown is explanatory, and is not necessarily intended to reflect a real physical system; actual deformation of a flexible wall 0116B and/or a flexible container 0132B may be extremely complex, and the particulars of such deformations are not limiting.)

Moving on to FIG. 1C, again an arrangement at least somewhat similar to that in FIG. 1A and FIG. 1B is shown, with a remote 0116C having a wall 0122C and an acoustic emitter 0118C, and a container 0132C engaged therewith. However, as may be seen in FIG. 1C the wall 0122C is more extensively deformed than in FIG. 1B; the sides of the wall 0122C are visibly deeply indented. Likewise, the sides of the container 0132C are also deeply indented.

Given such deformation of the remote 0116C as shown in FIG. 1C, the volume available for air inside the wall 0122C may be reduced. Consequently, air may be communicated from inside the wall 0122C to the outside environment via the acoustic emitter 0118C. For an acoustic emitter 0118C in the form of a whistle as shown in FIG. 1C, such flow of air may cause the acoustic emitter 0118C to produce an acoustic emission 0120C (shown as radiating wave fronts for explanatory purposes; in practice acoustic emissions may not be visible). In more colloquial terms, the whistle may make a pitch if the remote 0116C is squeezed, e.g., by a user's hand.

In addition, given such deformation of the container 0132C as shown in FIG. 1C, the volume inside the container 0132C likewise may be reduced. Consequently, depending on the orientation of the container 0132C, the amount of material (if any) contained therein, etc., some of the contents of the container 0132C may be expelled. No such expelled contents are shown in FIG. 1C; given the vertical orientation of the container 0132C, and the depiction of the container 0132C as a squeeze bottle (such as an eye drop bottle), contents thereof may not necessarily be expelled.

However, in FIG. 1D an arrangement at least somewhat similar arrangement is shown that does include expelled contents of a container. As may be seen, the remote 0116D shown therein has a wall 0122D and an acoustic emitter 0118D, and a container 0132D is engaged therewith. The wall 0122D is again deeply indented, and the sides of the container 0132D also are also deeply indented. However, in the arrangement shown in FIG. 1D, the remote 0116D and the container 0132D engaged therewith are inclined approximately 135 degrees from vertical. In addition, the remote 0116D is positioned such that the nozzle of the container 0132D is disposed over the eye 0148D of a user.

Consequently, as the remote 0116D is compressed, container 0132D also is compressed, and a dispersal 0142D of medication (shown in the form of a droplet of liquid) is dispensed from the container 0132D; given the relative disposition of container 132D and eye 0148D, it may be anticipated that the medication will fall into the eye 0148D. In addition, as in FIG. 1C the compression of the remote 0116D has reduced the volume within the wall 0122D, and air passing through the acoustic emitter 0118D has produced an acoustic emission 0120D. To again use colloquial terms, as the remote is squeezed to dispense medication, and because the remote is so squeezed, the whistle sounds. (It is noted that, for an eyedrop bottle, it may not be typical to squeeze the container while in a vertical orientation. The orientation of the remote and container in FIG. 1C is shown as an example illustrating acoustic emission, rather than implying that FIG. 1C is necessarily part of a rigid sequence of events in dispensing medication.)

Several aspects of such an arrangement may be worthy of further description and/or emphasis.

First, it is noted that the acoustic emission 0120D in FIG. 1D is purposed, rather than incidental. For example, the acoustic emission 0120D under consideration in FIG. 1D is one that is produced deliberately, through the addition of an air bladder and a whistle. This may be understood as distinct from sounds that may be incidental, such as the sound of a container being compressed, of a droplet landing in a user's eye, etc. The acoustic emission 0120D in FIG. 1D is an additional noise that is produced deliberately and with purpose (and, as will be explained in greater detail subsequently herein, with a particular function), rather than being an environmental noise.

Second, given that the acoustic emission 0120D is produced on purpose, e.g., by providing the acoustic emitter 0118D in the remote 0116D and engaging the remote 0116D with the container 0132D, the nature of the acoustic emission 0120D may be selected. The acoustic emission 0120D thus may be characteristic, that is, may exhibit properties that render the acoustic emission 0120D readily identifiable. For example, the acoustic emitter 0118D may produce a whistle pitch at a particular frequency and/or volume, two or more frequencies together, etc. By selection of such properties, the acoustic emission 0120D may be recognizable from background noise, and/or unlikely to be mistaken for other sounds.

Third, production of the acoustic emission 0120D may be understood to be a consequential result of dispensing the droplet 0142D of medication. That is, it may not be necessary for the squeeze to be detected with a sensor, or for such a sensor or a processor to activate an electrical system that generates sound, etc. Rather, squeezing the remote 0116D causes the acoustic emission 0120D as a consequence of the squeeze, without other active intervention. Such an arrangement may also be described as in some sense "passive", in that the act of dispensing the medication (e.g., squeezing the remote) in itself causes a characteristic sound to be produced. However, as action typically may be taking place—e.g., an acoustic emission may be produced—the term "consequential" typically is used herein.

Fourth, the production of the acoustic emission 0120D also may be viewed as transparent from the perspective of a user of the medication. That is, the user may not be required to take an additional action beyond dispensing the medication in order to produce the acoustic emission 0120D. In the example of FIG. 1D, squeezing the remote 0116D to dispense a droplet 0142D produces the acoustic emission 0120D without other conscious action by the user when attempting to use the medication. (And as described subsequently herein, that acoustic emission 0120D then may cause the use of the medication to also be registered without additional conscious action by the user.) Thus, the user may not be required to consciously activate the acoustic emitter 0118, or to document the use of the medication, inform or report that the medication was used, etc.

Turning now to FIG. 2A, a remote 0216A is shown with a container 0232A engaged therewith. The remote 0216A is shown to be in the hand of a user 0244A, within some enclosed space (not numbered). In addition, a station 0204A is shown at some distance from the user 0244A and the remote 0216A.

As noted previously with regard to FIG. 1A through FIG. 1D, a remote 0216A such as is shown in FIG. 2A may produce an acoustic emission as the remote 0216A is manipulated in a manner associated with dispensing a medication, e.g., squeezing the remote 0216A to squeeze the container 0232A so as to dispense medication may activate a whistle.

Figure 2B:
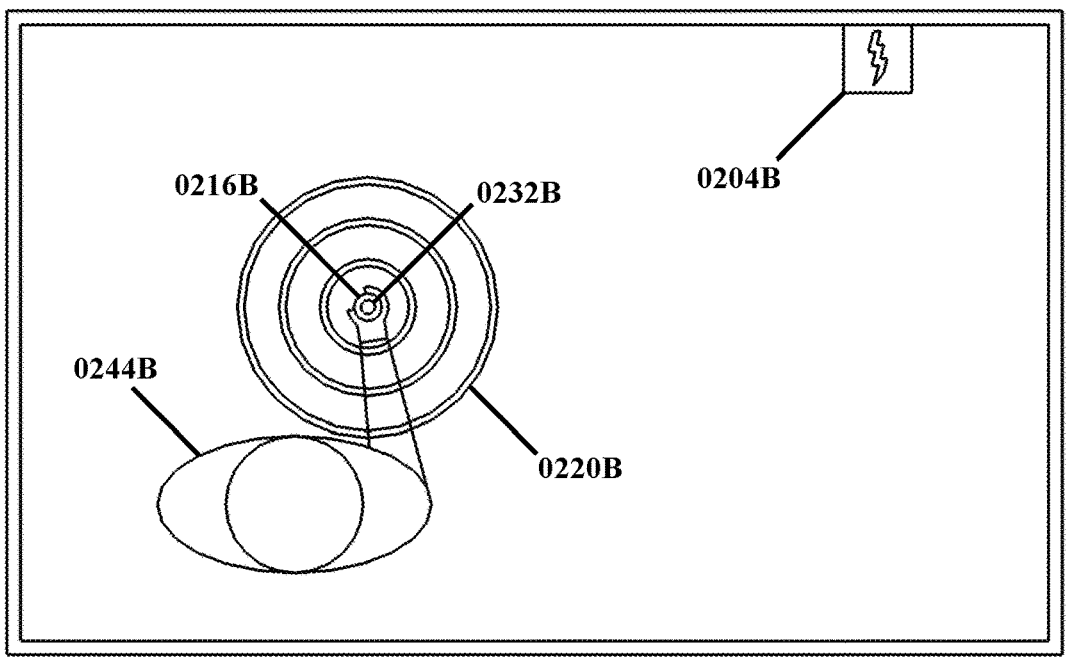

Turning to FIG. 2B, a circumstance is shown wherein such an acoustic emission is produced. At least somewhat similarly to FIG. 2A, the arrangement in FIG. 2B shows a remote 0216B in the hand of a user 0244B, and a container 0232B engaged with the remote 0216B. A station 0204B also is shown. In addition, the remote 0216B is depicted to be producing an acoustic emission 0220B (an acoustic emitter is not individually illustrated) radiating from the remote 0216B. The station 0204B is also shown to be active (indicated by the lightning bolt). More regarding stations and activation thereof is described subsequently herein, however typically the station 0204B may be understood as receiving the acoustic emission 0220B, e.g., with a microphone or similar receiver.

Thus, in the arrangement of FIG. 2B, the remote 0216B produces an acoustic emission 0220B in a transparent and consquential response to an event associated with dispensing medication from the container 0232B; and the station 0204B receives that acoustic emitter.

It is noted that the body position of the user 0244B in FIG. 2B—standing with hand partially extended and holding the remote 0216B and container 0232B—may not correspond with a typical body position for dispensing an eye drop (e.g., with the head tilted back and the bottle inclined over an eye). This is deliberate, so as to emphasize that embodiments are not limited only to eye drops or to any particular medication, and that events producing an acoustic emission 0220B are not limited only to dispensing the medication. For example, pills, ointments, etc. also may be so dispensed, from bottles, squeeze tubes, etc. Likewise, acoustic emissions may be triggered by contextual events that are not dispensing actions themselves but are otherwise associated with dispensing medication. For example, removing the cap of a container, shaking a bottle to mix a medication, etc. may trigger an acoustic emission. While removing the cap of a medication container may not constitute taking the medication, removing the cap still may be associated with taking the medication, and thus an acoustic emission upon removing the cap may be indicative that a medication has been taken.

Thus, while perhaps not typical for dispensing an eye drop, the body position in FIG. 2B may be suitable for at least some such actions.

Figure 3:
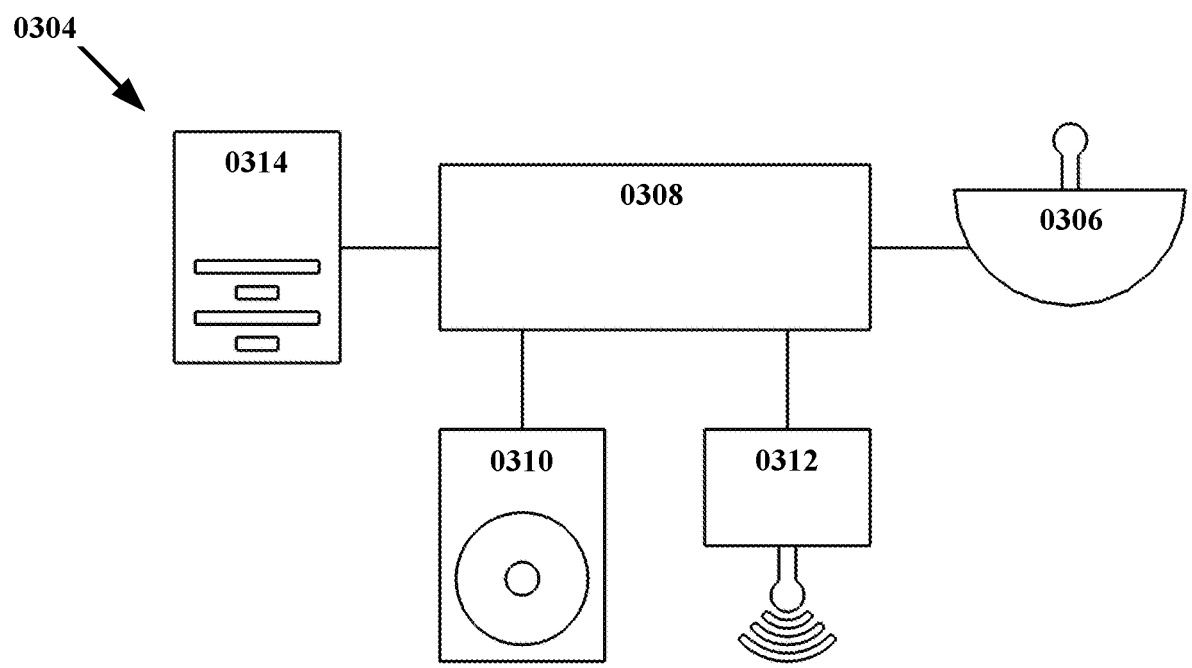
FIG. 3 depicts an example station, in schematic view.

Moving on to FIG. 3, a schematic of an example station 0304 is shown therein. The station 0304 includes an acoustic receiver 0306, adapted to receive acoustic emissions. A processor 0308 is in communication with the receiver 0306. A power supply 0314 is also shown, along with a data store 0310 adapted to store information, and a communicator 0312 adapted to communicate (e.g., send and/or receive) information with some external entity. It is noted that not all elements will necessarily be present in all embodiments, and that embodiments may exhibit other elements and/or other configurations. For example, it may not be necessary to communicate the data externally if the data may be stored, thus if a data store 0310 is present a communicator 0312 may not be present (or vice versa), etc.

So long as the station 0304 is capable of performing the necessary functions, the particulars thereof are not limited. Likewise, substantially any device and/or group of devices providing adequate functional capabilities may be suitable. For example, certain electronic devices such as desktop computers, laptop computers, tablets, smart phones, other smart devices, etc. may include a microphone and processor (and/or other elements such as a power supply, data store, communicator, etc.). Thus for at least certain embodiments a smart phone may serve as a station 0304. Typically, though not necessarily, executable instructions may be instantiated onto a processor in a smart phone or other device so employed, so as to support certain functions described herein. Use of a smart phone or other portable electronic device may exhibit certain advantages, for example in that a user may already have a smart phone and routinely keep their smart phone nearby. However, use of a dedicated station 0304 also may be suitable. Dedicated stations also may exhibit certain advantages. For example, a unit adapted to plug in to a wall socket also may not be subject to issues regarding low battery, etc.

A given remote and station are not necessarily required to be engaged in a one-to-one correspondence. That is, a single remote may be used in cooperation with multiple stations, and/or a single station may be used in cooperation with multiple remotes. Thus, for example, a user may have remotes for several different medications, all of which cooperate with the user's smart phone as a station. Conversely, a user may have receivers in several rooms of a dwelling (or other space), so that acoustic emissions may be received no matter where the user is in that dwelling.

More description regarding functions of individual elements in a station 0304 such as is shown in FIG. 3 is presented below.

Figure 4:
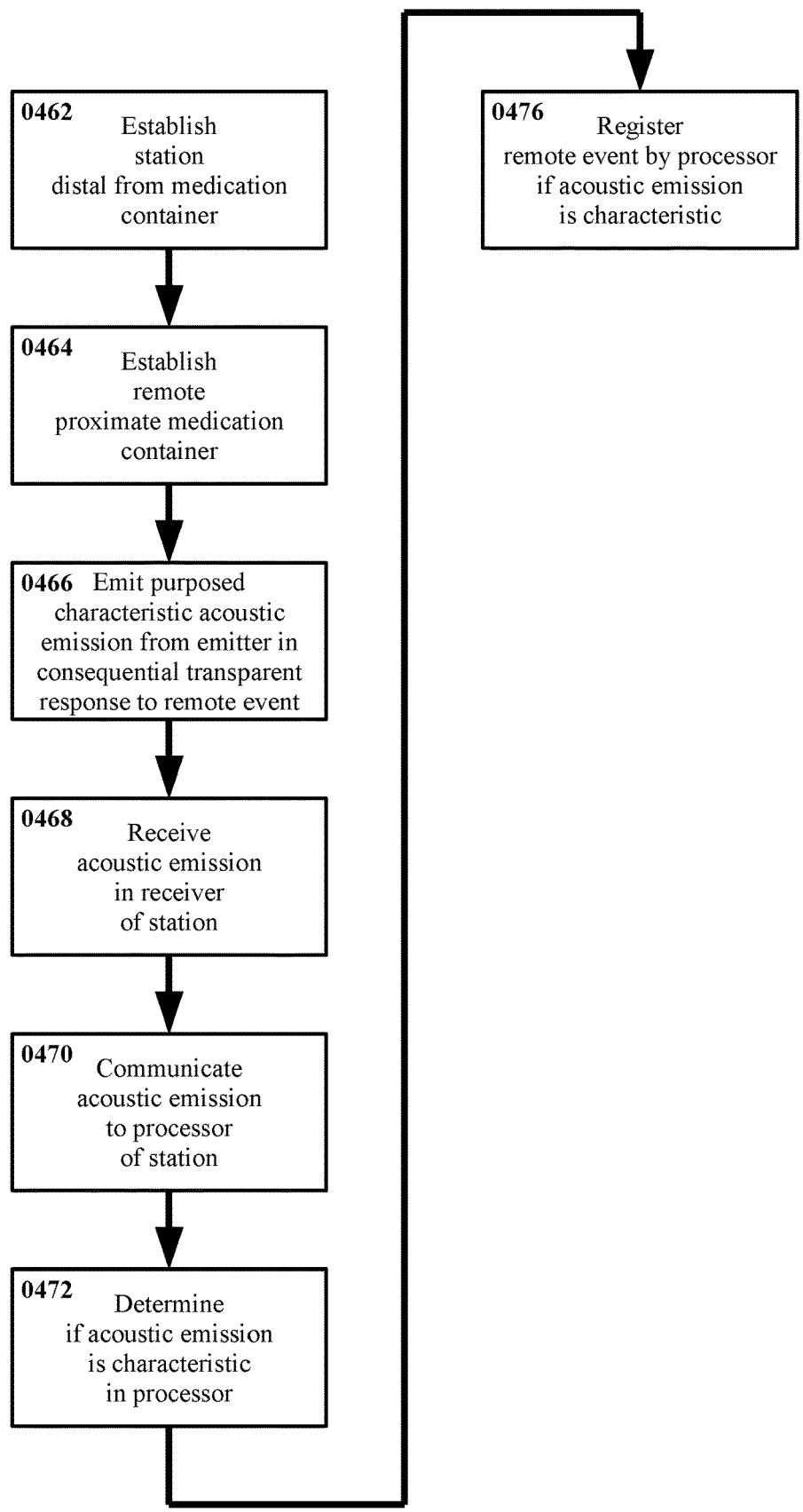
FIG. 4 depicts an example method for determining the use of a medication through transparent consequential characteristic emissions, in flow chart form.

Now with regard to FIG. 4, an example method for determining use of medication through transparent and consequential response to a remote event associated with dispensing said medication is illustrated, in flow chart form.

In the method of FIG. 4, a station is established 0462 at some location distal from a medication container. The physical distance is not limited and may vary not just for different embodiments but also over time for a particular embodiment, however typically (though not necessarily) the station may be sufficiently distant from the medication container as to not be in physical contact therewith.

A remote is established 0464 at some location proximate the medication container. Again, the physical distance is not limited, but typically (though not necessarily) the remote may be physically engaged with the medication container. For example, the medication container may be disposed within the remote, physically coupled to the remote, etc.

In a consequential and transparent response to some event affecting the remote and in association with dispensing medication, a purposed characteristic acoustic emission is emitted 0466 from the remote. For example, as described with regard to FIG. 1A through FIG. 2 a sound such as a whistle may be produced by squeezing the remote in order to expel medication from the container. The acoustic emission may be emitted 0466 as a direct result of dispensing the medication. However, as noted previously remote events (that is, events relating to the remote in some manner) that are contextual to dispensing medication also may be suitable for consideration. The acoustic emission also may be emitted 0466 in a manner that is user-transparent.

Still with reference to FIG. 4, the acoustic emission is received 0468 in the receiver of the station. For example, a microphone in a smart phone may pick up a whistle emitted from a remote. The acoustic emission (or some electronic signal representing the acoustic emission, etc.) is communicated 0470 to the processor of the station. Within the processor, a determination is made 0472 as to whether the acoustic emission that has been received (in step 0468) is indeed characteristic of the remote. A given acoustic receiver may receive numerous sounds, including but not limited to ambient noise, conversation, music being played nearby, etc. As noted, the acoustic emission emitted 0466 by the remote is in some manner characteristic, e.g., with a particular pitch or combination of pitches, etc. Thus the processor may determine 0472, for example by comparing a received sound against some standard instantiated onto the processor, whether a given sound is or is not the acoustic emission from a remote.

If the acoustic emission is determined 0472 to be characteristic of the remote, then a remote event is registered 0476 by the processor. That is, if the processor determines that the remote has made its characteristic sound, it is considered that whatever event causing that sound to be made has taken place. If the event in question is dispensing medication, then it is considered that the medication has been dispensed. If the event in question is contextual, such as removing the cap of a container, then it is considered that the cap has been removed. Further conclusions also may be determined in certain embodiments, e.g., it may be determined that if the cap has been removed, the medication also has been dispensed. Such determinations may be absolute, e.g., yes or no, or may be associated with some confidence value, e.g., high confidence, 92% confidence, class I confidence, etc.

How the event is registered 0476 is not limited. The event may be flagged for transmission to some other entity (a database, another processor, a human monitor, etc.), may be flagged for storage in a data store (such as a hard drive, solid state drive, etc.), or otherwise noted in some fashion. In addition, the precise information that may be registered 0476 is not otherwise limited. Information may be as minimal as the fact that the event was detected to have occurred (that is, that the sound was received and identified), but may also include other information. For example, the time that an event was identified as having occurred may be registered (whether with the fact of the event explicit or implicit in there being a time of occurrence), and/or may include other information such as confidence of identification of the acoustic emission, confidence that a contextual event corresponds with the medication being dispensed, the characteristic sound itself, identifying information such as an ID for the processor, station as a whole, remote, etc., patient name or reference number, the type/dose of medication, etc.

What, if anything, is done if a sound is received but not determined to be the characteristic acoustic emission of the remote is not limited. In certain instances, such sounds also may be registered in some manner, e.g., as non-characteristic sounds that may be safely excluded from consideration, as potentially characteristic but with low confidence, etc. However, in other instances it may be suitable simply to ignore non-characteristic sounds and take no action in response.

Figure 5:
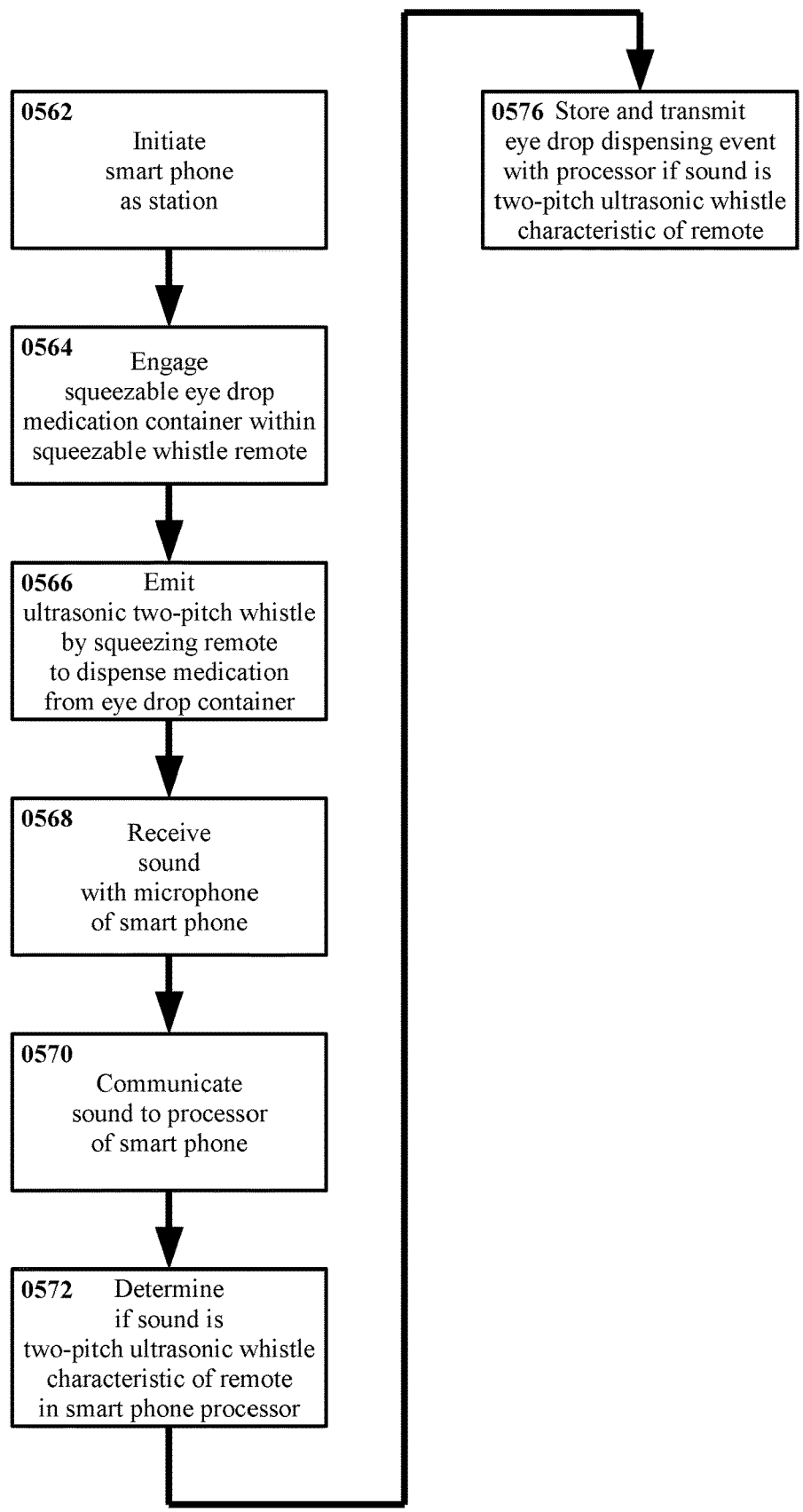
FIG. 5 depicts another example method for determining the use of a medication through transparent consequential characteristic emissions, with concrete reference to a squeezable whistling remote and a smart phone as a station, in flow chart form.

Moving on to FIG. 5, for clarity a highly concrete example method is presented that may be similar to that in FIG. 4 but that is also a more specific embodiment. Namely, the method in FIG. 5 refers to an arrangement using a squeezable remote and a squeezable eye drop container disposed therein such as illustrated in FIG. 1A through FIG. 1D, an eye drop medication, and a smart phone serving as a station. It is emphasized that such particulars are examples only, and are not limiting.

In the method of FIG. 5, a smart phone is initiated 0562 as a station. For example, executable instructions and/or data may be instantiated onto the processor of the smart phone. As a more colloquial example, a medication tracking application or "app" may be loaded onto the phone. Alternately, such an app (and/or other instructions/data) may already be present on the smart phone (e.g., having been previously installed as part of a package of basic software), in which case initiation may simply be running the app or similar.

Continuing in FIG. 5, a squeezable eye drop container is engaged 0564 within a squeezable whistle remote. For example, as shown in FIG. 1A through FIG. 1D the remote may be a flexible, roughly spheroid air-filled body with a whistle incorporated therein, and defining an aperture to accept a medication container therein.

The remote emits 0566 an ultrasonic two-pitch whistle, wherein the two pitches are at specific frequencies. Thus, for this example, as the remote is squeezed the container also is squeezed; when an eye drop is to be dispensed, the remote is squeezed so as to squeeze the container. However, so squeezing the remote also causes air to pass through the whistle, the whistle being configured to produce the two ultrasonic pitches. (In practice the "whistle" may not be singular, rather two distinct mechanisms may each produce one pitch. Embodiments are not limited in this regard.) Such an acoustic emission may be considered characteristic, in that the number of phenomena that may simultaneously produce two specific pitches in the ultrasonic range may be small, and consequently detecting that particular combination of pitches may be treated as a reliable indication that the sound is coming from the remote.

A sound is received 0568 with the microphone of the smart phone that is serving as a station in the example of FIG. 5. The sound may be the acoustic emission, in this example the ultrasonic two-pitch whistle, but other sounds may be received by the microphone. The sound is communicated 0570 to the processor of the smart phone. Although the sound is referred to as being communicated, processed, etc., it is noted that sound itself may not literally be communicated or otherwise manipulated; rather, the microphone in receiving 0568 the sound may generate an electronic signal therefrom, with this signal or some portion thereof then being communicated to the processor, processed therein, etc.

In the processor of the smart phone, a determination is made 0572 as to whether the sound in question is characteristic of the remote. In the example of FIG. 5, this may include a determination of such factors as to whether two pitches are present, whether each pitch is of the proper frequency, whether the waveforms of the pitches correspond with what may be expected for a whistle (as opposed to, for example, pitches generated electronically, pitches generated by vibrations of a string, etc.), whether the two pitches were received (thus presumably produced) at approximately the same time, etc. The factors that may be considered are not limited.

If the sound in question is determined 0572 to be the two-pitch ultrasonic whistle characteristic of the remote, an eyedrop dispensing event (that is, that the medication in the container has been dispensed) is recorded 0576 in a data store by the processor, and is also transmitted 0576 to some external entity by the processor. Thus, in this instance, registration of the event corresponds to both storing and communicating the event.

It is again emphasized that the arrangements in FIG. 5 are an example only, and while the particulars therein are presented for clarity those particulars do not limit embodiments. For example, medication containers may be other than eye drop bottles, including but not limited to other squeeze bottles, boxes or tubes such as may dispense pills, tubes as may dispense ointments, hypodermic syringes as may dispense injectable medications, shakers as may dispense powders, etc. Indeed, in certain embodiments the container may not contain a medication at all, but rather some other material to be dispensed. Also, at least in principle other non-medication actions may be signaled similarly, e.g., use of a device for physical therapy may be configured similarly with a remote so as to produce whistles or other acoustic emissions in a fashion similar to the remotes shown in FIG. 1A through FIG. 1D.

Likewise, the type(s) of medication (and/or other materials) as may be dispensed is not limited. The acoustic emissions are not limited, and may vary considerably. While ultrasonic emissions may be useful in certain regards (for example in avoiding distraction of a user), and the use of two distinct pitches or other components likewise may be useful (for example in make the emission more distinctive), and whistles also may be useful in generating acoustic emissions (for example being inexpensive, easily mass-produced, and reliable), other arrangements may be equally suitable. Furthermore, as previously noted, while a smart phone or similar portable electronic device may present certain advantages as a station, such as already being widely available and frequently carried on users' persons, the use of smart phones as stations also is an example only.

Now with reference to FIG. 6A through FIG. 6D, as noted previously embodiments are not limited only to eye drop bottles as containers. FIG. 6A through FIG. 6D show an example arrangement for a pill bottle as may be used to contain and dispense pills, tablets, capsules, etc. The arrangements in FIG. 6A through FIG. 6D may be at least somewhat similar to those in FIG. 1A through FIG. 1D, with a different container (and as noted previously, the container is not necessarily part of a given embodiment).

In FIG. 6A, a remote 0616A is shown, approximately spherical in shape and truncated at top and bottom. The remote 0616A includes a wall 0622A enclosing an interior containing a volume of air, and an acoustic emitter 0618A illustrated in the form of a whistle (though such is not limiting). A container 0632A is engaged with the remote 0616A, disposed within an aperture of the remote 0616A. The container 0632A includes a cap 0631A therefor, as may for example engage with the container 0632A with screw threads, through a friction fit, a "child-proof" safety latch, etc.

In FIG. 6B, a remote 0616B with a wall 0622B and an acoustic emitter 0618B is shown, with a container 0632B having a cap 0631B engaged therewith. The wall 0622B of the remote 0616B is slightly indented to either side, for example as may be a result of compression applied to the remote 0616B in picking up the remote 0616B.

Moving on to FIG. 6C, again a remote 0616C is shown having a wall 0622C and an acoustic emitter 0618C, along with a container 0632C with a cap 0631C engaged therewith. As may be seen the sides of the wall 0622C are deeply indented. In addition, the cap 0631C is shown as separated from the container 0632C. Such deformation as shown in FIG. 6C may result for example from a user gripping the remote 0616C with sufficient strength as to unthread a cap, pop off a friction fitted cap, etc. When such deformation of the remote 0616C occurs, the volume available for air inside the wall 0622C may be reduced. Air may be communicated from inside the wall 0622C to the outside environment via the acoustic emitter 0618C, causing the acoustic emitter 0618C to produce an acoustic emission 0620C. Thus, as the container 0632C is opened the whistle may produce a pitch.

Now with regard to FIG. 6D, an arrangement is shown with a remote 0616D having a wall 0622D and an acoustic emitter 0618D, and a container 0632D engaged therewith. The container 0632D is not shown to have a cap. The remote 0616D and the container 0632D engaged therewith are inclined approximately 120 degrees from vertical. A dispersal 0642D in the form of a pill is shown near and slightly below the mouth of the container 0632D, as may occur when the container 0632D is dispensing medication. In addition, the wall 0622D is slightly indented, for example as may be produced by pressure applied by a user holding and/or manipulating the container 0632D. Thus, the arrangement of FIG. 6D may be understood to show the container 0632D dispensing a dispersal 042D of medication.

It is noted with regard to FIG. 6C and FIG. 6D, an acoustic emission 0620C is produced upon opening the container 0632C as shown in FIG. 6C, but an acoustic emission is not shown upon dispensing a dispersal 0642D of medication in FIG. 6D. Such an arrangement may be considered to address a contextual event (e.g., opening the container) rather a medication event proper (e.g., dispensing/applying the medication). Thus, for arrangements similar to those of FIG. 6A through FIG. 6D a station (not shown in FIG. 6A through FIG. 6D) may receive an acoustic emission associated with dispensing and/or using a medication, without necessarily receiving an acoustic emission that indicates the act of dispensing medication (or using medication) per se. For at least certain embodiments, a station may determine that a medication has been dispensed/used based on such contextual events, without considering medication events themselves (though receipt and/or consideration of medication events, in addition to or in place of contextual events, is not prohibited).

Moving on to FIG. 7A and FIG. 7B, another example remote 0716A is shown, including a wall 0722A and an acoustic emitter 0718A. A container 0732A is engaged with the remote 0716A, disposed within an aperture of the remote 0716A. The container 0732A as illustrated is a squeeze tube, as may contain and dispense ointments or similar medications (and/or other materials).

In FIG. 7B, a remote 0716B with a wall 0722B and acoustic emitter 0718B is shown, with a container 0732B engaged therewith. As may be seen, the wall 0722B of the remote 0716B is deformed inwardly, in turn deforming the container 0732B so as to cause the container 0732B to dispense a dispersal 0742B of medication (illustrated as ointment on an approximately flat surface, such as the palm of a user's hand). In addition, in deforming the container 0732B the volume of air enclosed by the wall 0722B is reduced, expelling air through the acoustic emitter 0718B and producing an acoustic emission 0720B.

As noted previously, remotes are not limited only to engaging with containers for eye drops or similar (although eye drop containers are shown in certain examples herein). As seen in FIG. 6A through FIG. 6D pill bottles may be suitable, and as seen in FIG. 7A and FIG. 7B squeeze tubes also may be suitable. Other suitable containers may include, but are not limited to, hypodermic syringes and inhalers (e.g, "nebulizers").

In addition, with regard to FIG. 7B it may be observed that dispensing the dispersal 0742B of medication does not necessarily equate to administering the medication. That is, where in the arrangement previously shown in FIG. 1D expelling an eye drop 0142D from the container 132D into the user's eye 0148D is at least arguably both dispensing the medication and taking the medication. (Some period may elapse during which time the drop falls from the container into the eye, but such a period typically may be short enough to ignore for at least some purposes of determining whether medication has been administered.) However, in the arrangement shown in FIG. 7B the dispersal 0742B of medication is dispensed but not necessarily applied, e.g., rubbed into the skin, etc. Thus, dispensing a medication is not necessarily equivalent to using that medication. In a strict sense a dispensing event (e.g., dispensing medication) may be considered contextual to a medication event (e.g., actually administering the medication). Nevertheless, determining that a medication has been dispensed may be seen as indicating with high confidence that the medication also has been administered; typically, it may be expected that if medication is dispensed, medication may also be administered. For example, removing an ointment from a tube (as in FIG. 7B) typically may precede applying that ointment to the skin (or other location), and circumstances wherein medication may be dispensed but not applied may be considered as uncommon. While other circumstances may be imagined—e.g., dispensing a pill and then dropping or otherwise losing the pill, etc., such circumstances may not be considered likely. Thus, barring unusual circumstances (or deliberate deception), it may be useful in at least certain instances to equate dispensing a medication with taking that medication, at least with some degree of confidence. Thus, while embodiments may not necessarily determine concretely that medication is taken, determining that medication has been dispensed, that medication containers have been prepared for dispensing (e.g., opened), and so forth may be sufficient to infer that medication has indeed been taken, and/or to register the medication as having been taken.

However, which event or events are determined to occur, and/or the relationship of such events to the use of a medication, is not limited. For certain examples herein, the dispensing of the medication may be considered to be a defining event, given a remote that is engaged with a medication container. However, other arrangements also may be suitable.

Now with reference to FIG. 8A, another example remote 0816A is shown. The remote 0816A includes a wall 0822A, and a container 0832A is engaged with the remote. In addition, the remote 0816A is shown to include two acoustic emitters 0818A1 and 0818A2. As may be seen in FIG. 8B, an arrangement of dispensing medication from the container 0832B is shown. The remote 0816B is inclined, the wall 0822B thereof is indented inward, and a dispersal 0842B of medication is being dispensed into an eye 0848B. In addition, the acoustic emitters 0818B1 and 0818B2 are emitting acoustic emissions 0820B1 and 0820B2, respectively. The number of acoustic emitters in a given embodiment is not limited. Where certain examples herein show one acoustic emitter, others (such as FIG. 8A and FIG. 8B) show more than one.

In addition, what constitutes an acoustic emission 0818B1 and 0818B2 may vary considerably. As shown in FIG. 8B each of the acoustic emitters 0818B1 and 0818B2 produce an individual acoustic emission 0820B1 and 0820B2. For example, acoustic emissions 0820B1 and 0820B2 may be two whistle noises at different pitches. However, while it may be useful in certain instances to consider the acoustic emissions 0820B1 and 0820B2 individually (e.g., two emissions are being produced), it may be equally suitable to consider elements 0820B1 and 0820B2 as components of a single acoustic emission. Thus, multiple components may be considered as a single acoustic emission; likewise, the product of two or more acoustic emitters may be considered as a single acoustic emission. The precise structure and/or contents of an acoustic emission is not limited.

Figure 9A:
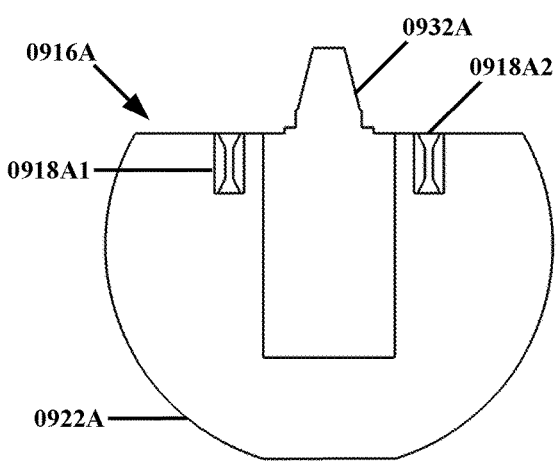
FIG. 9A through FIG. 9C depict an example remote with two sequential emitters and an example container, in cross-section view.
Figure 9B:
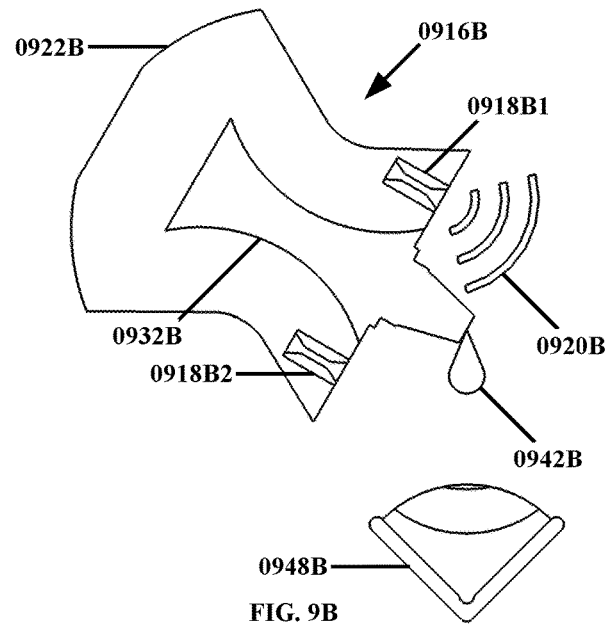

Now with reference to FIG. 9A, an arrangement at least somewhat similar visually to that of FIG. 8A is shown, with a remote 0916A that includes a wall 0922A and two acoustic emitters 0918A1 and 0918A2, and a container 0932A engaged with the remote 0916A. Turning to FIG. 9B, an arrangement wherein a remote 0916B is dispensing a dispersal 0942B of medication into an eye 0948B is shown; the remote includes a wall 922B and acoustic emitters 0918B1 and 0918B2. However, as may be seen only one acoustic emission 0920B is being produced, by acoustic emitter 0918B1; acoustic emitter 0918B2 is not producing an acoustic emission in FIG. 9B.

Figure 9C:
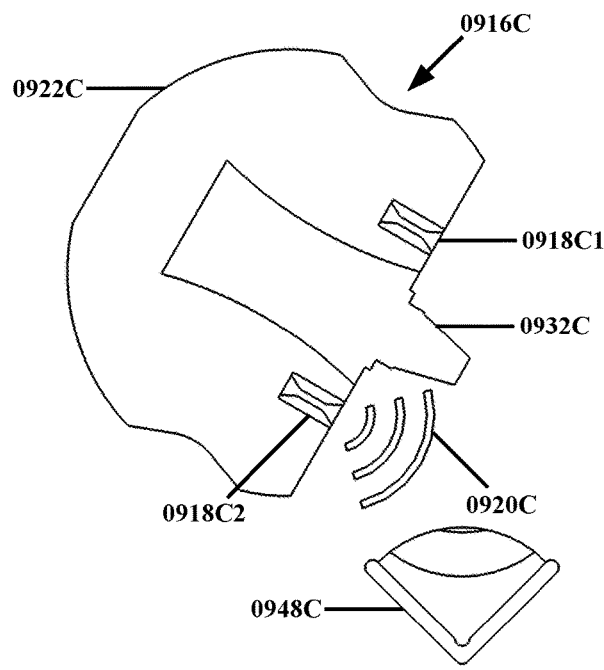

Moving on to FIG. 9C, a remote 0916C is shown including a wall 0922C and acoustic emitters 0918B1 and 0918B2, with a container 932C engaged with the remote 0916C. The wall 0922C is slightly indented, and the container 0932C is positioned over an eye 0948C, as may be the case after an eye drop has been dispensed (e.g., as shown in FIG. 9B). Thus, the arrangement of FIG. 9C may represent a configuration of a remote 0916C as the wall 0922C elastically returns toward a default shape, drawing in air as the volume within the wall 0922C increases.

As may be seen, the acoustic emitter 0918C2 in FIG. 9C is producing an acoustic emission 0920C. Such an acoustic emission 0920C may be produced for example for an acoustic emitter 0918C2 such as a whistle that is configured to produce sound as air is drawn into the remote 0916C, rather than as air is expelled.

Several points are noted. First, the acoustic emission 0920C may be taken as indicating that a medication has been dispensed, even though the acoustic emission 0920C would not be coincident in time with dispensing the medication. That is, since the sound from acoustic emitter 0918C2 is produced as the remote 0916C relaxes towards a default state after being squeezed to expel medication, that sound is produced after the medication has already been dispensed. Such an arrangement—wherein acoustic emissions do not happen at (or necessarily even near) the same time as an event (in FIG. 9C, dispensing medication) that those acoustic emissions represent—may be suitable for at least certain embodiments.

Second, in viewing FIG. 9B and FIG. 9C together, two acoustic emissions 0920B and 0920C are produced one after the other. Thus, not all acoustic emissions must be produced together in time. In addition, as noted with regard to FIG. 7B, although it may be suitable to consider acoustic emissions 0920B and 0920C as distinct (e.g., as two separate sounds) it may be equally suitable to consider the combination of elements 0920B and 0920C as a single acoustic emission having two components. Moreover, it may be suitable to consider 0920B and 0920C as a single acoustic emission even if some time elapses between the production of element 0920B in FIG. 9B and element 0920C in FIG. 9C; sound need not be continuous in order to be considered as a single acoustic emission.

Third, regardless of whether acoustic emissions 0920B and 0920C are considered together or separately, not all acoustic emissions or components thereof need to be produced from the same physical action. In FIG. 9B the acoustic emission 0920B is produced as pressure is applied to the remote 0916B; in FIG. 9C the acoustic emission 0920C is produced as pressure on the remote 0916C is relaxed. Other variations and arrangements also may be suitable.

Now with reference to FIG. 10A, a remote 1016A is shown with a wall 1022A and an acoustic emitter 1018A. A container 1032A is engaged with the remote 1016A. Similarly, in FIG. 10B a remote 1016B is shown with a wall 1022B and an acoustic emitter 1018B, with a container 1032B engaged therewith. The remote 1016B and container 1032B are inclined, and the container 1032B is dispensing a dispersal 1042B of medication into an eye 1048B. The acoustic emitter 1018B is producing an acoustic emission 1020B, e.g., a whistle as air is expelled from within the remote 1016B. Again in FIG. 10C, a remote 1016C is shown with a wall 1022C and an acoustic emitter 1018C, with a container 1032C engaged therewith. An acoustic emission 1020C also is being produced by the acoustic emitter 1018C, e.g., a whistle as air is drawn into the remote 1016C.

Thus, in considering the examples of FIG. 10B and FIG. 10C together as different states of a single remote, an acoustic emitter 1018B and 1018C may produce more than one acoustic emission 1020B and 1020C. For example, one acoustic emission 1020B as air flows out and another acoustic emission 1020C as air flows in. Such an arrangement may be produced for example by a two-way whistle, though other arrangements may be suitable.

As noted previously, it may be equally suitable to consider the acoustic emissions 1020B and 1020C either independently or as components of a whole; acoustic emissions may be produced at different times, and/or in response to different actions, etc. In addition, it is noted that a single acoustic emitter (e.g., 1018B and 1018C assuming FIG. 10B and FIG. 10C to show the same embodiment in different states) may produce more than one acoustic emission 1020B and 1020C. Two such acoustic emissions (or components) 1020B and 1020C need not be identical, or even similar. For example, the acoustic emissions 1020B and 1020C may have different frequencies ("pitches"), waveforms, amplitudes, durations, etc. Embodiments are not limited with regard to how many acoustic emissions a given acoustic emitter may produce, the content/form thereof, or similarity among such acoustic emissions.

Figures 11A, 11B:
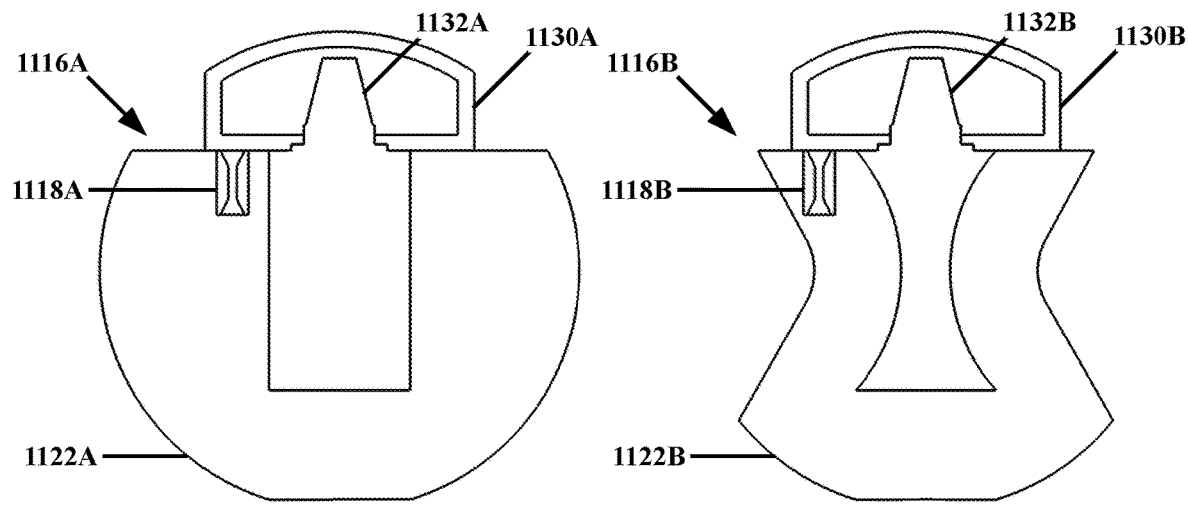
FIG. 11A through FIG. 11C depict an example remote with a controllably obstructed emitter and an example container, in cross-section view.

Turning to FIG. 11A, a remote 1116A is shown with a wall 1122A and an acoustic emitter 1118A, and a container 1132A engaged therewith. In addition, a remote cap 1130A is shown. As may be seen, the remote cap 1130A obstructs the container 1132A, so as to oppose dispensing medication therefrom. Thus, typically the remote cap 1130A may be removed to enable medication to be dispensed from the container 1132A. (Although a cap for the container 1132A proper is not shown, the presence of a container cap for the container 1132A as distinct from the remote cap 1130A is not prohibited.) In addition, the remote cap 1130A also may be seen to obstruct the acoustic emitter 1118A, so as to oppose acoustic emissions therefrom. For example, for an acoustic emitter 1118A in the form of a whistle, blocking or at least muffling air flow through the whistle may reduce or entirely prevent the emission of whistling sounds therefrom.

In FIG. 11B, certain obstruction functions of a remote cap 1130B are illustrated. The remote 1116B is shown with the wall 1122B thereof indented (with the container 1132B likewise indented). In certain instances, such indentation may cause the acoustic emitter 1118B to produce an acoustic emission. However, as may be seen the remote cap 1130B obstructs the acoustic emitter 1118B; thus, an acoustic emission may not produced, may be muffled if produced, etc.

Figure 11C:
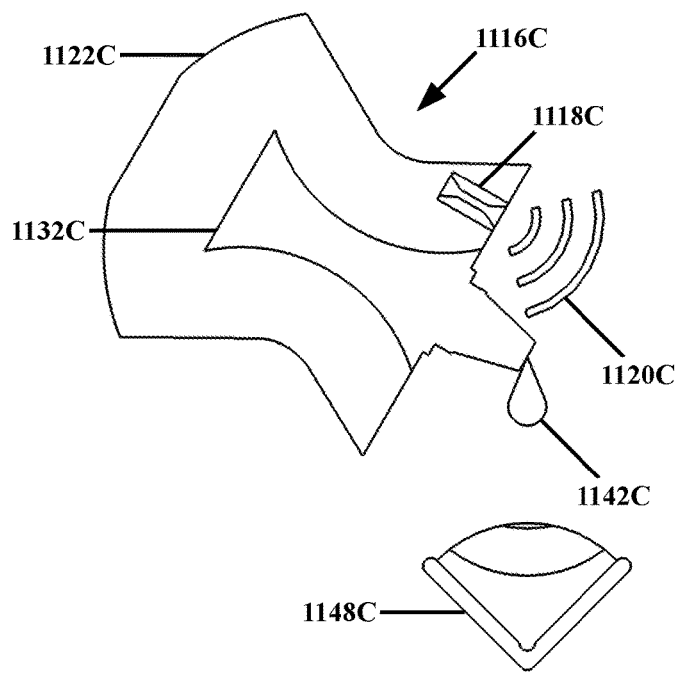

However, as shown in FIG. 11C, without the remote cap (not illustrated in FIG. 11C) in place to obstruct the acoustic emitter 1118C, compressing the wall 1122C of the remote 1116C so as to cause the container 1132C to expel a dispersal 1142C of medication into an eye may again result in the acoustic emitter 1118C producing an acoustic emission 1120C.

Thus, considering FIG. 11B and FIG. 11C together, in at least certain embodiments an acoustic emitter may be obstructed, and/or otherwise controlled, so as to avoid producing acoustic emissions in at least certain circumstances while still producing acoustic emissions in other circumstances. For example, through the use of a remote cap as shown, an acoustic emitter in the form of a whistle may be restricted from a characteristic whistling sound so long as the cap is in place. As a result, if the remote is squeezed with the remote cap in place, for example incidentally (e.g., through fidgeting by the user, compression by other objects in a pocket or bag, etc.), the characteristic acoustic emission may not be produced. In such manner, at least certain instances of "false positive" results may be avoided. The function of a remote cap in such manner as illustrated in FIG. 11B and FIG. 11C is an example only, and other arrangements for obstructing production of acoustic emissions (including but not limited to locking mechanisms for an acoustic emitter, other obstructions, etc.) in various circumstances may be equally suitable.

Now with reference to FIG. 12A through FIG. 12D, in certain previous examples a container was disposed within a remote, the remote including a wall, containing air within, etc. However, embodiments are not limited to such remotes. Indeed, so long as the remote includes at least the acoustic emitter, and/or is otherwise capable of producing a suitable acoustic emission, it may not be necessary for other structure to be present. In addition, while certain previous examples illustrated an acoustic emitter in the form of a pneumatic whistle, this too is an example only, and other arrangements for producing acoustic emissions also may be suitable.

In FIG. 12A, an arrangement is shown with a container 1232A and a cap 1240A for the container 1232A. In addition, an acoustic emitter 1218A is shown, in the form of mechanical projections and recesses, such that sliding the projections and recesses past one another, and/or pulling projections out of recesses, may produce a series of clicks and/or an apparently continuous "zip" noise. (Such mechanisms may be referred to as a "zip strip".) No distinct remote is shown to be present in FIG. 12A. Rather, the acoustic emitter 1218A is integrated into the container 1232A and/or the container cap 1240A. For simplicity, with regard to FIG. 12A the acoustic emitter 1218A may be referred to as a distinct element, as opposed to being or being part of a remote. However, it may be equally suitable to consider the acoustic emitter 1218A as being a remote, e.g., a remote that includes no components other than the acoustic emitter. So long as a remote can carry out the necessary functions, e.g., producing a suitable acoustic emission, precisely which element(s) are required to be present and/or are defined to be part of the remote (as opposed for example to being part of a container, part of some other structure, etc.) is at least somewhat arbitrary. So long as the remote and/or acoustic emitter function suitably, embodiments are not limited with regard to what structure may be present and/or what structure may be part of a remote or may be considered to be part of a remote.

In FIG. 12B, an arrangement is shown with a container 1232B and a container cap 1240B separated slightly from the container 1232B. It may be understood that the container cap 1240B is being/has been removed from the container 1232B. As may be seen, the container cap 1240B is engaged with a portion 1218B1 of an acoustic emitter, and that the container 1232B is engaged with another portion 1218B2 of an acoustic emitter. The two portions 1218B1 and 1218B2 of the acoustic emitter have cooperated to produce an acoustic emission 1220B, e.g., in sliding past one another as the container cap 1240B was removed from the container 1232B. Thus, as the container 1232B is opened, (e.g., in preparation to dispense medication) the acoustic emission 1220B is produced.

Embodiments are not limited with regard to whether an acoustic emitter is integral or in multiple parts, or with regard to how an emitter may be engaged with a container (or a remote). For example, in FIG. 12B the portion 1218B1 of the acoustic emitter in the container cap 1240B may be an element such as a stamped or injection-molded part inserted into the container cap 1240B, while the portion 1218B2 of the acoustic emitter on the container 1232B may be molded integrally with the container 1232B itself. Other arrangements also may be suitable.

Likewise, embodiments are not limited with regard to the nature of the acoustic emission. Certain previous examples have shown acoustic emissions produced by whistles, as may include one or more whistle pitches. The example in FIG. 12B shows an acoustic emission produced by a zip strip, as may include a rapid series of clicks, etc. However, other arrangements may be equally suitable. In particular, it is noted that acoustic emissions are not required to be audible to human hearing. For example, pitches too high (or too low) for hearing, such as may be emitted by a so-called "dog whistle", may be suitable. Such acoustic emissions, being inaudible, may not distract or otherwise disturb a user, while still being detectable (e.g., by a station). However, audible acoustic emissions, while not required, also are not excluded.

Moving on to FIG. 12C, a container 1232C with a portion 1218C2 of an acoustic emitter is shown therein. The container 1232C is inclined, and a dispersal 1242C of medication in the form of a pill is visible near the mouth of the container 1232C, as may occur when the medication is being dispensed. While dispensing the medication itself may not produce an acoustic emission, it is again noted that contextual events—such as opening/closing the container 1232C— may nevertheless be considered in determining whether medication has been dispensed.

In FIG. 12D, an arrangement is shown with a container 1232D and a container cap 1240D engaged therewith. It may be understood that the container cap 1240D is being/has been engaged with the container 1232D. The acoustic emitter 1218D has produced an acoustic emission 1220D, e.g., in portions of the acoustic emitter 1218D sliding past one another as the container cap 1240D was replaced on the container 1232D. Thus, as the container 1232B is closed, (e.g., subsequent to dispensing medication) the acoustic emission 1220D is produced. It is noted that the acoustic emission 1220D produced in replacing the container cap 1240D in FIG. 12D may not necessarily be identical to the acoustic emission 1220B produced when removing the container cap 1240B in FIG. 12B (nor is it required that both acoustic emissions be identical, even if made by the same acoustic emitter). For example, a single acoustic emitter may produce different acoustic emissions when being disengaged (e.g., in FIG. 12B) than when being engaged (e.g., in FIG. 12D).

Given the arrangement in FIG. 12B through FIG. 12D, it may be understood that acoustic emissions 1220B and 1220D may be produced "bracketing" the dispensing of medication, that is, one acoustic emission 1220B before dispensing and another acoustic emission 1220D after. Depending on the particulars of an embodiment, a determination may be made (e.g., at a station, not shown) that medication has been dispensed if either such acoustic emission is detected, only if both acoustic emissions are detected, if both acoustic emissions are detected in the proper sequence (e.g., if the acoustic emissions 1220B and 1220D are distinguishable from one another), etc. Again, while the actual dispensing and/or taking of medication may not be detected for all embodiments (and may not be required to be detected), nevertheless dispensing/taking the medication may be inferred with at least some confidence based on context, e.g., acoustic emissions from opening and closing the medication container.

Turning to FIG. 13A through FIG. 13D collectively, although it may be suitable for certain embodiments to produce acoustic emissions in response to contextual events (such as opening/closing a container), and for other embodiments to produce acoustic emissions in response to medication dispensing events, embodiments are not limited to one or the other, that is, to either indicating context or dispensing. In FIG. 13A through FIG. 13D, an example arrangement is shown wherein both a dispensing event and contextual events produce acoustic emissions.

Figures 13A, 13B:
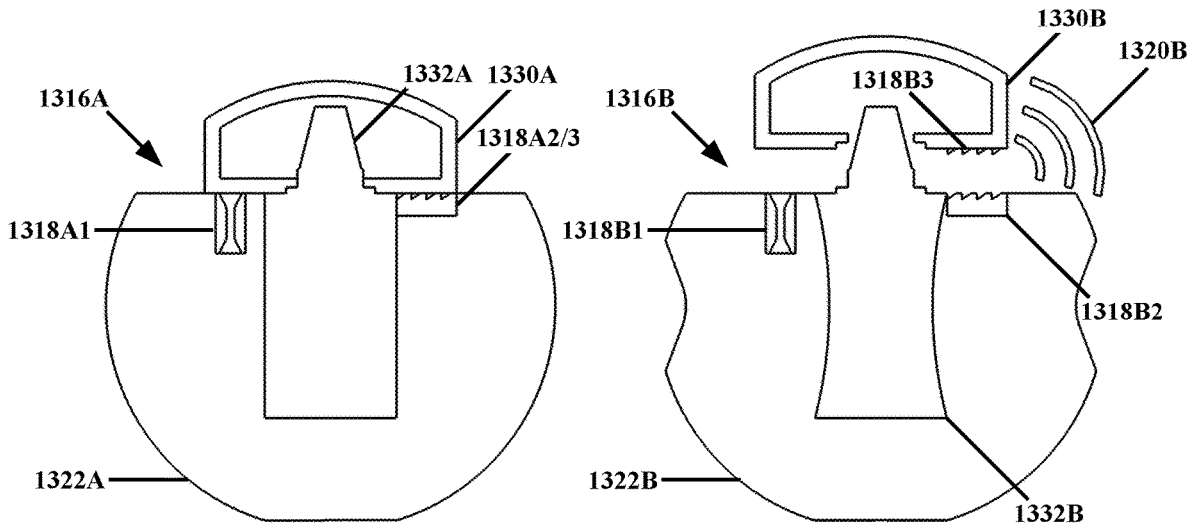
FIG. 13A through FIG. 13D depict an example remote with multiple dissimilar emitters producing emissions upon different events and an example container, in cross-section view.

In FIG. 13A, a remote 1316A having a wall 1322A is shown. Two acoustic emitters 1318A1 and 1318A2/3 are present; acoustic emitter 1318A1 is illustrated in the form of a whistle, and acoustic emitter 1318A2/3 is illustrated in the form of a zip strip (e.g., elements 1318A2 and 1318A3, not individually identified in FIG. 13A). A medication container 1332A is engaged with the remote 1316A, and a remote cap 1330A is also engaged with the remote 1332A.

Moving on to FIG. 13B, a container 1332B including a wall 1322B is shown with a container cap 1340B separated slightly from the container 1332B. It may be understood that the remote cap 1330B is being/has been removed from the remainder of the remote 1316B. The remote 1316B includes an acoustic emitter 1318B1. In addition, the remote cap 1330B includes a portion 1318B2 of another acoustic emitter; the remainder of the remote 1316B includes another portion 1318B3 of that same acoustic emitter. The two acoustic emitter portions 1318B2 and 1318B3 have cooperated to produce an acoustic emission 1320B, for example in pulling away from one another as the remote cap 1330B was removed from the remote 1316B (e.g., in preparation for dispensing medication).

Figures 13C, 13D:
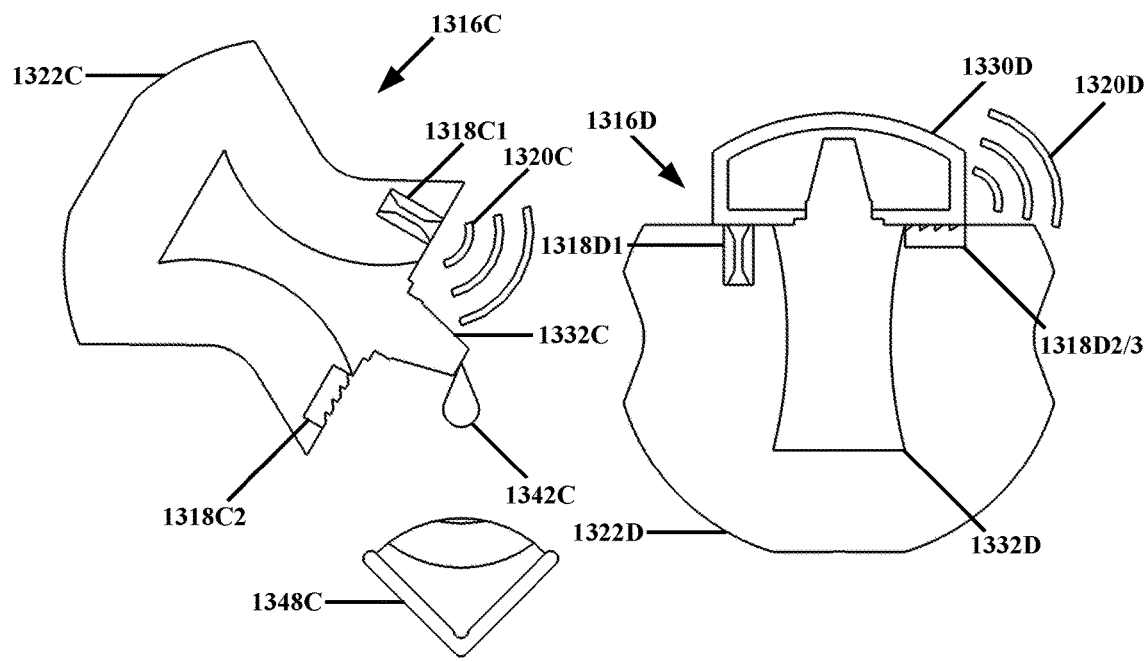

In FIG. 13C, a remote 1316C with a wall 1322C, an acoustic emitter 1318C1, and an acoustic emitter portion 1318C2 is shown inclined and disposed over an eye 1348C. The wall 1322C is indented, as is the container 1332C, such that a dispersal 1342C of medication is being dispensed from the container 1332C. The acoustic emitter 1318C1 is producing an acoustic emission 1320C.

Continuing in FIG. 13D, a remote 1316D with a wall 1322D, an acoustic emitter 1318C1, and another acoustic emitter 1318C2/3 is illustrated. A medication container 1332D is engaged with the remote 1316D. A remote cap 1330D is also engaged with the remote 1316D. It may be understood that the remote cap 1330D is being/has been replaced on the remote 1316D. In addition, the acoustic emitter 1318D2/3 is shown producing an acoustic emission 1320D, for example in engaging with one another as the remote cap 1330D was replaced on the remote 1316D (e.g., subsequent to dispensing medication).

Considering FIG. 13B through FIG. 13D as a sequence, in such instance three acoustic emissions 1320B, 1320C, and 1320D are produced, at different times and originating from different actions and different emitters. Acoustic emission 1320B is produced as the remote cap 1330B is removed; acoustic emission 1320C is produced as the eye drop container 1332C is squeezed (via the remote 1316C) to expel the eye drop 1342C; and acoustic emission 1320D is produced as the remote cap 1330D is replaced. Thus, three distinct acoustic emissions (or, considered differently, three components of one acoustic emission) occur in sequence as medication is used. Contextual events drive two acoustic emissions (1320B and 1320D), while a dispensing event (as may alternately be considered a medication event) drives another acoustic emission (1320C). As may be understood, embodiments are not limited with regard to the physical sources of acoustic emissions, the events driving acoustic emissions, uniformity of acoustic emissions (e.g., whether different emissions are different from one another, produced differently, etc.), and so forth.

Now with reference to FIG. 14A through FIG. 14D, as previously described, through receiving and considering acoustic emissions (e.g., at a station) a determination may be made as to whether a medication has been dispensed, used, etc. However, information as may be conveyed through acoustic emissions is not limited only to the fact of dispensing or use. Embodiments may convey other information, such as relating to the manner in which a medication is used. For example, dosage dispensed may be determined in at least certain instances.

Figure 14A:
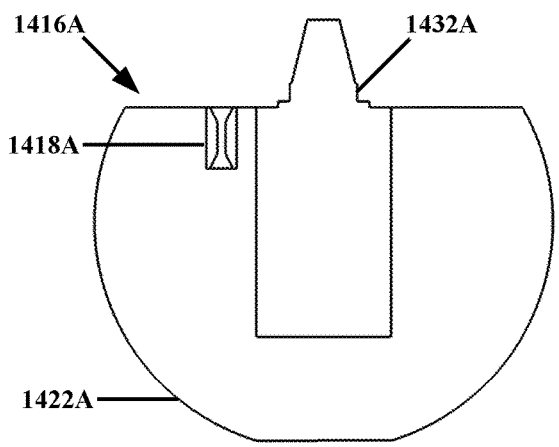
FIG. 14A through FIG. 14D depict an example remote adapted to indicate dosage dispensed and an example container, in cross-section view.
Figure 14B:
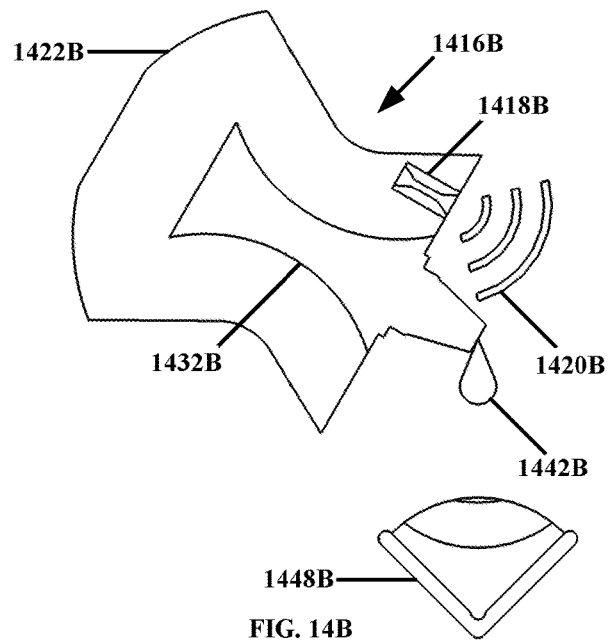

FIG. 14A depicts a remote 1416A with a wall 1422A and an acoustic emitter 1418A. A medication container 1432A is engaged with the remote 1416A. FIG. 14B also shows a remote 1416B with a wall 1422B and acoustic emitter 1418B, and a medication container 1432B engaged therewith. The remote 1416B and container 1432B are inclined and deeply indented. The container 1432B is dispensing a dispersal 1442B of medication to an eye 1448B, while the acoustic emitter 1418B is producing an acoustic emission 1420B.

Figure 14C:
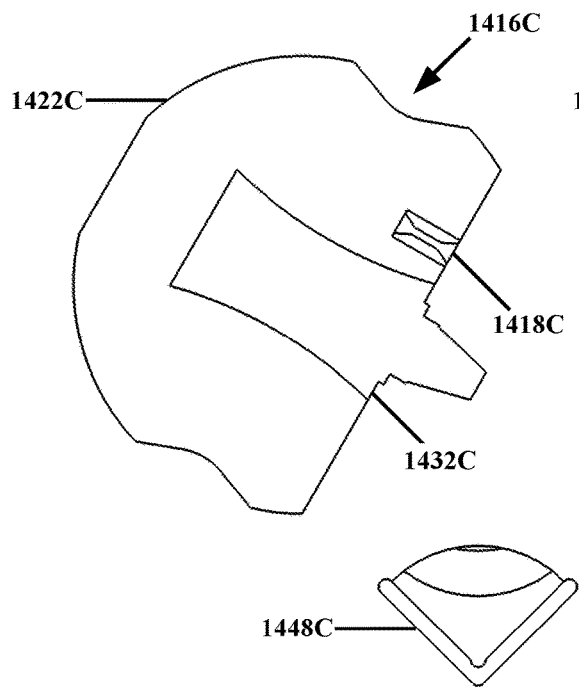
Figure 14D:
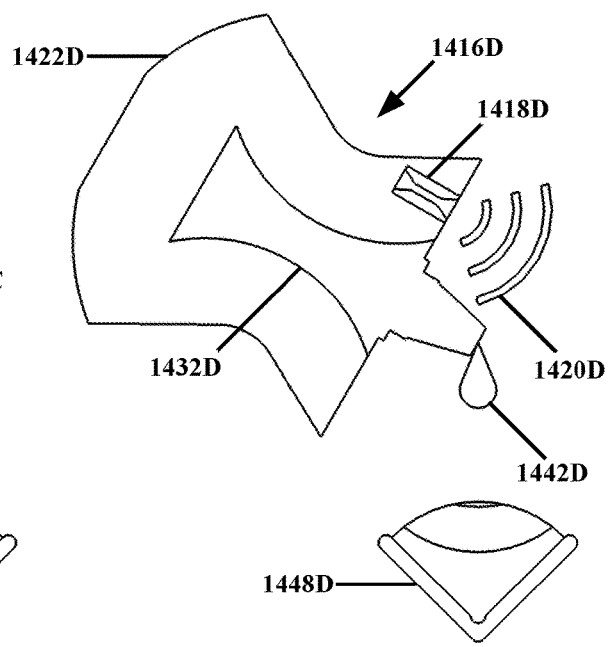

In FIG. 14C, a remote 1416C with a wall 1422C and acoustic emitter 1418C, and a medication container 1432C engaged therewith, is again shown. The remote 1416C and container 1432C are inclined similarly to FIG. 14B, but are only slightly indented. Turning to FIG. 14D, a remote 1416D is shown with a wall 1422D and acoustic emitter 1418D, and a medication container 1432B engaged therewith. Again, the remote 1416D and container 1432D are inclined and deeply indented, the container 1432D is dispensing a dispersal 1442D of medication to an eye 1448D, and the acoustic emitter 1418D is producing an acoustic emission 1420D.

If FIG. 14B through FIG. 14D are considered as a sequence of events, the events depicted therein may represent applying two droplets 1442B and 1442D of medication into a user's eye, in FIG. 14B and in FIG. 14D respectively. As may be seen, two acoustic emissions 1442B and 1442D (or considered alternatively, two components of a single acoustic emission) also are produced, associated with the two droplets 1442B and 1442D respectively. If the acoustic emissions 1420B and 1420D are received (e.g., in a station), then the number of droplets 1442B and 1442D dispensed may be determined therefrom. Thus, as may be seen, for at least certain embodiments the dosage of medication dispensed may be determined based on acoustic emissions.

As has been described, embodiments may enable determination of various information regarding the dispensing, use, etc. of a medication. However, it is noted that such information is not required to be, and typically may not be, embedded into the acoustic emissions themselves. For example, a given acoustic emission typically may not be modulated in the manner of a radio or television broadcast, wherein a voice, picture, or other data is embedded into the signal itself (e.g., through actively varying the amplitude or frequency of an electromagnetic wave). Rather, the acoustic emissions of various embodiments may themselves be the information, and/or convey the information by the existence (rather than the content) of the acoustic emissions. For example, an acoustic emission in the form of a two-pitch ultrasonic whistle may serve as an indication that a medication has been dispensed, but may not have a message to that effect encoded into the whistle.

Acoustic emissions (and the remote, etc.) for various embodiments may be considered "dumb", for example, a characteristic two-pitch whistle, with no information encoded therein. A remote may not require power, computational control, "intelligence", active modulation, etc., and acoustic emissions likewise may simply be sounds with no data encoded therein. For example, for certain example embodiments presented herein, a remote may as be a purely mechanical squeezable bladder, akin to a so-called "squeaky toy", adapted to engage with a medication container. Such an arrangement may not typically be referred to as a "smart device".

Nevertheless, even though the acoustic emissions and/or the emitters thereof are themselves may reasonably be characterized as "dumb", embodiments overall (and/or parts thereof, such as a station) may be characterized as "smart", and/or exhibit smart functionality. For example, embodiments may register whether a medication was dispensed, when, where, in what dosage, etc., and/or similarly whether a medication container has been manipulated, when, where, in what manner (e.g., by removing a cap, etc.), and so forth.

Such an arrangement—"smart" functionality with a "dumb" remote—may present certain advantages. For example, smart functions may be enabled, even though the remote and/or medication container themselves may not require power supplies, processors, sensors, etc. As a more concrete example, an embodiment akin to a squeaky toy may be a purely mechanical device, insensitive to issues such as processor or software malfunctions, sensor damage, dead batteries, and so forth (because there may be no processor, software, sensor, battery, etc.). Likewise, a remote that does not rely on electromagnetic communication may not be susceptible to electromagnetic interference (whether suffering from or causing such interference), may not exhibit difficulties with communication protocols, etc. In additional, a simple mechanical device may be robust, and thus at least potentially less prone to problems due to physical damage, environmental factors (such as getting wet), and so forth. Also, avoiding electronic components in a remote may reduce the cost, weight, complexity, etc. of a remote, making widespread smart functionality (such as autonomous acquisition of authenticated medication adherence information) more feasible and/or user friendly.

However, it is emphasized that functionality as described herein that is "dumb", unpowered, not reliant on processors, etc., does not exclude other functionality that may utilize processors, and/or other "smart" features. For example, an embodiment of a remote may utilize a squeeze ball with a whistle—a purely mechanical system not requiring a processor, sensors, or power—while that same remote nevertheless may incorporate a processor, sensors, power supply, etc., carrying out other functions (e.g., using capacitive sensors to measure the medication remaining in a container engaged with that remote). Thus, while certain functions as described herein may be implemented using "dumb" approaches, the presence of smart functions even in the same system is not prohibited. In such an arrangement, even if smart systems in a remote may fail due to (for example) lack of power to the remote, other functions such as a whistle producing acoustic emissions as may indicate that the medication has been dispensed still may be carried out. Other advantages and features of "mixed" smart-and-dumb systems also may be provided.

Now with reference to FIG. 15A through FIG. 15D, although it may be useful in certain instances for acoustic emissions themselves to be a signal, rather than contain an embedded signal, nevertheless in other instances it may be useful to extract information from an acoustic emission. Even so, extracting such information from within an acoustic emission may not require the acoustic emitter (or remote overall) to be a smart device, or otherwise diminish advantages of dumb remotes/emitters as noted previously.

For example, FIG. 15A illustrates a remote 1516A with a wall 1522A and an acoustic emitter 1518A1 in the form of a whistle. The remote 1516A also includes another acoustic emitter 1518A2 in the form of a bell. In addition, a medication container 1532A is engaged with the remote 1516A.

FIG. 15B shows a remote 1516B with a wall 1522B and acoustic emitters 1518B1 and 1518B2, and a medication container 1432B engaged therewith. The remote 1516B and container 1532B are inclined, and are positioned over an eye 1548B. The acoustic emitter 1518B2 is shown to be producing an acoustic emission 1520B. For example, a bell suspended so as to ring when disturbed may make one or a series of ringing pitches. Thus, the acoustic emission 1520B may be produced as the acoustic emitter 1518B2 is inclined into an orientation as to facilitate the container 1532B dispensing an eye drop into an eye 1548B. In such instance, reception of the acoustic emission 1520B (e.g., in a station) may be taken to indicate such a change in orientation of the container 1532B. Depending on the particulars of the acoustic emitter 1518B2 (e.g., the type of bell, the manner of mounting, etc.), in addition to or instead of being produced upon a change in orientation, an acoustic emission 1520B may be produced upon a change in position (that is, movement through space rather than rotation within space).

Furthermore, for at least certain embodiments, the acoustic emission 1520B may be characteristic not only of the acoustic emitter 1518B2, but of the manipulation of the remote 1516B and container 1532B. That is, a rotation of the remote 1516B may cause the acoustic emitter 1518B2 to emit an acoustic emission 1520B exhibiting one particular pattern of tones that is identifiable as being caused by rotation, while a translation of the remote 1516B may cause the acoustic emitter 1518B2 to emit an acoustic emission 1520B exhibiting a different pattern of tones that is identifiable as being caused by translation. Certain embodiments may enable acoustic emissions 1520B that may be interpreted to indicate complex motions (e.g., being lifted, inclined, shifted to another eye, then set down), magnitudes of motion (e.g., inclination of 120 degrees), speeds, accelerations, and/or other properties. Such properties may be determined by the content of the acoustic emission itself (such as by the particular pattern of tones from a suspended bell), by environmental factors affecting the acoustic emission (such as a doppler shift in an expected series of tones), or by some combination thereof. Typically. though not necessarily, such information may be extracted from an acoustic emission 1520B in a processor utilizing executable instructions instantiated thereon, for example a processor of a station.

However, although in at least certain embodiments information may be determined from the content of an acoustic emission 1520B, it is noted that the content need not be encoded into that acoustic emission 1520B in an active manner. That is, the sound of a jingling bell may be analyzed to reveal how that bell was moved, but the jingling still may be the result of natural behavior by a "dumb" system. Thus, even if such information may be extracted from an acoustic emission 1520B for a given embodiment, that embodiment nevertheless may retain advantages of a dumb remote and/or dumb emitter, as described previously.

Now with reference to FIG. 15C, a remote 1516C is shown with a wall 1522C and acoustic emitters 1518C1 and 1518C2, and a medication container 1532C engaged therewith. The remote 1516C and container 1532C are deeply indented, and the container 1532C is shown to have expelled a dispersal 1542C of medication over an eye 1548C of a user. In addition, the acoustic emitter 1518C1 is producing an acoustic emission 1520C.

Then in FIG. 15D, a remote 1516D is shown with a wall 1522D and acoustic emitters 1518D1 and 1518D2, and a medication container 1532D engaged therewith. The remote 1516D and container 1532D are slightly indented, as may occur if the remote 1516D is being gripped but not squeezed to expel medication. In addition, the acoustic emitter 1518D2 is shown to be producing an acoustic emission 1520D. Such an acoustic emission 1520D may be produced for example if a bell jingles as the remote 1516D is set down onto a surface, such as a table or shelf, after dispensing medication. Thus, depending on the particulars of a given embodiment, the acoustic emission 1520D may be interpreted to indicate motion, potentially a particular motion (e.g., being set on a surface) of the remote 1516D.

If FIG. 15B through FIG. 15D are considered as a sequence, an example embodiment of a remote therein may produce a jingling acoustic emission 1520B upon being brought into place for dispensing medication, a whistling acoustic emission 1520C upon dispensing medication, and another jingling acoustic emission 1520D upon being returned to storage after dispensing medication. As noted, some acoustic emissions such as 1520B and 1520D may include (but are not required to include) characteristic content indicating particulars of the triggers for those acoustic emissions 1520B and 1520D, for example how the remote was moved may leave an identifiable signature in the content of the acoustic emissions 1520B and 1520D. Thus, receipt and analysis of acoustic emissions 1520B, 1520C, and 1520D may reveal that the container was moved, dispensed medication, and then was moved again; and further may indicate that the container was so moved in a manner consistent with preparing for dispensing medication and recovering from dispensing medication (though this is not required, and is not limiting).

As may be understood, even if a given remote is a "dumb" device, the information as may be obtained therefrom regarding use of medication is not necessarily limited, and in particular is not limited only to binary indications of use or no use (or of dispensing or not dispensing, etc.).

Moving on to FIG. 16A through FIG. 16D collectively, the manner by which a remote may engage a container is not limited. As noted with regard to FIG. 12A through FIG. 12D, in certain embodiments a remote may take the form of elements integrated into a container, and in such instances a means of engagement may be considered moot. However, even where a well-defined and distinct remote does engage with a well-defined and distinct container, the means of engagement may vary considerably. Certain examples herein show a friction fit, wherein a remote defines an aperture therein and the container fits securely within that aperture. However, this is an example only. Other suitable arrangements may include, but are not limited to, adhesive, hook-and-loop, threading or other mechanical engagement of remote and/or container, mechanical fasteners, etc. Engagement between a remote and a container may be removable or fixed, without limit.

Figure 16A:
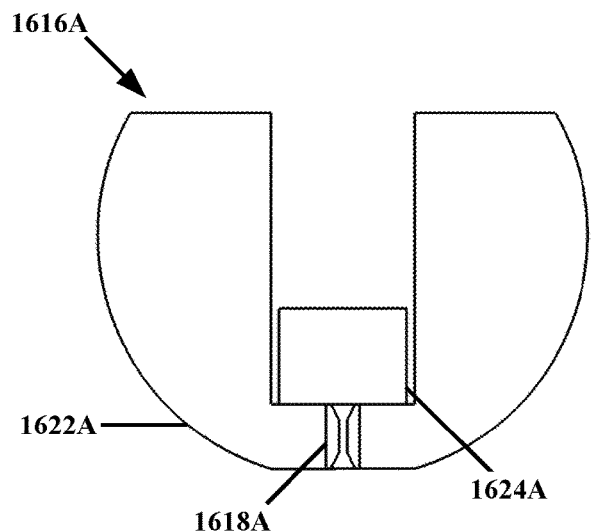
FIG. 16A through FIG. 16D depict an example remote adapted to indicate insertion and removal of a container, in cross-section view.

In addition, the manner of engagement itself may be associated with a characteristic acoustic emission. In FIG. 16A, a remote 1616A is shown with a wall 1622A and an acoustic emitter 1618A. The remote 1616A defines an aperture (not numbered) for accepting a container (not present in FIG. 16A). The remote 1616A also includes a bladder 1624A in pneumatic communication with the acoustic emitter 1618A (in the example shown, the acoustic emitter 1618A is not shown to be in pneumatic communication with the volume enclosed by the wall 1622A, as in certain other examples herein).

Figure 16B:
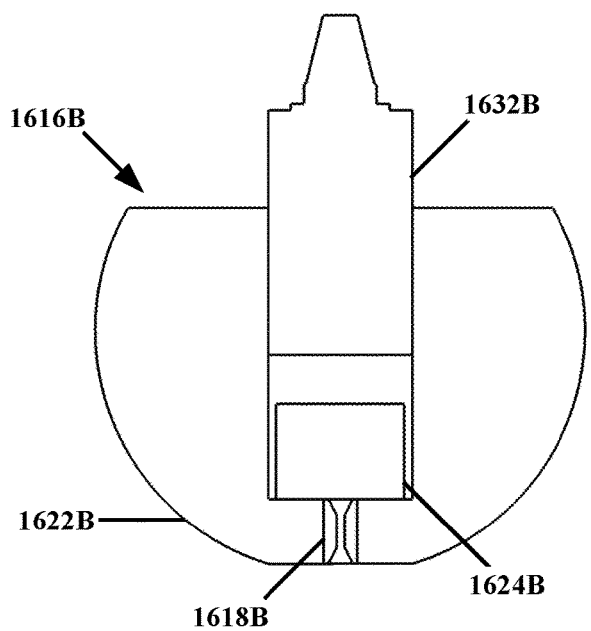

FIG. 16B shows a remote 1616B with wall 1622B, acoustic emitter 1618B, and bladder 1624B, with a container 1632B disposed partway into an aperture in the remote 1616B. Such an arrangement may occur for example as the container 1632B is being inserted into the remote 1616B.

Figure 16C:
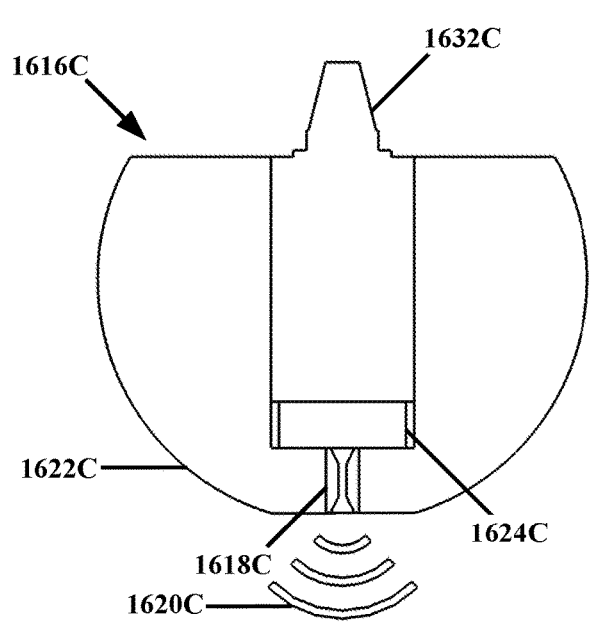

Turning to FIG. 16C, a remote 1616C is shown with a wall 1622C, acoustic emitter 1618C, and bladder 1624C. A container 1632C is disposed within the remote 1616C. As may be seen, the bladder 1624C is compressed by the container 1632C. Air thus is expelled from the bladder 1624C through the acoustic emitter 1618C, producing an acoustic emission 1620C. Such an acoustic emission 1620C may be received and interpreted to indicate that the container 1632C has been engaged with the remote 1616C, for example if a new supply of medication is being prepared for use.

Figure 16D:
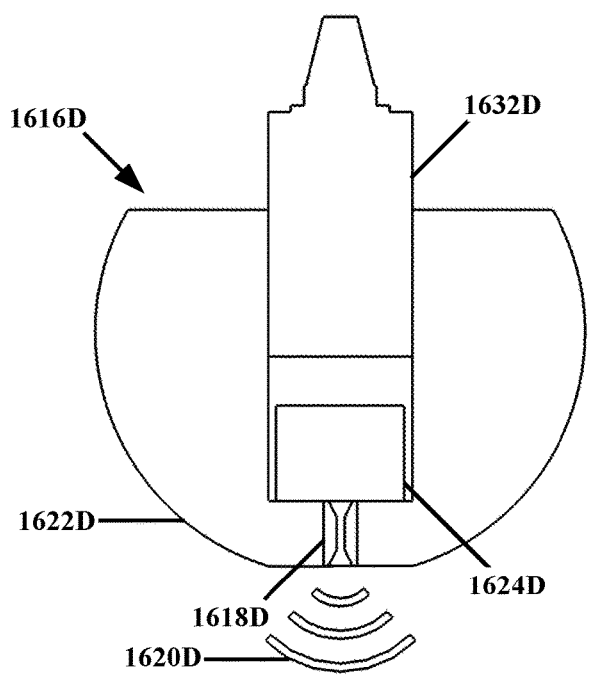

In FIG. 16D, a remote 1616D is shown with a wall 1622D, acoustic emitter 1618D, and bladder 1624D. A container 1632D is shown partly withdrawn from the remote 1616D. As may be seen, compression on the bladder 1624D by the container 1632D is relieved. Air thus is drawn into the bladder 1624D through the acoustic emitter 1618D, producing an acoustic emission 1620D. Such an acoustic emission 1620D may be received and interpreted to indicate that the container 1632D is being disengaged from the remote 1616D, for example if the container 1632D is empty and in need of replacement.

Thus, as may be seen in FIG. 16A through FIG. 16D, actions/states/data not associated immediately with dispensing of a medication also may be indicated through production of acoustic emissions, and/or identified through reception and analysis thereof. For example, engaging or disengaging a medication container from a remote, which may happen well before or well after any act of dispensing the medication, may be so identified through characteristic acoustic emissions.

Now with regard to FIG. 17A and FIG. 17B, certain previous examples have shown purely mechanical mechanisms for producing acoustic emissions. Such arrangements may be transparent to the user, and/or consequential in function. That is, with regard to transparency, the user may not be required to take action other than dispensing the medication in order to produce an acoustic emission indicating that the medication has been dispensed (or that some related act has been carried out). For example, squeezing a remote may both squeeze a container to expel medication and expel air from a bladder to produce a characteristic whistle; so far as the user is concerned, in dispensing the medication no further action may be required in order for the dispensing to be registered (e.g., in a station). With regard to consequentiality in function, the remote itself may be "dumb". That is, an acoustic emission may be produced as a consequence of dispensing the medication, without relying on data processing, choices to be made by the system or user, etc. For example, squeezing an air-filled remote drives air through a whistle, producing a whistle pitch; no "intelligence" or control may be required. In such an arrangement, the whistle pitch is a purely mechanical consequence of squeezing the remote.

However, while purely mechanical approaches may provide transparent and consequential functionality, it is not required for all embodiments to utilize purely mechanical approaches.

For example, FIG. 17A shows a remote 1716A with a wall 1722A. A container 1732A is engaged with the remote 1716A. In addition, the remote 1716A includes an acoustic emitter 1718A in the form of an electrical audio speaker, and a trigger 1750A in the form of a piezoelectric pad in communication with the acoustic emitter 1718A.

In FIG. 17B, a remote 1716B and container 1732B are shown inclined over an eye 1748B. The wall 1722B of the remote 1716B and the container 1732B are indented, such that the container 1732B is dispensing a dispersal 1742B of medication. In addition, the trigger 1750B also is deformed by the indentation of the wall 1722B. Deformation of the trigger 1750B (being in this example a piezoelectric pad) produces an electrical output which is communicated to the acoustic emitter 1718B; the acoustic emitter 1718B thus produces an acoustic emission 1720B.

The arrangement in FIG. 17B for producing the acoustic emission 1720B is not purely physical. An electrical output is generated, and an electrical system—the acoustic emitter 1718B—is activated. However, the arrangement of FIG. 17B is nevertheless both transparent to the user and consequential. The user need perform no more action to cause the acoustic emission 1718B to be produced than for example if the acoustic emitter 1718B were a whistle instead of a speaker (and indeed, if the acoustic emission 1720B is not audible, such as an ultrasonic sound, the user may not even be aware that an acoustic emission 1720B has been produced). Likewise, even though the acoustic emitter 1718B is electrically activated, such activation is still a direct consequence of the user squeezing the remote 1716B. Given a configuration of a particular embodiment (such as shown in certain previous examples), squeezing an air filled wall pushes air through a whistle and necessarily produces a sound; for a different embodiment such as shown in FIG. 17B, deforming a piezoelectric pad causes an electrical output that just as necessarily drives a speaker to produce a sound. No "intelligence", choice, internal processing, etc. may be involved (or required). Thus, although strictly mechanical systems may be suitable in certain embodiments, embodiments are not limited only to strictly mechanical systems.

Now with reference to FIG. 18A and FIG. 18B, certain embodiments described herein have been specific to acoustic emissions. Acoustic emissions may be convenient for certain embodiments. For example, acoustic emissions may not necessarily be restricted to line of sight, may not necessarily blocked by fabric or similar if a receiver (e.g., in the form of a smart phone) is in a bag, a pocket, etc. However, embodiments are not necessarily limited only to acoustic emissions.

FIG. 18A shows an arrangement at least somewhat similar to that of FIG. 17A. A remote 1816A is shown with a wall 1822A. A container 1832A is engaged with the remote 1816A. The remote 1816A includes an emitter 1818A in the form of an LED (light emitting diode), and a trigger 1850A in the form of a piezoelectric pad in communication with the emitter 1818A.

In FIG. 18B, a remote 1816B and container 1832B are shown inclined over an eye 1848B. The wall 1822B of the remote 1816B and the container 1832B are indented, such that the container 1832B is dispensing a dispersal 1842B of medication. In addition, the trigger 1850B also is deformed by the indentation of the wall 1822B. Deformation of the trigger 1850B (in this non-limiting example a piezoelectric pad) produces an electrical output which is communicated to the emitter 1818B. The electrical output causes the acoustic emitter 1818B to produce a characteristic emission 1820B; for an LED, the emission typically may be in the form of light, whether visible or otherwise (e.g., infrared, etc.). (While a station is not shown in FIG. 18B, it should be understood that if non-acoustic emissions are produced by an emitter, a station cooperating with that emitter may include a receiver other than an acoustic receiver. For example, if an LED is to serve as an emitter, a station may include an optical receiver in addition to or instead of an acoustic emitter. Other similar changes may be suitable depending on the particulars of emitter(s) and/or emission(s) in a given embodiment, and embodiments are not limited with regard thereto)

It is noted that the manner in which a non-acoustic emission may be characteristic may vary, and may depend on the nature of the emitter in a given embodiment. For example, an LED may produce light of a specific frequency, frequency distribution, etc., may produce a particular series of pulses (e.g., three dots and a dash), or similar. The particulars of emissions, acoustic or otherwise, are not limited.

Figure 19A:
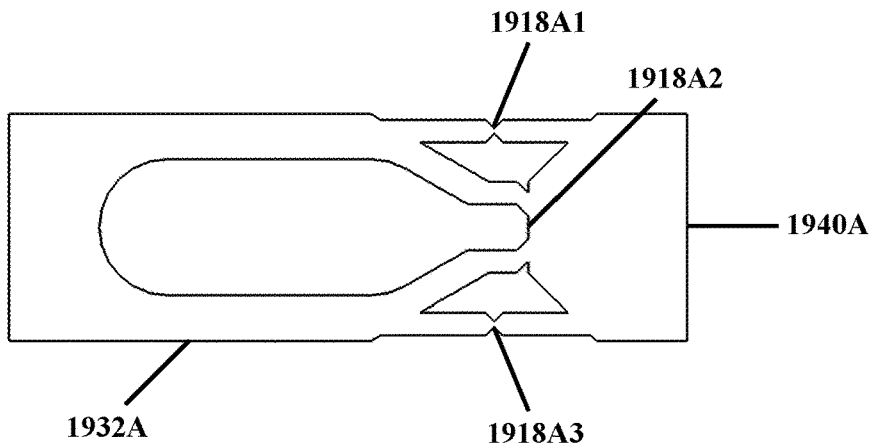
FIG. 19A through FIG. 19C depict an example of destructive acoustic emitters integrated with single-use container and executing in parallel, in cross-section view.
Figure 19B:
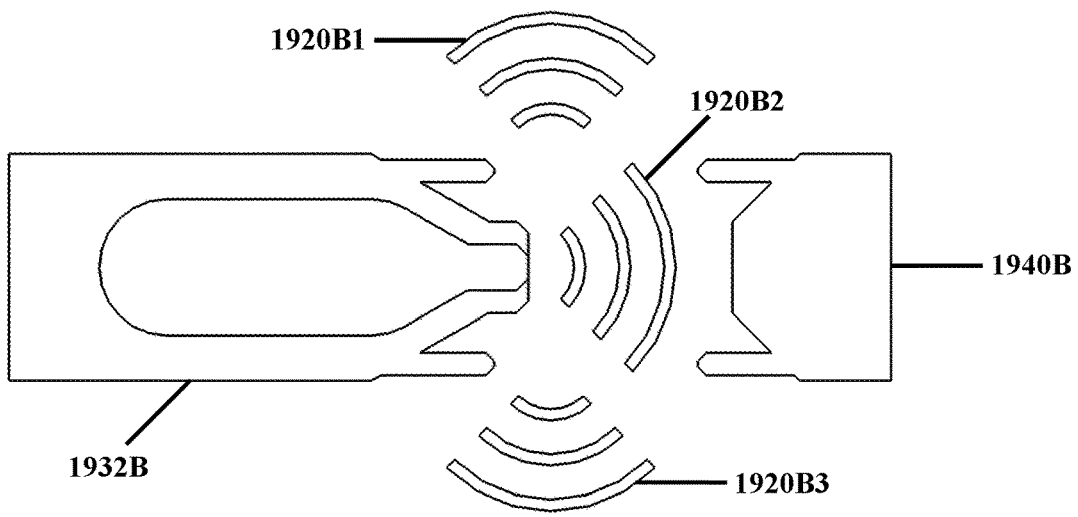
Figure 19C:
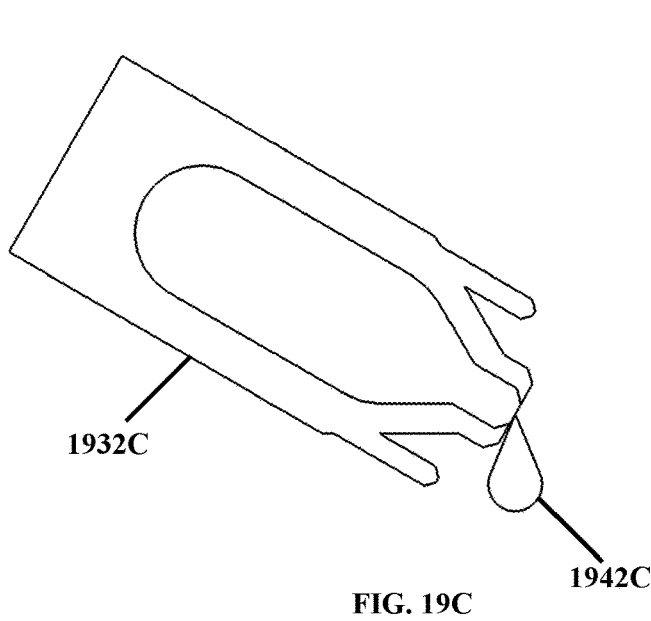

Now with reference to FIG. 19A through FIG. 19C collectively, in certain previous examples herein emissions may have been repeatable, and emitters likewise reusable. For example, in FIG. 1A through FIG. 1D the emitter therein may be considered as a pneumatic whistle, which may produce emissions more than once (assuming the wall of the remote is squeezed more than once), at least potentially being reused many times. However, such repeatability/ reusability is not required, and other arrangements may be suitable. For example, emitters may be expendable, being destroyed in producing an emission, or otherwise not adapted to producing an emission more than once. Similarly, although containers in certain previous examples may be reusable, for example containing therein more than one dose of medication, this also is not required. For example, single-use or "one-shot" containers may be suitable.

In FIG. 19A, a container 1932A is shown therein, as may for example contain a quantity of liquid medication (or other material). A container cap 1940A is shown engaged with the container 1932A. Three points of connection are shown between the container 1932A and the container cap 1940A, in the form of two filaments and a nozzle for the container 1932A; these structures may serve as emitters, and are thus identified as 1918A1, 1918A2, and 1918A3. For example, the container 1932A and the container cap 1940A may be formed integrally, such as being molded out of a plastic material; in such instance, the filaments and nozzle may be frangible (and are shown in FIG. 19A as being notched to define weak points, though such notches/weak points are not necessarily required). Thus, when a pulling force is applied to remove the container cap 1940A from the container 1932A so as to enable dispensing medication therein, the filaments and nozzle may separate in at locations and in a manner that are at least somewhat predictable.

In breaking emitters 1918A1, 1918A2, and 1918A3, sounds may be produced. The precise sounds made may depend on the configuration of the emitters 1918A1, 1918A2, and 1918A3. For example, physical properties such as the shape, thickness, rigidity, strength, elongation, etc., of the structure (e.g., filaments and nozzle as shown) may determine, in whole or in part, certain predictable properties of acoustic emissions produced when those structures 1918A1, 1918A2, and 1918A3 are broken. For instance, the frequency, waveform, volume, etc. of the noises as each emitter 1918A1, 1918A2, and 1918A3 is torn or snapped (or otherwise separated) may be particular to and/or predictable from the structures of the emitters 1918A1, 1918A2, and 1918A3. Consequently, through selection of suitable materials, shapes, etc., the emitters 1918A1, 1918A2, and 1918A3 may be configured so as to produce characteristic acoustic emissions when broken.

Thus, as may be seen in FIG. 19B, separating the cap 1940B and the container 1932A may produce three such characteristic acoustic emissions 1920B1, 1920B2, and 1920B3 by the destruction of the former acoustic emitters (not separately numbered in FIG. 19B, though the remains of the structures themselves may be observed). If the emitters 1918A1, 1918A2, and 1918A3 previously shown in FIG. 19A are distinct from one another, then the acoustic emissions 1920B1, 1920B2, and 1920B3 shown in FIG. 19B likewise also may be distinct from one another. As a result, the example arrangement shown in FIG. 19B may produce three different sounds at approximately the same time, thus providing three overlapping pitches, waveforms, etc. Such combination of three different acoustic emissions 1920B1, 1920B2, and 1920B3 may be both recognizable and unlikely to otherwise occur as background noise, and thus may be detected and interpreted (e.g., at a station, not shown in FIG. 19B) as a evidence of a contextual event representing that the single-use container 1932B of medication has been opened.

Turning to FIG. 19C, therein a single-use container 1932C is shown dispensing a dispersal 1942C of liquid medication therefrom. While dispensing the dispersal 1942C of medication does not necessarily produce a characteristic acoustic emission in itself (though such is not prohibited), detecting and identifying acoustic emissions 1920B1, 1920B2, and 1920B3 shown previously in FIG. 19B may indicate that the single-use container 1932C has been opened in preparation for dispensing the dispersal 1942C of medication, as a contextual event associated therewith. Thus, although dispensing the dispersal 1942C of medication may not be directly detected, if characteristic acoustic emissions are detected it still may be inferred with at least some confidence that the medication has been dispensed and/or used. This may be considered similar to arrangements in FIG. 12A through FIG. 12D, wherein removal of a cap for a pill bottle was detected and considered as a contextual indication that a pill may have been dispensed and administered. In addition, a contextual acoustic emission for opening a single-use container may be interpreted as providing greater confidence of use of a medication than may be so for a reusable container; where a user may fidget with a reusable container, for example loosening and tightening or removing and replacing the container cap therefor, the container cap for a single-use container may not be replaceable (e.g., as shown previously in FIG. 19B). If opening a container in some sense destroys the container, such as may be true with a single-use container, users may be less likely to open such single-use containers except when preparing to dispense medication; thus, an indication that such a container has been opened may reliably indicate at least an intent to use the medication therein.

While the destructive acoustic emitters shown and described with regard to FIG. 19A through FIG. 19C produce acoustic emissions before medication is dispensed (in opening the container, in the example shown), arrangements wherein acoustic emissions are produced through destruction of emitters during and/or after dispensing medication also may be suitable. For example, a hypodermic injector may incorporate a frangible stem that breaks making an audible noise as the plunger is depressed and/or as the plunger is withdrawn. Such destructive acoustic emissions may for example also perform additional functions; for example, destruction of a plunger for a hypodermic injector may for example render that injector non-functional, thus making re-use of the injector impossible or at least more difficult. The single frangible element may in such manner serve both to provide an acoustic indication of adherence to a medical regimen and to restrict health concerns associated with the sharing and/or re-use of needles. Other arrangements likewise may perform multiple functions, not limited to discouraging re-use of hypodermic injectors or other systems.

However, although pairing destructive emitters and single-use containers (and/or other systems) may be suitable for certain embodiments as shown in FIG. 19A through FIG. 19C, neither one requires the other. For example, a single-use container may utilize non-destructive emitters, and/or a reusable container may utilize destructive emitters. Furthermore, in certain embodiments an emitter that is not itself damaged or destroyed (and/or only part thereof is damaged or destroyed) may be actuated through the destruction of some element or structure, either an element of the emitter or some other distinct element. For example, if a filament (e.g., similar to those shown in FIG. 19A through FIG. 19C) is fabricated so as to produce an electrical voltage when distorted and/or broken, distorting and/or breaking that filament may provide power to an LED (such as in FIG. 17A and FIG. 17B), a speaker (such as in FIG. 18A and FIG. 18B), some other element, etc.; in such case the filament may be damaged or destroyed, but the LED, speaker, etc. may remain intact (and at least potentially may be reusable).

Now with reference to FIG. 20A through FIG. 20D, as noted previously with regard to FIG. 19A through FIG. 19C acoustic emissions produced by damaging and/or destroying emitters and/or portions thereof may be substantially simultaneous, such that the acoustic emissions may overlap one another (and that such overlap of multiple sounds may represent at least a portion of the characteristics of acoustic emissions). However, as may be seen in FIG. 20A through FIG. 20D acoustic emissions produced destructively are not required to be simultaneous or nearly so, and also may be produced in series or otherwise non-simultaneously.

In FIG. 20A, a single-use container 2032A is shown. A container cap 2040A is also shown, and the container 2032A and container cap 2040A are shown to be engaged via three acoustic emitters 2018A1, 2018A2, and 2018A3 in the form of two filaments and a nozzle (though such structures are examples only).

In FIG. 20B, a container cap 2040B is shown partly separated from a container 2032B, as may occur as part of a sequence of events in removing that container cap 2040B preparatory to dispensing medication from the container 2032B. One acoustic emitter in the form of a filament (no longer individually numbered) formerly extending from container 2032B to container cap 2040B is shown as having been broken, and as emitting a characteristic acoustic emission 2020B1. Two remaining acoustic emitters 2018B2 and 2020B3 are shown as deformed but as-yet intact.

FIG. 20C shows a container cap 2040C progressively more separated from a container 2032C. A second acoustic emitter in the form of a nozzle (no longer individually numbered) is also shown as having been broken, and as emitting a characteristic acoustic emission 2020C2. One remaining acoustic emitters 2020C3 is shown intact.

In FIG. 20D, a container cap 2040D is shown separated from a container 2032D. Three broken acoustic emitters (not individually numbered) are shown; one in the form of a filament (e.g., the most recently broken) is shown as emitting an acoustic emission 2020D3.

If FIG. 20A through FIG. 20D are considered as a series, then it may be seen that three acoustic emissions 2020B1, 2020C2, and 2020D3 are produced by the destruction of three acoustic emitters (initially numbered 2018A1, 2018A2, and 2018A3). The acoustic emitters break in series one after another, and thus the acoustic emissions 2020B1, 2020C2, and 2020D3 are produced in series one after another. Such a series of three particular noises may provide a reliable indication that a container cap has been removed from a single-use container of medication. The sequence itself—e.g., acoustic emission 2020B1, followed by acoustic emission 2020C2, followed by acoustic emission 2020D3—may be considered as a feature in determining whether sounds received (e.g., in a station, not shown) represent opening such a container, and/or in excluding background noise as false positives.

In addition, when multiple acoustic emissions 2020B1, 2020C2, and 2020D3 are produced (regardless of whether the emitters therefor are destroyed in the process or not), relationships among those multiple acoustic emissions 2020B1, 2020C2, and 2020D3 also may be considered. For example, as noted, the order of the acoustic emissions 2020B1, 2020C2, and 2020D3 may be considered. Similarly, the timing of acoustic emissions 2020B1, 2020C2, and 2020D3 may be considered. For instance, for certain embodiments the interval between acoustic emissions 2020B1 and 2020C2 may be anticipated as being similar in length to the interval between acoustic emissions 2020C2 and 2020D3 (e.g., assuming a uniform rate of motion in removing the container cap and similar spacing between emitters). In addition, or instead, the lengths of such intervals themselves may be considered. For example, it may be that in opening a given configuration of container the typical interval between acoustic emissions 2020B1 and 2020C2 may be approximately 50 milliseconds. In such instance, if two sounds were detected that were otherwise similar two acoustic emissions 2020B1 and 2020C2 but that exhibited an interval of significantly less than or more than 50 milliseconds, a low confidence may assigned that those two sounds actually represent acoustic emissions characteristic of opening a container. Other features, such as ratios of intervals to one another, etc., also may be considered.

Figure 21:
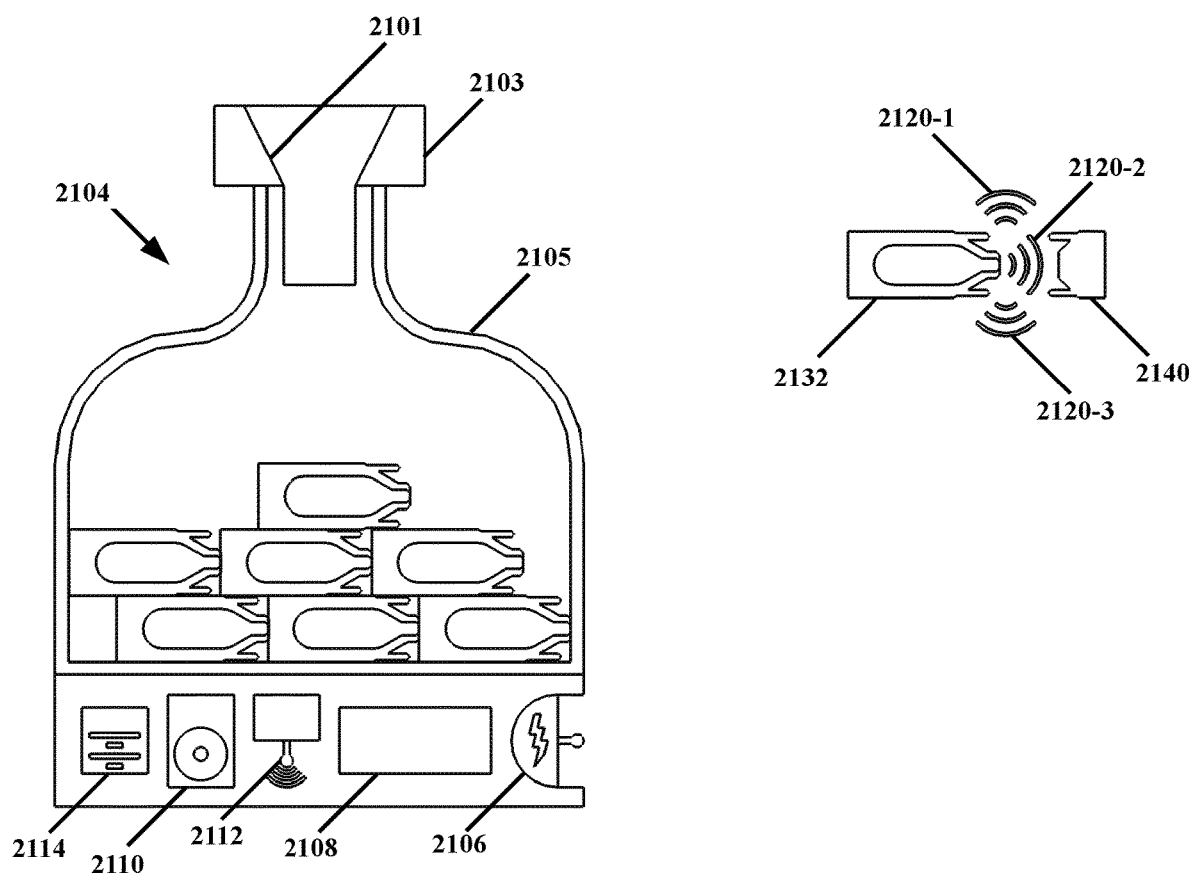
FIG. 21 depicts an example station adapted to fulfill additional functions beyond acoustic reception, in cross-section view.

Now with regard to FIG. 21, in certain previous examples reference has been made to a station as may detect acoustic emissions from a remote and/or a container lacking a remote (and/or wherein the container itself may be considered as a remote). However, while a station may carry out functions related to detecting acoustic emissions, interpreting acoustic emissions, etc., stations are not limited only to such functions. For example, a smart phone or other portable electronic device may be suitable for use as a station, and may continue to carry out functions for which that smart phone is adapted even while serving as a station. In addition, even for a station that is at least nominally dedicated to serving as a station (e.g., a device purpose-built for detecting such acoustic emissions), other functions still may be carried out thereby.

In FIG. 21 a single-use medication container 2132 is shown. A container cap 2140 is shown separated from the container 2132, and three acoustic emissions 2120-1, 2120-2, and 2120-3 are shown being produced. (Such an arrangement may be at least somewhat similar to that shown in FIG. 19A through FIG. 19C).

FIG. 21 also shows a station 2104. As in certain previous examples, the station 2104 is shown to include an acoustic receiver 2106, a processor 2108, a data store 2110, a communicator 2112, and a power supply 2114 (though as already noted, such elements are themselves examples only and may not necessarily be present or required for all embodiments). In addition, the station 2104 in FIG. 21 includes a bin 2105 in the form of a narrow-mouth jar; the bin 2105 is shown as having a number of opened medication containers therein (not individually numbered). The station 2104 also includes a bin lid 2103, and a bin chute 2101. The top of the bin chute 2101 as shown is approximately conical in shape, narrowing at the bottom thereof. Given the configuration of the bin chute 2101, bin lid 2103, and bin 2105 of the station 2104 an expended single-use container dropped into the bin chute 2101 may be deposited within the bin 2105.

The acoustic receiver 2106 may detect acoustic emissions 2120-1, 2120-2, and 2120-3 as produced by the container 2132; as may be understood from the lightning bolt depicted on the acoustic receiver 2106, in FIG. 21 the acoustic receiver 2016 is active in receiving the acoustic emissions 2120-1, 2120-2, and 2120-3. Consequently, the station 2104 as a whole may identify the acoustic emissions 2120-1, 2120-2, and 2120-3, may register events, take further action based thereon, etc.

However, the station 2104 also may perform additional functions. As shown in FIG. 21 the bin 2105 of the station 2104 accepts and accommodates therein expended single-use medication containers. In at least certain instances, it may be desirable to retain and/or to segregate "the empties" in some fashion. For example, during clinical testing of a new medication, a new single-use container, etc., it may be useful to examine used containers to evaluate matters such as how much medication was dispensed, how effectively the containers opened (e.g., did a frangible nozzle tear in the intended manner), etc. Such features may be performed passively; that is, no additional active components may be required in a station 2104 that merely collects and stores expended containers, and no additional functions may be required of components already present in the station 2104.

However, in other embodiments additional active functions may be performed. For example, if an expended container deposited in the bin 2105 makes a detectable sound (e.g., upon hitting the bottom of the bin 2105), the acoustic receiver 2106 may be utilized to receive that sound. In certain embodiments the sound of disposing of the empty container may be considered as an acoustic emission unto itself (in place of or in addition to acoustic emissions produced by opening a container, dispensing medication, etc.). "Container disposal" may be utilized and considered as yet another form of contextual event, associated with the use of at least certain medications.

Furthermore, it may be suitable to include additional active components in some embodiments. As may be seen in FIG. 21, the station 2104 therein already includes a power supply 2114, communicator 2112, data store 2110, and processor 2108; such elements may serve as infrastructure in supporting additional sensors and/or other components. For example, a weight sensor or impact sensor in the base of the bin 2105 may serve to determine the weight of expended containers deposited in the bin 2105; if the empty weight of the containers is known, the weight of medication remaining may be determined. Alternately, the simple presence of an impact may serve as an indication that an expended container has been deposited in the bin, serving as a contextual indication of medication use (though not necessarily being passive in the same sense as a whistle produced when a user squeezes a medication container, etc.). Similarly, photosensors, capacitive sensors, etc. disposed in and/or near the bin lid 2103, the bin chute 2101, etc., may be used to determine whether empty containers are being deposited, other information about those containers such as how much medication remains therein (e.g., through light transmission through the container), etc.

Such additional active and/or functions may be supported by already-existing elements of at least some stations. However, while such functions are not prohibited, neither are additional functions necessarily required for any given embodiment.

Figure 22:
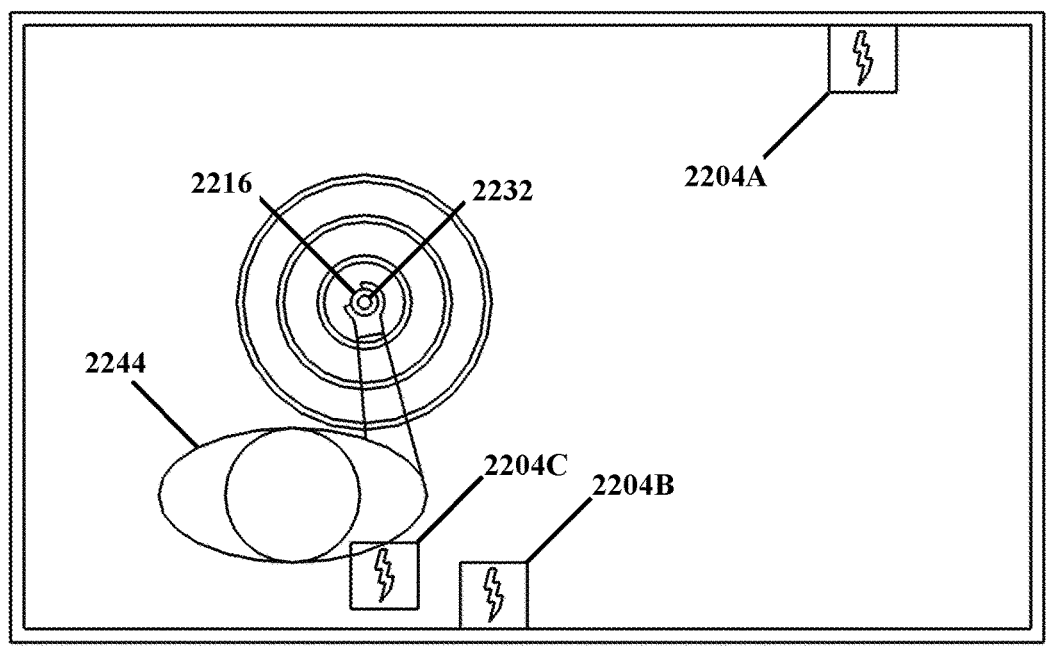
FIG. 22 depicts multiple stations and an example remote as may be utilized, in top-down view.

Now with reference to FIG. 22, embodiments are not limited with regard to the form and/or number of stations that may cooperate with a remote. For example, the example arrangement of FIG. 22 depicts a remote 2216 in the hand of a user 2244, and a container 2232 engaged with the remote 2216. The remote 2216 is depicted to be producing an acoustic emission 2220. In addition, three stations 2204A, 2204B, and 2204C are shown. Stations 2204A and 2204B are shown at some distance from the user 2244; for example, stations 2204A and 2204B may be dedicated systems, such as electronic devices adapted to be deployed within a room or other space specifically for the purpose of detecting and processing an acoustic emission 2220. Alternately, stations 2204A and 2204B may be multi-purpose devices as may incidentally be present, such as a desktop PC, laptop PC, game system, smart television, etc.; so long as the necessary functionality is enabled, the types of devices as may serve as stations are not limited.

Station 2204C is shown in contact with the user 2244, for example as may be disposed within a pocket or bag, otherwise carried by the user, etc. Such stations may include, but are not limited to, phones, smart watches, other portable electronic devices, etc. While portable and/or user-carried/worn stations such as 2204C may be non-dedicated, such as devices that a user 2244 may carry for other purposes (such as a phone), the use of dedicated portable stations 2204C specifically adapted to function as stations also may be suitable. In addition, while FIG. 22 shows only one station 2204C disposed on a user 2244, the use of two or more portable stations disposed on the user 2244 and/or on some other person also may be suitable. For example, if two people are present, each carrying a phone as may be suitable as a station, one or both such phones may function as a station in cooperation with a remote. In particular, systems on the person of individuals other than the user 2244 may serve as stations, in addition to or instead of a system on the person of the user himself/herself.

As may be seen in FIG. 22, the stations 2204A, 2204B, and 2204C are active (as indicated by the lightning bolts shown thereon). Thus, 2204A, 2204B, and 2204C may be understood as receiving the acoustic emission 2220, processing that acoustic emission, attempting to detect the acoustic emission, etc. The use of multiple stations 2204A, 2204B, and 2204C as shown in FIG. 22 may facilitate certain functions. For example, if one such station does not receive or identify the acoustic emission 2220 (e.g., due to distance, intervening sound-absorbing obstacles, background noise, etc.) another station may do so, providing redundancy. Similarly, if two or more stations do receive a given acoustic emission 2220, then the confidence that an acoustic emission 2220 has been produced (and thus that the relevant medication has been dispensed) may be greater than for only one station. In addition, if multiple stations receive an acoustic emission 2220, such stations may cooperate to determine features such as the location of the remote 2216 when the acoustic emission 2220 was produced. For example, if the stations 2204A, 2204B, and 2204C shown in FIG. 22 have receivers adapted to determine a relative direction of the source of the acoustic emission 2220 relative to those receivers, then the position of the source (i.e., the remote 2216) may be triangulated. Similarly, if the time of receipt at each station 2204A, 2204B, and 2204C may be determined with sufficient precision, it may be possible to determine where the acoustic emission 2220 originated based on time-of-flight. Other functions also may be enabled.

In addition, for at least certain embodiments multiple stations may cooperate. For example, stations may communicate wirelessly or via other avenues, sharing information, combining received data regarding acoustic emissions to make determinations as to whether an emission is characteristic, comparing received data to reject background noise (e.g., stations at different locations may not receive the same background noise), registering events and/or other information in multiple stations even if an acoustic emission was only determined at one station, etc. Other cooperative functions also may be suitable, and cooperation among stations (or likewise among remotes) is not limited.

Figure 23:
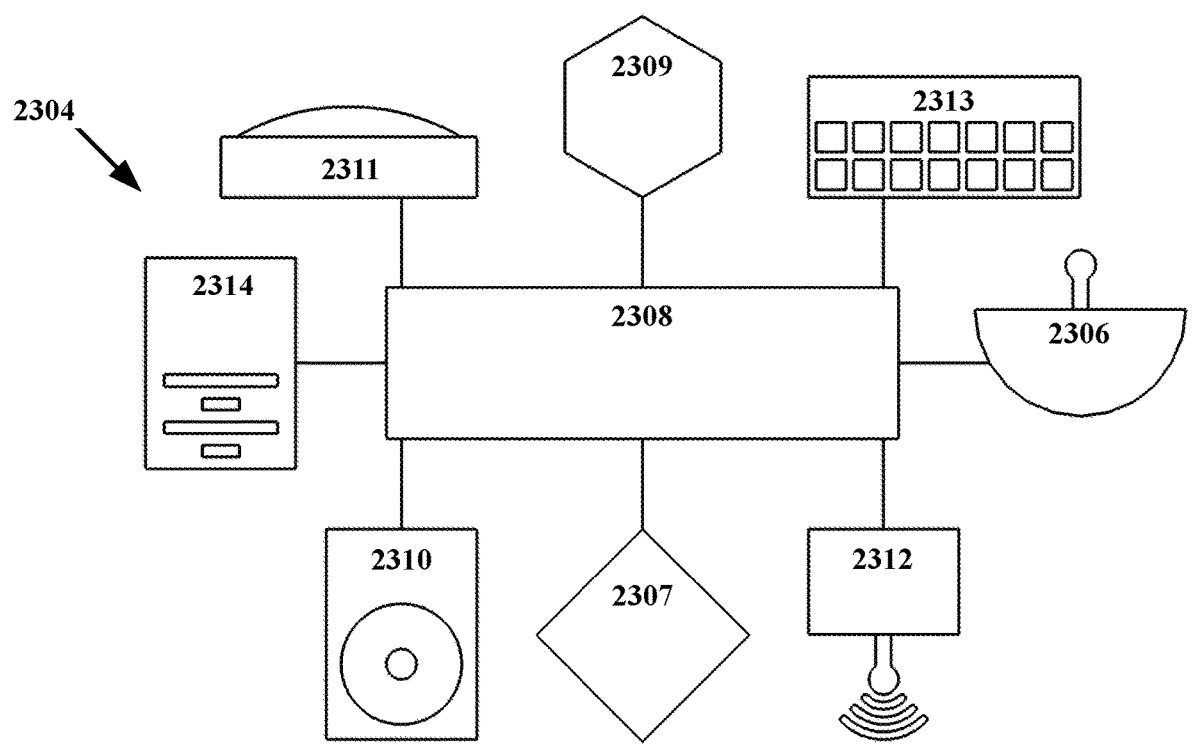
FIG. 23 depicts another example station, in schematic view.

Turning to FIG. 23, while certain elements as may be present in a station 2304 have been shown and described previously, for example in FIG. 3, other elements also may be present, and embodiments are not limited with regard to what elements are (or are not) present within a given station 2304. FIG. 23 shows certain additional elements as may be (but are not required to be) present in a station 2304.

The station 2304 as illustrated includes an acoustic receiver 2306, adapted to receive acoustic emissions, and a processor 2308 in communication with the receiver 2306. A power supply 2314, data store 2310, and communicator 2312 also are shown.

In addition, the example station 2304 includes a GPS 2307, adapted to determine a location of the station 2304 at a given time. For example, the location at which a user dispenses medication (as determined by the location at the time a characteristic acoustic emission is received) may be determined through the GPS 2307. Also, data from the GPS 2307 may be considered for other purposes. For example, typically it may be expected that a user may dispense eye drops while at least approximately stationary, such as sitting, standing, etc. If the GPS 2307 were to indicate that a user is moving at a walking or running pace, it may be unlikely that the user is dispensing eye drops at that time, regardless of what acoustic emissions may have been received. Thus, environmental factors may be considered in determining confidence as to whether a medication has been properly dispensed. Other determinations of position/motion (e.g., from receivers adapted to determine the direction from which an acoustic emission was received) likewise may be considered. Similarly, output from accelerometers, gyros, temperature or humidity sensors, etc., may be considered as well in determining whether a medication has been dispensed.

The station 2304 as shown also includes a direction finder 2309. For example, the direction finder 2309 may be adapted to determine the direction from which an acoustic emission originated, relative to the station 2304. It is noted that in at least certain instances a direction finder 2309 may be integrated into a receiver 2306, for example in the instance of a directional microphone. However, while such integration is not prohibited, neither is such integration required.

The station 2304 may include a display 2311. For example, the display 2311 may show information related to the dispensing of medication. The display 2311 may show confirmation that an acoustic emission has been detected, a listing of previous acoustic emissions, a visual reminder that a user is due for their next dose of medication, an advisory that medication is running low, etc. The type and extent of information as may be displayed is not limited. In addition, the nature of the display 2311 is not limited, either with regard to form or complexity. For example, a display may be a simple tell-tale such as an LED that flashes green to indicate that medication has been dispensed. However, suitable displays may be more sophisticated, including but not limited to alpha-numeric displays, CRT or LED screens, etc. In addition, while the term display 2311 may suggest visual output, suitable displays are not limited only to visible displays; for example, an audio speaker that provides a reminder chime to take medication, or that plays a voice message confirming that medication has been taken, etc., also may be suitable.

In addition, the station 2304 may include a user interface 2313 as shown in FIG. 23. For example, the user interface 2313 may enable input from a user to the station 2304. Thus for at least certain embodiments a user may add or delete characteristic emissions of interest (e.g., if the user begins taking a new medication or ceases to take an old one), to call up data for review, to change user preferences, etc. As with displays 2311, user interfaces 2313 may be simple (such as one or more individual buttons) or complex (such as a touch screen or voice input system), and are not limited with regard to form, complexity, etc.

It is noted that certain existing systems, including but not limited to smart phones, may already include some or all of the elements shown in FIG. 23. For example, a smart phone may include a processor, directional microphone, power supply, data store, communicator, GPS, display, user interface, etc. While use of such devices as stations in cooperation with remotes is not prohibited, and in at least certain instances may be advantageous (e.g., being already available to or in possession of certain patients), neither is it required to use smart phones as stations.

Thus, it may be useful in at least certain instances to consider remotes (and/or emitters, for embodiments that may not include a distinct remote such as shown in FIG. 12A through FIG. 12D) and stations separately. Different remotes and stations may be "mixed and matched"; it is not necessary for a given remote to be exclusively in cooperation with a given station, or vice versa. A single station may detect acoustic emissions from many remotes, and likewise may remotes may detect acoustic emissions from a single remote.

Figure 24:
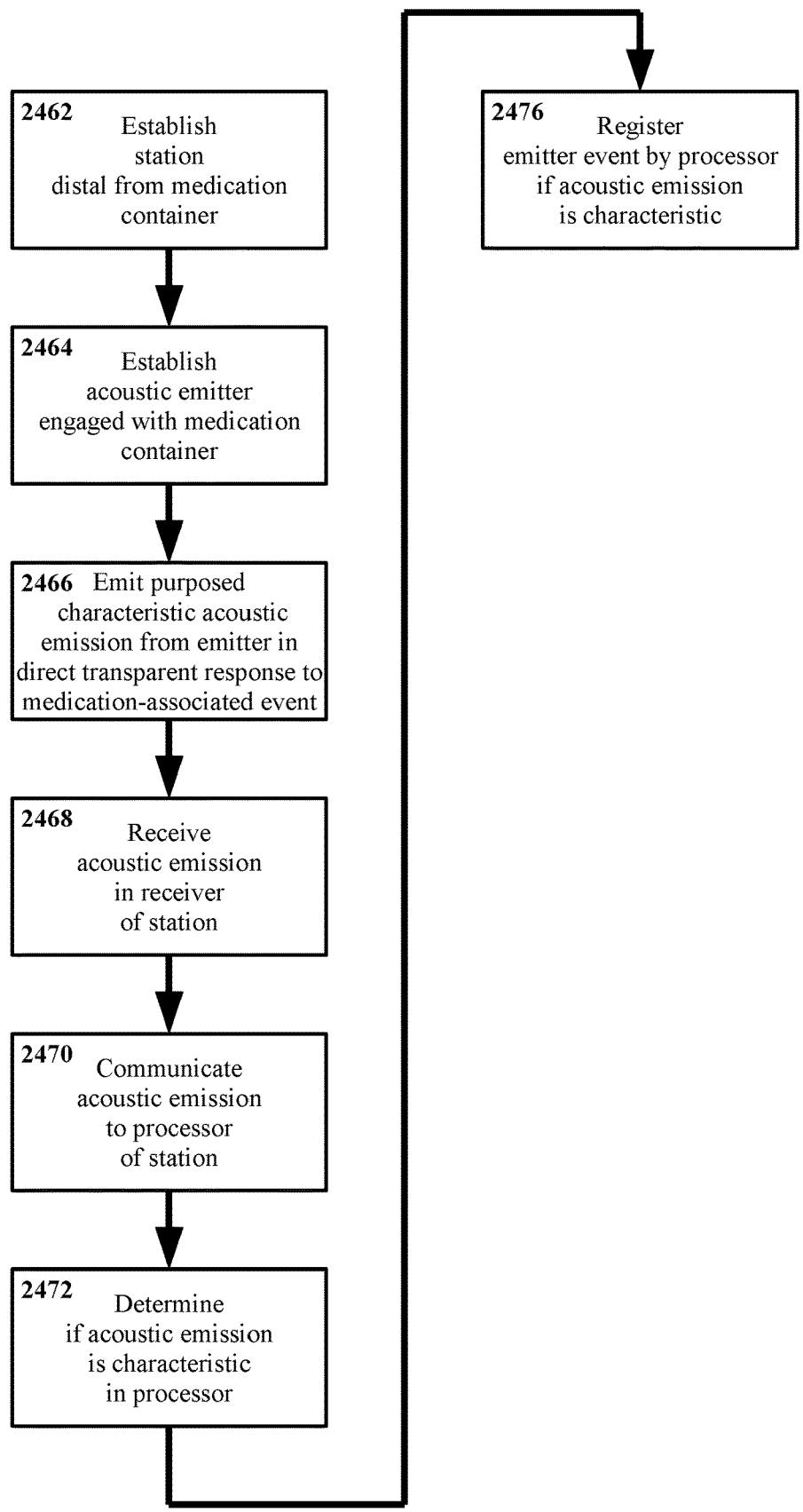
FIG. 24 depicts an example method for determining the use of a medication through transparent consequential characteristic emissions absent a remote, in flow chart form.

Now with reference to FIG. 24, as previously noted (e.g., with regard to FIG. 4) example methods may utilize remotes to determine the dispensing and/or use of medication through transparent and consequential response to some event. Certain previous examples herein have addressed the use of remotes for producing evidence of the event, such as an acoustic emission caused by compressing a remote equipped with a whistle. Such events, being associated with a remote, may be referred to as "remote events". (It is noted that the term "remote event" does not necessarily refer to remoteness in the sense of distance, but may instead refer to the use of a mechanism referred to herein as a remote. Nevertheless, a remote producing an acoustic emission may indeed be at some distance from, for example, a station receiving that acoustic emission.)

However, while the use of a remote may be suitable for certain embodiments, use of a remote is not necessarily required. For example, as shown in FIG. 12A through FIG. 12D, an acoustic emission may be produced without a remote that is distinct from a container. An acoustic emitter may be integrated into a container, so that functionality is obtained without the use of a remote. An example method for such an arrangement is shown in FIG. 24.

In the method of FIG. 24, a station is established 2462 at some location distal from a medication container. An acoustic emitter is established 2464 at some location proximate the medication container. As shown and described previously herein, establishing an acoustic emitter 2464 may include establishing a remote and engaging that remote with the medication container; however, not all embodiments necessarily require a remote as such.

In a consequential and user-transparent response to some event affecting the acoustic emitter (and typically the medication container), and in association with dispensing medication, a purposed characteristic acoustic emission is emitted 2466 from the acoustic emitter. Such an event may be referred to as an emitter event; an emitter event may be considered as similar to a remote event, and indeed certain remote events may also be emitter events. For example, if a whistle is used as an acoustic emitter, and an acoustic emission therefrom is to be received and considered, it may be reasonable to refer to the event producing that acoustic emitter as an emitter event (being produced due to an event happening to the emitter) or in some instances equivalently as a remote event (being produced due to an event happening to the remote, and thus also to the emitter). However, where reference to a remote event may assume the presence of a remote, reference to an emitter event does not so presume that a remote exists.

As with remote events, emitter events may be produced as a result of dispensing or using a medication, or as a result of some contextual action. For example, in the arrangement of FIG. 12A through FIG. 12D acoustic emissions are produced as the cap of a medication container is removed and replaced, rather than as medication is dispensed per se; such acoustic emissions may be understood as contextual to dispensing medication.

Still with reference to FIG. 24, the acoustic emission is received 2468 in the receiver of the station. The acoustic emission is communicated 2470 to the processor of the station. Within the processor, a determination is made 2472 as to whether the acoustic emission that has been received is indeed characteristic of the emitter. If the acoustic emission is determined 2472 to be characteristic of the emitter, then an emitter event is registered 2476 by the processor. That is, if the processor determines that the emitter has made its characteristic sound, it is considered that an event that would cause that sound has taken place, and the event may be stored in a data store, transmitted to some recipient, etc. Thus, if the event in question is associated with dispensing medication, then it may be considered that the medication has been dispensed, etc.

In comparing FIG. 4, FIG. 5, and FIG. 24 (and certain subsequent figures herein) it may be noted that embodiments of a method may similar despite variations in the specifics of the emitter and/or station. For example, whether a remote is present (e.g., FIG. 4 and FIG. 5) or not (e.g., FIG. 24), or whether a station is a smart phone (e.g., FIG. 5) or not (as is unspecified by but encompassed within FIG. 4 and FIG. 24), embodiments of methods may be carried out regardless. Thus, embodiments may be independent of at least certain particulars of emitter/remote and station; a given station may function regardless of whether a remote or an emitter is present (or what sort of remote or emitter is present), a given remote or emitter may function regardless of whether a station is a smart phone or a dedicated device, etc.

Figure 25:
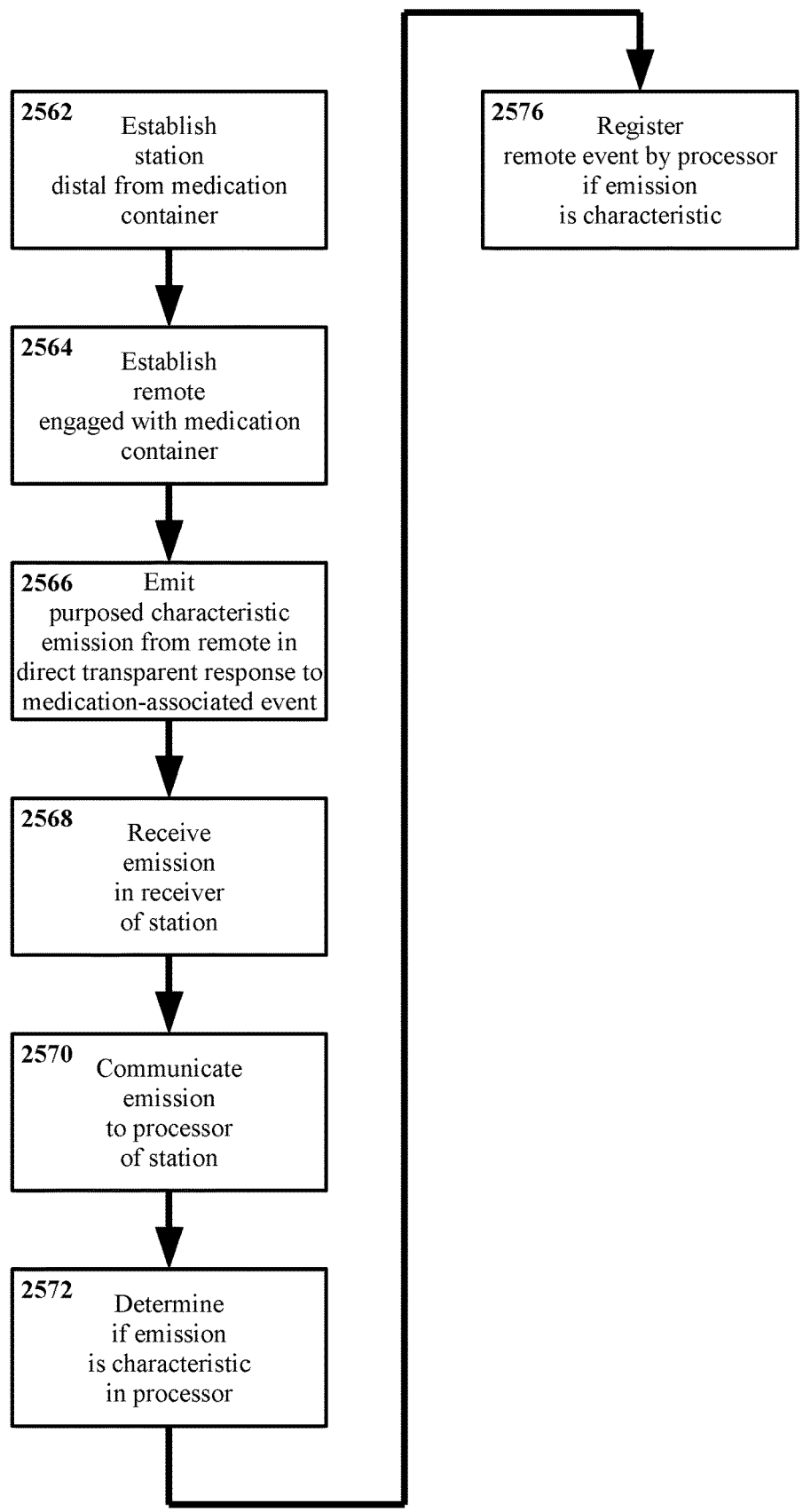
FIG. 25 depicts an example method for determining the use of a medication through transparent consequential characteristic non-acoustic emissions, in flow chart form.

Now with reference to FIG. 25, methods may utilize acoustic emissions in determining the dispensing and/or use of medication through transparent and consequential response to some event. However, for example as noted with regard to FIG. 18A and FIG. 18B, non-acoustic emissions, including but not limited to optical emissions such as visible light, infrared light, etc., also may be suitable In the method of FIG. 25, a station is established 2562 at some location distal from a medication container. A remote is established 2564 at some location proximate the medication container. (As noted previously with regard to FIG. 24, for certain embodiments it may be suitable to establish an emitter without a remote.) In a consequential and user-transparent response to some event affecting the remote, and in association with dispensing medication, a purposed characteristic emission is emitted 2566 from the remote. The characteristic emission may be entirely acoustic, but other arrangements also may be suitable. For example, an emission may include both acoustic and optical portions. Such an arrangement may for example enable a convenient determination of distance between a remote and a station. For example, if a light component of an emission and a sound component of an emission are produced together in time, the distance between the remote producing the emission and a station receiving that emission may be determined through measuring the time elapsed between receipt of the light component and receipt of the sound component. (This may be analogous to approximating distance to a lightning strike through counting the seconds between the visible flash and the audible thunder.) Alternately, all-optical emissions may be suitable, as may other non-acoustic emissions. The type of characteristic emissions are not limited.

Still with reference to FIG. 25, the emission is received 2568 in the receiver of the station. The emission is communicated 2570 to the processor of the station. A determination is made 2572 as to whether the emission is characteristic of the emitter. If the emission is determined 2572 to be characteristic of the emitter, then a remote event is registered 2576 by the processor.

Figure 26:
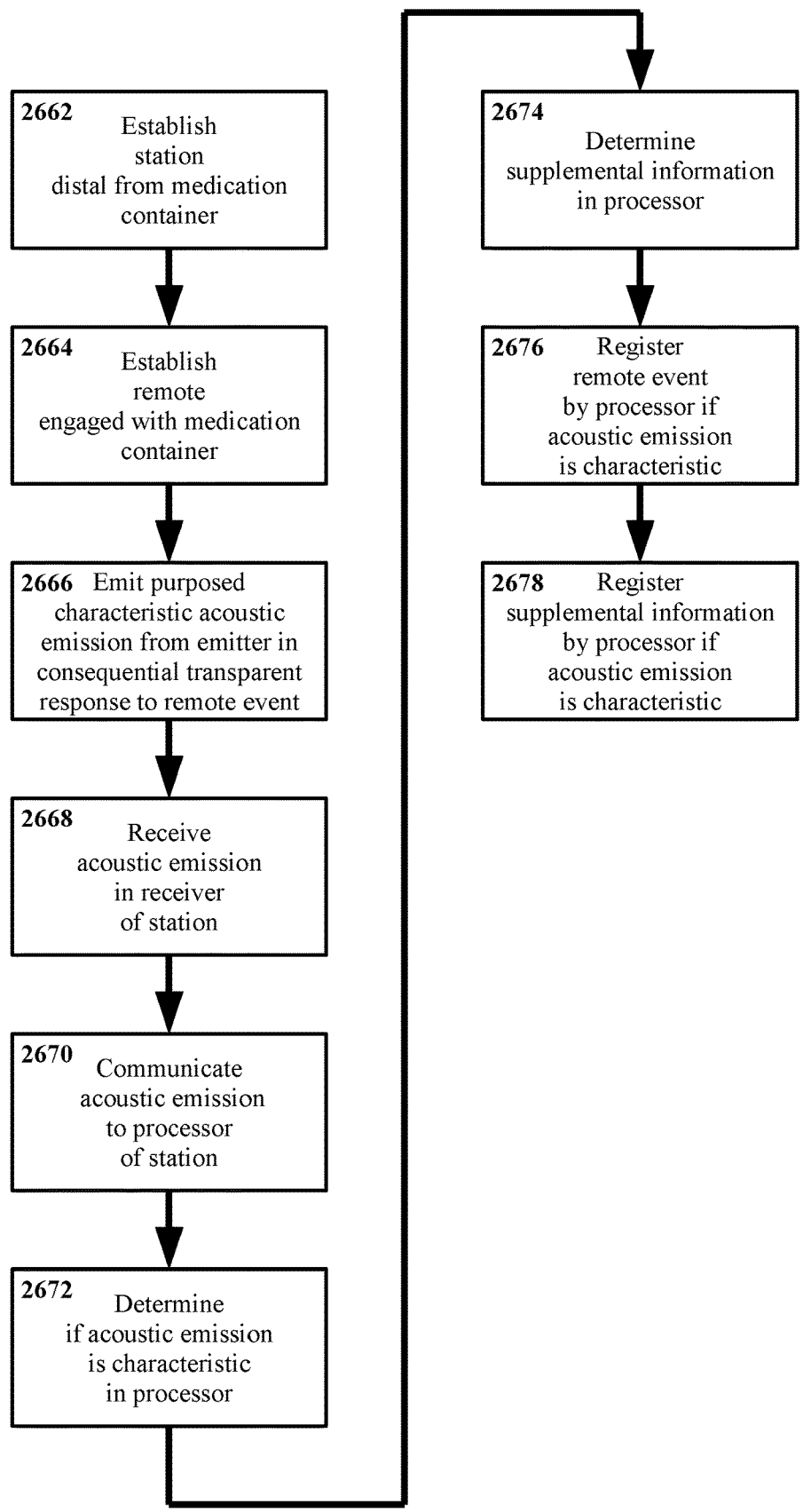
FIG. 26 depicts an example method for determining the use of a medication through transparent consequential characteristic emissions and determining supplemental information, in flow chart form.

Now with reference to FIG. 26, as described previously embodiments may include registration of events, such as recording that a medication has been dispensed in a data store, displaying that the medication has been dispensed on a screen, etc. However, the information registered is not limited only to the fact of the event, and other information also may be registered.

In the example of FIG. 26, a station is established 2662 at some location distal from a medication container. A remote is established 2664 at some location proximate the medication container. In a consequential and user-transparent response to some event affecting the remote, and in association with dispensing medication, a purposed characteristic acoustic emission is emitted 2666 from the remote. The acoustic emission is received 2668 in the receiver of the station, and is communicated 2670 to the processor of the station. A determination is made 2672 as to whether the emission is characteristic of the emitter.

In addition, supplemental information also may be determined 2674 in the processor. For example, the time at which the acoustic emission—in this example, referred to as the remote event—was received by the station may be determined (e.g., from a clock on-board the processor, from some external source in communication with the processor, etc.). This time may be referred to as the remote event time. The precise manner in which a remote event time is determined is not limited; a remote event time may be defined as the time that the acoustic emission was detected, the time that the acoustic emission was confirmed as being characteristic of the remote/emitter, or in some other manner. Similarly, additional supplemental information regarding the dispensing of medication may be determined, such as the dosage dispensed (e.g., as noted with regard to FIG. 14A through FIG. 14D).

Other supplemental information regarding the acoustic emission may be determined. For example, the wave form of an acoustic emission may be measured and communicated to the processor. Such an action may not require additional steps; determination of whether the acoustic emission may for example be based in whole or in part on consideration of the wave form, whether that wave form matches some standard therefor, etc. However, performing additional steps in acquiring such supplemental information, while not required, is not prohibited.

Supplemental information regarding processing of the acoustic emission also may be determined. For example, if a confidence value is computed for or otherwise assigned to a given acoustic emission (e.g., 92% confidence that the received acoustic emission is characteristic), that confidence value also may be regarded as supplemental information.

Furthermore, information not immediately related to the remote event may be determined. For example, environmental information such as the temperature, humidity, light level, level of background noise, etc., may be determined. Information regarding the user also may be determined, such as how the user is moving, the user's body temperature, etc. Such supplemental information may be determined using sensors on the station. For example, considering a smart phone as a station, certain smart phones may include sensors adapted to measure temperature, background noise, etc. If a smart phone is employed as a station, and may be determined (or assumed) to be on the person of the user, then such a station also may measure properties of the user such as body temperature, other biometrics, the position, speed, etc. of the user (e.g., through on-board gyros and accelerometers), and other phenomena. However, such supplemental information is not limited to being determined only by a smart phone, only from a station disposed on the person of a user, or by any station.

The content of supplemental information and manner of determining supplemental information is not limited.

Continuing in FIG. 26, if the emission is determined 2672 to be characteristic of the emitter, then a remote event is registered 2676 by the processor. Similarly, if the emission is determined 2672 to be characteristic some or all of the supplemental data may be registered 2678. Like registration 2676 of the remote event, registration 2678 of supplemental information is not limited, and may include but is not limited to display, storage, and communication. In addition, it is noted that not all supplemental information determined 2674 necessarily must be registered 2678 in a given embodiment. For example, a waveform for an acoustic emission may be determined as supplemental information and a confidence level assigned thereto, but this does not impose any requirement for the waveform or confidence level to be outputted to a display, recorded in a data store, or otherwise registered.

In addition, as previously noted with regard to registering remote events, registration of supplemental information if an acoustic emission is characteristic does not exclude the possibility of registering supplemental information even if an acoustic emission is received but found not to be characteristic, or if no acoustic emission is received. For example, considering a smart phone as a station, it may be suitable to record the degree of motion of the smart phone over time on an ongoing basis regardless of whether an acoustic emission is received. If the smart phone is completely stationary for some period, it may be considered that the smart phone is not being worn or carried by the user during that time. In such instance, it may be inferred that the user may be away from their phone and that medication may have been dispensed during the period even though that dispensing of medication was not detected, that the user may be asleep, etc. While such information may not directly indicate that medication was or was not dispensed, nevertheless such information may still be of use in evaluating the overall usage of medication over a period of time. Thus, information may be registered even if no emission is received that is determined to be characteristic of a given remote.

Figure 27:
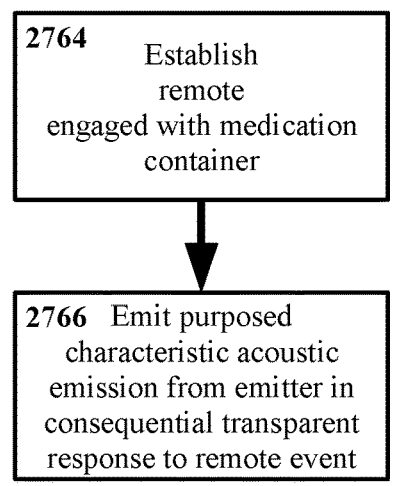
FIG. 27 depicts an example method for indicating use of a medication through producing transparent consequential characteristic emissions, in flow chart form.
Figure 28:
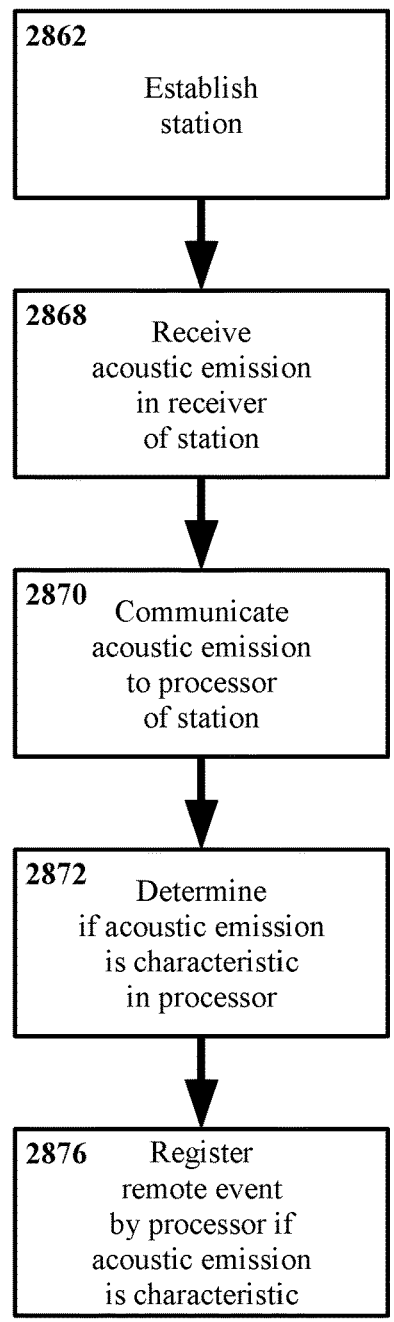
FIG. 28 depicts an example method for identifying use of a medication through receiving characteristic emissions, in flow chart form.

Turning to FIG. 27 and FIG. 28, as noted previously (e.g., with regard to FIG. 23 and FIG. 24) embodiments are not necessarily required to match a given remote with a given station, or vice versa. Indeed, embodiments of a remote may be considered as distinct devices from any station as may cooperate therewith, and embodiments of a station likewise may be considered as distinct devices from any remote as may cooperate therewith. Similarly, producing the acoustic emission (e.g., dispensing medication) and evaluating the acoustic emission (e.g., registering that medication has been dispensed) may be considered separately from one another.

Specifically, with reference to FIG. 27, therein an example method for indicating use of a medication through producing transparent consequential characteristic emissions is shown. In the example method shown an acoustic emission indicative of some event such as a medication being dispensed is produced, however the interpretation of that acoustic emission is not shown. Thus FIG. 27 may be considered as addressing use of a remote (or similarly an emitter) as a distinct device.

In the example of FIG. 27, a remote is established 2764 engaged with (or at least in proximity to) a medication container. In a consequential and user-transparent response to some event affecting the remote, and in association with dispensing medication, a purposed characteristic acoustic emission is emitted 2766 from the remote.

Typically, though not necessarily, the acoustic emission then may be received, evaluated, etc. elsewhere, such as in a station. However, it may be suitable for at least some embodiments to focus on the production of an acoustic emission that indicates medication has been dispensed, used, prepared for use, etc., without also considering in detail the subsequent processing of that acoustic emission.

Conversely with reference to FIG. 28, therein an example method for determining use of a medication through receiving characteristic emissions is shown. In the example method shown an acoustic emission is received and interpreted, however the production of that acoustic emission is not shown. Thus FIG. 28 may be considered as addressing use of a station as a distinct device.

In the example of FIG. 28, a station is established 2862. A characteristic acoustic emission is received 2868 in the receiver of the station, and is communicated 2870 to the processor of the station. A determination is made 2872 in the processor as to whether the emission is characteristic. For example, the station may have some standard for evaluating acoustic emissions, some algorithm for comparing emissions to that standard, etc. However, the particulars of what may have generated any given acoustic emission may or may not be addressed by the station. Continuing in FIG. 28, if the emission is determined 2872 to be characteristic, then an event is registered 2876 by the processor. Again, the nature of the event (e.g., medication being dispensed) may not be specified or even considered with regard to the station.

Typically, though not necessarily, characteristic acoustic emissions as received may be anticipated to have been produced by some characteristic source, such as an emitter and/or a remote incorporating an emitter. However, it may be suitable for at least some embodiments to focus on the receipt and evaluation an acoustic emission without concern as to how, why, etc., that acoustic emission may have been produced.

Figure 29:
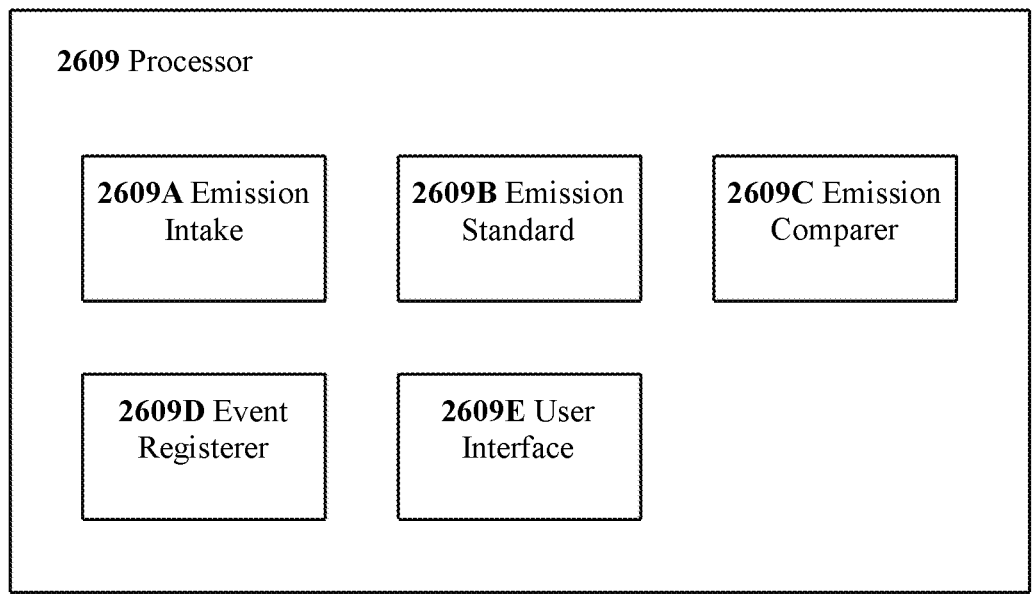
FIG. 29 depicts an example processor adapted for identifying use of a medication through receiving characteristic emissions via data entities instantiated thereon, in schematic view.

Now with reference to FIG. 29, as has been described previously certain functions may be carried out within/by a processor, such as determining whether a received acoustic emission is characteristic of a given emitter. One example approach (though not necessarily the only approach) for implementing such functionality is shown in FIG. 29. Therein, a processor 2908 is shown, as may be similar to processors shown elsewhere herein as being in/on various stations. In addition, the processor 2908 in FIG. 29 is shown with several data entities disposed thereon: an emission intake 2908A, an emission standard 2908B, an emission comparer 2908C, an event register 2908D, and a user interface 2908E. Such data entities may for example include digital data and/or executable instructions instantiated onto the processor 2908. In more colloquial terms, some or all of the data entities 2908A through 2908E may be programs or portions thereof installed onto a processor, such as the processor of a smart phone, etc. (though this is not limiting). Steps of establishing a station may include, for example, instantiating data entities 2908A through 2908E onto a processor, though other arrangements also may be suitable.

In the example of FIG. 29, the emission intake 2908A is adapted to accept an acoustic emission, and/or some signal representing an acoustic emission, into the processor from some external source, such as a microphone or other receiver. For example, the emission intake 2908A may represent one or more device drivers for communicating input from a microphone to a processor, etc.

The emission standard 2908B is adapted to provide guidance in some form as to what may constitute a characteristic acoustic emission. For example, the emission standard 2908B may specify frequency ranges for one or more pitches (e.g., whistle pitches), wave forms, etc. The emission standard 2908B may in at least some sense be considered as a target or template that a received acoustic emission must match in order to be identified as being a characteristic acoustic emission (e.g., characteristic of a particular whistle, etc.) as opposed to background noise, a false positive, etc.

The emission comparer 2908C is adapted to determine whether a given acoustic emission is a characteristic acoustic emission. For example, the emission comparer 2908C may compare frequency ranges of a two-tone whistle pitch to frequency ranges as specified in the emission standard 2908B, may carry out an algorithm to determine whether a waveform for a sound sufficiently matches a specified waveform in the emission standard 2908B to identify that sound as characteristic, etc.

The event register 2908D is adapted to register an event as having taking place if the emission comparer 2908C determines that a received acoustic emission is characteristic. Thus, the event register 2908D may record data indicating that the event (such as dispensing a medication) took place into a data store, may output data regarding the event to a display, may transmit data for the event to some recipient, some combination thereof, etc. Not all embodiments necessarily will exhibit all such functions, for example a station with no display may not benefit from an event register 2908D capable of outputting information to a display, etc.

The user interface 2908E is adapted to accept input from a user, for example regarding functions performed by the station. As a more concrete example, the user interface 2908E may enable a user to enter a query to display all events in the past 30 days, to install a new emission standard 2908B (e.g., for a new remote and/or a new medication), to manually register an event that was erroneously not registered or manually delete an event that was registered by mistake, etc. Again, not all embodiments necessarily will have or must have a user interface, even among those embodiments which utilize data entities as shown in FIG. 29 (which configuration itself is not limiting).

Similarly, various embodiments may have additional data entities and/or other elements. For example, an embodiment may include a data entity adapted to compare the usage of a medication (as determined through receiving acoustic emissions from an emitter on/in the container) against a prescribed regimen for that particular medication and patient, a data entity to communicate such adherence information to some external party such as a medical care provider or clinical research supervisor, a data entity to remind the user to take a medication, a data entity to automatically request a refill of a prescription based on time or quantity remaining, etc. Other arrangements also may be suitable.

Figure 30:
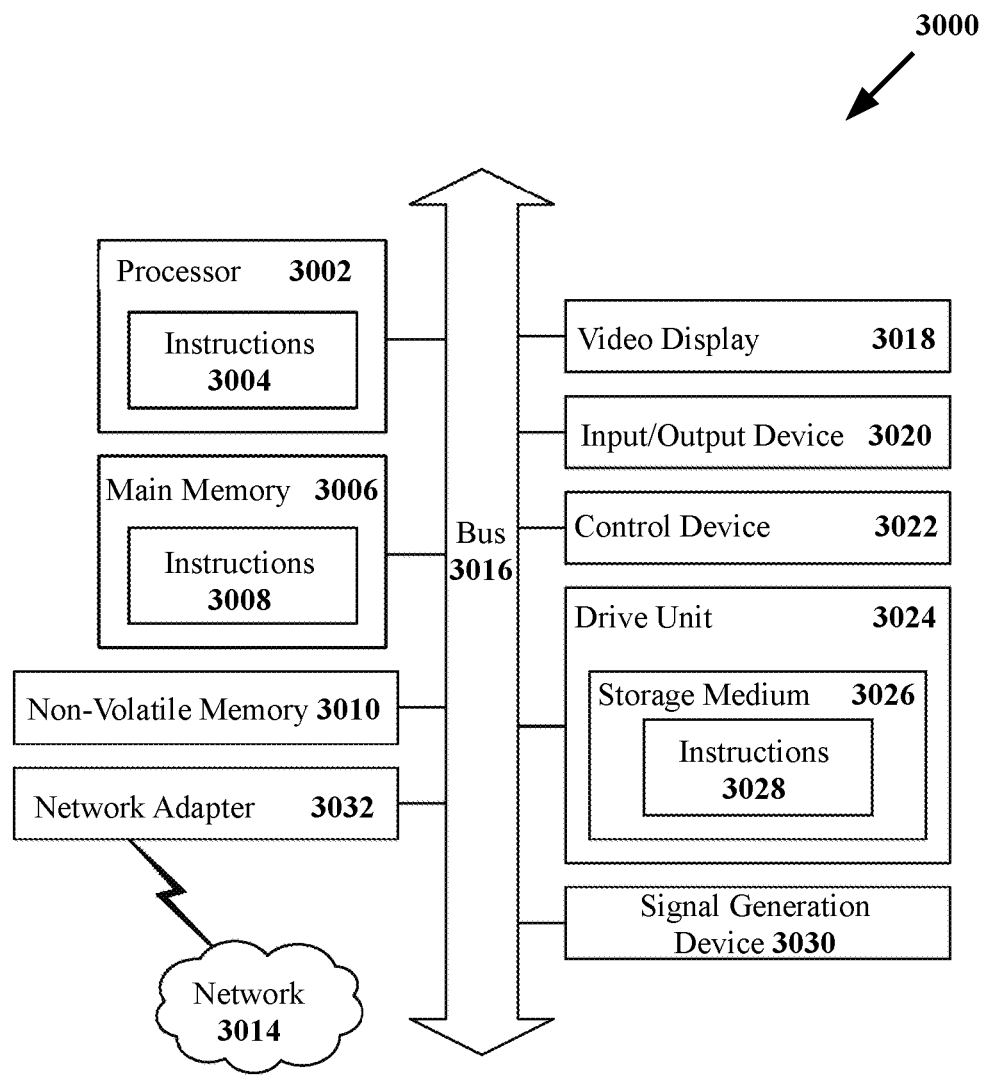
FIG. 30 is a block diagram illustrating an example of a processing system in which at least some operations described herein can be implemented.

FIG. 30 is a block diagram illustrating an example of a processing system 3000 in which at least some operations described herein can be implemented. The processing system may include one or more central processing units ("processors") 3002, main memory 3006, non-volatile memory 3010, network adapter 3012 (e.g., network interfaces), video display 3018, input/output devices 3020, control device 3022 (e.g., keyboard and pointing devices), drive unit 3024 including a storage medium 3026, and signal generation device 3030 that are communicatively connected to a bus 3016. The bus 3016 is illustrated as an abstraction that represents any one or more separate physical buses, point to point connections, or both connected by appropriate bridges, adapters, or controllers. The bus 3016, therefore, can include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

In various embodiments, the processing system 3000 operates as a standalone device, although the processing system 3000 may be connected (e.g., wired or wirelessly) to other machines. For example, in some embodiments components of the processing system 3000 are housed within a computer device used by a user to access an interface having skin care products or skin care regimens, while in other embodiments components of the processing system 3000 are housed within a network-connected container that holds one or more skin care products. In a networked deployment, the processing system 3000 may operate in the capacity of a server or a client machine in a client-server network environment, or as a peer machine in a peer-to-peer (or distributed) network environment.

The processing system 3000 may be a server, a personal computer (PC), a tablet computer, a laptop computer, a personal digital assistant (PDA), a mobile phone, a processor, a telephone, a web appliance, a network router, switch or bridge, a console, a hand-held console, a (hand-held) gaming device, a music player, any portable, mobile, handheld device, or any machine capable of executing a set of instructions (sequential or otherwise) that specify actions to be taken by the processing system.

While the main memory 3006, non-volatile memory 3010, and storage medium 3026 (also called a "machine-readable medium) are shown to be a single medium, the term "machine-readable medium" and "storage medium" should be taken to include a single medium or multiple media (e.g., a centralized or distributed database, and/or associated caches and servers) that store one or more sets of instructions 3028. The term "machine-readable medium" and "storage medium" shall also be taken to include any medium that is capable of storing, encoding, or carrying a set of instructions for execution by the processing system and that cause the processing system to perform any one or more of the methodologies of the presently disclosed embodiments.

In general, the routines executed to implement the embodiments of the disclosure, may be implemented as part of an operating system or a specific application, component, program, object, module or sequence of instructions referred to as "computer programs." The computer programs typically comprise one or more instructions (e.g., instructions 3004, 3008, 3028) set at various times in various memory and storage devices in a computer, and that, when read and executed by one or more processing units or processors 3002, cause the processing system 3000 to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices 3010, floppy and other removable disks, hard disk drives, optical disks (e.g., Compact Disk Read-Only Memory (CD ROMS), Digital Versatile Disks, (DVDs)), and transmission type media such as digital and analog communication links.

The network adapter 3012 enables the processing system 3000 to mediate data in a network 3014 with an entity that is external to the computing device 3000, through any known and/or convenient communications protocol supported by the processing system 3000 and the external entity. The network adapter 3012 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 3012 can include a firewall that can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

As indicated above, the computer-implemented systems introduced here can be implemented by hardware (e.g., programmable circuitry such as microprocessors), software, firmware, or a combination of such forms. For example, some computer-implemented systems may be embodied entirely in special-purpose hardwired (i.e., non-programmable) circuitry. Special-purpose circuitry can be in the form of, for example, application-specific integrated circuits (ASICs), programmable logic devices (PLDs), field-programmable gate arrays (FPGAs), etc.

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

What is claimed is:

1. An apparatus comprising:
a remote adapted to engage a medication container, said remote comprising a purposed acoustic emitter adapted to emit a characteristic acoustic emission in user-transparent consequential response to a remote event;
a station, comprising:
a processor; and
a receiver in communication with said processor;
wherein said processor is adapted to determine whether said characteristic acoustic emission is characteristic of said purposed acoustic emitter, and to register said remote event if said characteristic acoustic emission is determined to be characteristic of said purposed acoustic emitter.

2. The apparatus of claim 1, wherein:
said remote is adapted to removably engage said medication container.

3. The apparatus of claim 1, wherein:
said remote defines an aperture therein adapted to accept said medication container therein, such that compressing said body compresses said medication container so as to dispense a medication therefrom.

4. The apparatus of claim 1, wherein:
said purposed acoustic emitter comprises a whistle adapted to produce said characteristic acoustic emission when air is passed therethrough.

5. The apparatus of claim 1, wherein:
said purposed acoustic emitter is adapted to produce an ultrasonic pitch as at least a portion of said characteristic acoustic emission.

6. The apparatus of claim 1, wherein:
said purposed acoustic emitter is adapted to produce at least two pitches in combination as at least a portion of said characteristic acoustic emission.

7. The apparatus of claim 1, wherein:
said purposed acoustic emitter is adapted to produce a characteristic acoustic wave form as at least a portion of said characteristic acoustic emission.

8. The apparatus of claim 1, wherein:
said purposed acoustic emitter is adapted to produce a characteristic acoustic sequence as at least a portion of said characteristic acoustic emission.

9. The apparatus of claim 1, wherein:
said station comprises a smart phone.

10. The apparatus of claim 1, wherein:
said station comprises a dedicated unit.

11. The apparatus of claim 1, wherein:
said station comprises at least one of a data store, a display, a communicator, and a user interface.

12. The apparatus of claim 1, wherein:
said processor is adapted to determine and register supplemental remote event data, comprising at least one of a time of said remote event, an environmental condition associated with said remote event, a user condition associated with said remote event, and a property of said remote event.

13. The apparatus of claim 12, wherein:
said remote event comprises dispensing said medication from said medication container; and
said supplemental remote event data comprises a quantity of said medication dispensed.

14. A method comprising:
establishing a remote, said remote being adapted to engage with a medication container adapted to contain and dispense a medication, said remote comprising a purposed characteristic acoustic emitter engaged with said medication container;
establishing a station comprising a processor and an acoustic receiver in communication with said processor;
in transparent and direct response to a remote event, emitting from said purposed characteristic acoustic emitter a characteristic acoustic emission;
receiving said characteristic acoustic emission in said acoustic receiver;
communicating said characteristic acoustic emission to said processor;
in said processor, determining that said characteristic acoustic emission is characteristic of said purposed acoustic emitter;
in said processor, registering said remote event if said characteristic acoustic emission is determined to be characteristic of said purposed acoustic emitter.

15. The method of claim 14, comprising:
determining supplemental remote event data in said processor, said supplemental remote event data comprising at least one of a time of said remote event, an environmental condition associated with said remote event, a user condition associated with said remote event, and a property of said remote event; and
registering said supplemental remote event data if said characteristic acoustic emission is determined to be characteristic of said purposed acoustic emitter.

16. The method of claim 15, wherein:
said remote event comprises dispensing said medication from said medication container; and
said supplemental remote event data comprises a quantity of said medication dispensed.

17. The method of claim 14, wherein:
said station comprises a smart phone; and
establishing said station comprises instantiating executable instructions on said smart phone.

18. The method of claim 14, wherein:
said station comprises a dedicated unit; and
establishing said station comprises disposing said unit in a proximity of said remote.

19. The method of claim 14, wherein:
said station comprises at least one of a data store, a display, a communicator, and a user interface; and
registering said remote event comprises at least a corresponding one of recording said remote event in said data store, outputting said remote event to said display, communicating said remote event to a recipient via said communicator, and accepting input regarding said remote event via said user interface.

* * * * *